United States Patent
Brendel et al.

(10) Patent No.: US 7,982,045 B2
(45) Date of Patent: *Jul. 19, 2011

(54) 2'-SUBSTITUTED 1,1'-BIPHENYL-2-CARBOXAMIDES, PROCESSES FOR THEIR PREPARATION, THEIR USE AS MEDICAMENTS, AND PHARMACEUTICAL PREPARATIONS COMPRISING THEM

(75) Inventors: Joachim Brendel, Bad Vibel (DE); Wolfgang Schmidt, Frankfurt (DE); Peter Below, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/419,069

(22) Filed: Apr. 6, 2009

(65) Prior Publication Data
US 2009/0192096 A1 Jul. 30, 2009

Related U.S. Application Data

(60) Continuation of application No. 10/691,624, filed on Oct. 24, 2003, now Pat. No. 7,514,582, which is a division of application No. 10/252,385, filed on Sep. 24, 2002, now Pat. No. 6,686,395, which is a division of application No. 09/698,078, filed on Oct. 30, 2000, now Pat. No. 6,531,495, which is a continuation-in-part of application No. 09/675,674, filed on Sep. 29, 2000, now abandoned.

(51) Int. Cl.
*A61K 31/44* (2006.01)
*C07D 213/02* (2006.01)

(52) U.S. Cl. ........ 546/329; 546/334; 546/336; 546/337; 514/357

(58) Field of Classification Search .................. 546/329, 546/334, 336, 337; 514/357
See application file for complete search history.

(56) References Cited

U.S. PATENT DOCUMENTS
5,521,170 A 5/1996 Setoi et al.
6,531,495 B1 * 3/2003 Brendel et al. ................ 514/357
2003/0171351 A1 9/2003 Bendel et al.

FOREIGN PATENT DOCUMENTS
EP 0620216 10/1994
WO 96/25936 8/1996
WO 97/23451 7/1997
WO 98/04521 2/1998
WO 98/18475 5/1998
WO 98/18476 5/1998

OTHER PUBLICATIONS

Brandmeier, et al., Antiparallel beta-Sheet Conformation in Cyclopeptides Containing a Pseudo-amino Acid with a Biphenyl Moiety, Helvetica Chima Acta; 77; 1994; pp. 70-85.
Dorwald, F.A., Side reactions in organic synthesis, Wiley-VCH, Weinheim, 2005; p. IX of Preface.
Caplus AN 2001:608248 English Abstract, Chemstar Product List RN# 328284 May 16, 2001.
Knobloch, et al., Antiarrhythmic Effects of KV1.5 Channel Blockers . . . , Abstract, Thorac Cardiovasc Surg. 2002; Feb. 19, 2002.
Lullman, et al., Pharmakologie und Toxikologie; XP002159084, Georg Thieme Verlag, Stuttgart; 1999; pp. 151-153.
Oxford, et al., Caplus English Abstract EP 533266, 1993.
Himmelsbach, et al., Caplus English Abstract EP 496378, 1992.
Geurtin, K.,Caplus English abstract DN 127:136073, (1997).

* cited by examiner

*Primary Examiner* — Rita J Desai
(74) *Attorney, Agent, or Firm* — Serena Farquharson-Torres; Scully, Scott, Murphy & Presser, P.C.

(57) ABSTRACT

Compounds of the formula I,

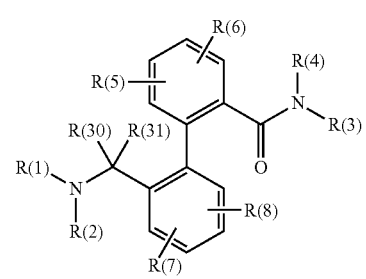

in which R(1), R(2), R(3), R(4), R(5), R(6), R(7), R(8), R(30) and R(31) have the meanings indicated in the claims, are very particularly suitable as novel and antiarrythmic active compounds, in particular for the treatment and prophylaxis of atrial arrythmias, e.g. atrial fibrillation (AF), or atrial flutter.

6 Claims, No Drawings

2'-SUBSTITUTED 1,1'-BIPHENYL-2-CARBOXAMIDES, PROCESSES FOR THEIR PREPARATION, THEIR USE AS MEDICAMENTS, AND PHARMACEUTICAL PREPARATIONS COMPRISING THEM

This application claims the benefit of foreign priority under 35 U.S.C. §119 to German patent application no. 19947457.5, filed on Oct. 2, 1999, the contents of which are incorporated by reference herein.

The invention relates to compounds of the formula I,

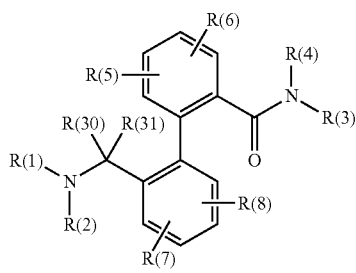

in which R(1), R(2), R(3), R(4), R(5), R(6), R(7), R(8), R(30) and R(31) have the meanings indicated below, their preparation and their use, in particular in pharmaceuticals.

The compounds of the formula I according to the invention were hitherto unknown. They act on the so-called Kv1.5 potassium channel and inhibit a potassium current described as "ultra-rapidly activating delayed rectifier" in the human atrium. The compounds are therefore very particularly suitable as novel antiarrhythmic active compounds, in particular for the treatment and prophylaxis of atrial arrhythmias, e.g. atrial fibrillation (AF) or atrial flutter.

The compounds can be used for the termination of existing atrial fibrillation or flutter to restore sinus rhythm (cardioversion). Furthermore the compounds reduce the incidence for the development of new episodes of fibrillation (maintenance of sinus rhythm, prophylaxis).

Atrial fibrillation (AF) and atrial flutter are the most frequent persistent cardiac arrhythmias. The occurrence increases with increasing age and frequently leads to fatal sequelae, such as, for example, cerebral apoplexy. AF affects about 1 million Americans annually and leads to more than 80,000 strokes each year in the USA. The presently customary antiarrhythmics of classes I and III, reduce the reoccurrence rate of AF, but because of their potential proarrhythmic side effects only have restricted use. There is therefore a great medical need for the development of better medicaments for the treatment of atrial arrhythmias (S. Nattel, Am. Heart J. 130, 1995, 1094-1106; "Newer developments in the management of atrial fibrillation").

It was shown that most supraventricular arrhythmias are subject to so-called "reentry" excitatory waves. Such reentries occur when the cardiac tissue has a slow conductivity and at the same time very short refractory periods. The increasing of the myocardial refractory time by prolongation of the action potential is a recognized mechanism for ending arrhythmias or preventing their formation (T. J. Colatsky et al., Drug Dev. Res. 19, 1990, 129-140; "Potassium channels as targets for antiarrhythmic drug action"). The length of the action potential is essentially determined by the extent of repolarizing $K^+$ currents which flow out of the cell via various $K^+$ channels. Particularly great importance is ascribed here to the so-called "delayed rectifier" $I_K$, which consists of 3 different components: $IK_r$, $IK_s$ and $IK_{ur}$.

Most known class III antiarrhythmics (e.g. dofetilide, E4031 and d-sotalol) mainly or exclusively block the rapidly activating potassium channel $IK_r$, which can be detected both in cells of the human ventricle and in the atrium. However, it has been shown that at low or normal heart rates these compounds have an increased proarrhythmic risk, arrhythmias which are described as "Torsades de pointes" being observed in particular (D. M. Roden, Am. J. Cardiol. 72, 1993, 44B-49B; "Current status of class III antiarrhythmic drug therapy"). In addition to this high, in some cases fatal, risk at low frequency, a decrease in the efficacy under the conditions of tachycardia, in which the action is especially needed, has been found for the $I_{Kr}$ blockers ("negative use-dependence").

While some of these disadvantages can possibly be overcome by blockers of the slowly activating components ($IK_s$), their efficacy has hitherto not been confirmed, as no clinical investigations with $IK_s$ channel blockers are known.

The "particularly rapidly" activating and very slowly inactivating component of the delayed rectifier $IK_{ur}$ (=ultra-rapidly activating delayed rectifier), which corresponds to the Kv1.5 channel, plays a particularly large role in the repolarization period in the human atrium. In comparison to the inhibition of $IK_r$ or $IK_s$, inhibition of the $IK_{ur}$ potassium outward current is thus a particularly effective method for the prolongation of the atrial action potential and thus for the ending or prevention of atrial arrhythmias. Mathematical models of the human action potential suggest that the positive effect of a blockade of the $IK_{ur}$, especially under the pathological conditions of chronic atrial fibrillation, should be particularly pronounced (M. Courtemanche, R. J. Ramirez, S, Nattel, Cardiovascular Research 1999, 42, 477-489: "Ionic targets for drug therapy and atrial fibrillation-induced electrical remodeling: insights from a mathematical model").

In contrast to $IK_r$ and $IK_s$, which also occur in the human ventricle, the $IK_{ur}$ admittedly plays an important role in the human atrium, but not in the ventricle. For this reason, on inhibition of the $IK_{ur}$ current in contrast to the blockade of $IK_r$ or $IK_s$, the risk of a proarrhythmic action on the ventricle is excluded from the start (Z. Wang et al., Circ. Res. 73, 1993, 1061-1076: "Sustained Depolarisation-Induced Outward Current in Human Atrial Myocytes"; G.-R. Li et al, Circ. Res. 78, 1996, 689-696: "Evidence for Two Components of Delayed Rectifier $K^+$ Current in Human Ventricular Myocytes"; G. J. Amos et al., J. Physiol. 491, 1996, 31-50: "Differences between outward currents of human atrial and subepicardial ventricular myocytes").

Antiarrhythmics which act via a selective blockade of the $IK_{ur}$ current or Kv1.5 channel were previously not available, however, on the market. For numerous pharmaceutical active compounds (e.g. tedisamil, bupivacaine or sertindole), a blocking action on the Kv1.5 channel was admittedly described, but the Kv1.5 blockade here in each case represents only a side effect next to other principal actions of the substances.

WO 98 04 521 claims aminoindans as potassium channel blockers which block the Kv1.5 channel. The applications WO 98 18 475 and WO 98 18 476 claim the use of various pyridazinones and phosphine oxides as antiarrhythmics, which should act via a blockade of the $IK_{ur}$. However, the same compounds were originally also described as immunosuppressants (WO 96 25 936). The compounds described in these mentioned applications are structurally completely different to the compounds according to the invention of this application.

It has now surprisingly been found that the 2'-substituted 1,1'-biphenyl-2-carboxamides described here are potent blockers of the human Kv1.5 channel. They can therefore be used as novel antiarrhythmics having a particularly advantageous safety profile. In particular, the compounds are suitable for the treatment of supraventricular arrhythmias, e.g. atrial fibrillation or atrial flutter.

The compounds according to the invention were previously unknown. Some structurally related compounds are described in Helv. Chim. Acta 1994 (70) 70 and references cited there. For the peptide compounds described there (e.g. compound A), however, no potassium channel-blocking activity is known. Moreover, compounds of this type should have too low a metabolic stability for use as antiarrhythmics on account of the numerous peptide bonds.

compound A

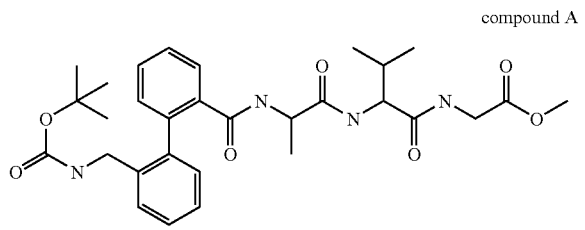

A further similar compound (compound B) is mentioned in European Patent Application EP 0620216. The compound B and all other compounds of this application carry, in the position of R(3), a specific substituent (e.g. benzoyl-1,2,3,4-tetrahydroisoquinoline), which is not included in the compounds according to the invention of this application. The compounds mentioned in EP 0 620 216 act as vasopressin antagonists and thus have a completely different biological activity to the blockers of the Kv1.5 channel described here.

compound B

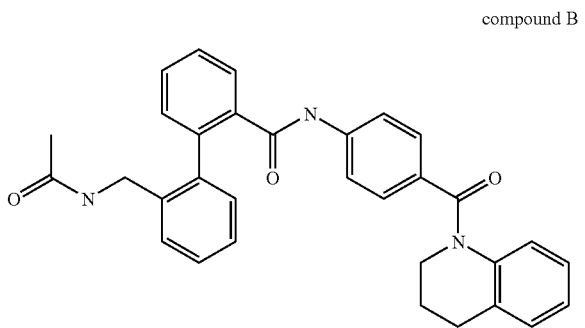

The present invention relates to compounds of the formula I

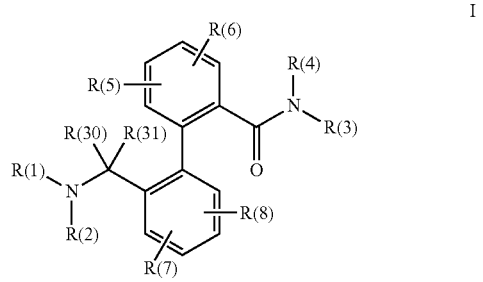

in which:
R(1) is C(O)OR(9), SO$_2$R(10), COR(11), C(O)NR(12)R(13) or C(S)NR(12)R(13);
R(9) is C$_x$H$_{2x}$—R(14);
x is 0, 1, 2, 3 or 4, where x cannot be 0 if R(14) is OR(15) or SO$_2$Me;
R(14) is alkyl having 1, 2, 3, 4, 5 or 6 carbon atoms, cycloalkyl having 3, 4, 5, 6, 7, 8, 9, 10 or 11 carbon atoms, CF$_3$, OCF$_3$, C$_2$F$_5$, C$_3$F$_7$, CH$_2$F, CHF$_2$, OR(15), SO$_2$Me, phenyl, naphthyl, biphenylyl, furyl, thienyl or an N-containing heteroaromatic having 1, 2, 3, 4, 5, 6, 7, 8 or 9 carbon atoms,
where phenyl, naphthyl, biphenylyl, furyl, thienyl and the N-containing hetero-aromatic are unsubstituted or substituted by 1, 2 or 3 substituents selected from the group consisting of F, Cl, Br, I, OCF$_3$, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(15) is alkyl having 1, 2, 3, 4 or 5 carbon atoms, cycloalkyl having 3, 4, 5 or 6 carbon atoms, CF$_3$ or phenyl which is unsubstituted or substituted by 1, 2 or 3 substituents selected from the group consisting of F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(10), R(11) and R(12) independently of one another are defined as R(9);
R(13) is hydrogen, alkyl having 1, 2, 3 or 4 carbon atoms or CF$_3$;
R(2) is hydrogen, alkyl having 1, 2, 3 or 4 carbon atoms or CF$_3$;
R(3) is C$_y$H$_{2y}$—R(16);
y is 0, 1, 2, 3 or 4,
where y cannot be 0 if R(16) is OR(17) or SO$_2$Me;
R(16) is alkyl having 1, 2, 3, 4, 5 or 6 carbon atoms, cycloalkyl having 3, 4, 5, 6, 7, 8, 9, 10 or 11 carbon atoms, CF$_3$, C$_2$F$_5$, C$_3$F$_7$, CH$_2$F, CHF$_2$, OR(17), SO$_2$Me, phenyl, naphthyl, furyl, thienyl or an N-containing hetero-aromatic having 1, 2, 3, 4, 5, 6, 7, 8 or 9 carbon atoms,
where phenyl, naphthyl, furyl, thienyl and the N-containing heteroaromatic are unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(17) is hydrogen, alkyl having 1, 2, 3, 4 or 5 carbon atoms, cycloalkyl having 3, 4, 5 or 6 carbon atoms, CF$_3$, phenyl or 2-, 3- or 4-pyridyl,
where phenyl or 2-, 3- or 4-pyridyl are unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

or

R(3) is CHR(18)R(19);
R(18) is hydrogen or $C_zH_{2z}$—R(16), where R(16) is defined as indicated above;
z is 0, 1, 2 or 3;
R(19) is COOH, CONH$_2$, CONR(20)R(21), COOR(22), CH$_2$OH;
R(20) is hydrogen, alkyl having 1, 2, 3, 4 or 5 carbon atoms, $C_vH_{2v}$-CF$_3$ or $C_wH_{2w}$-phenyl,
where the phenyl ring is unsubstituted or substituted by 1, 2 or 3 substituents selected from the group consisting of F, Cl, Br, I, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
v is 0, 1, 2 or 3;
w is 0, 1, 2 or 3;
R(21) is hydrogen or alkyl having 1, 2, 3, 4 or 5 carbon atoms;
R(22) is alkyl having 1, 2, 3, 4 or 5 carbon atoms;
R(4) is hydrogen, alkyl having 1, 2, 3, 4, 5 or 6 carbon atoms or CF$_3$;
or
R(3) and R(4)
together are a chain of 4 or 5 methylene groups, of which one methylene group can be replaced by —O—, —S—, —NH—, —N(methyl)- or —N(benzyl)-;
R(5), R(6), R(7) and R(8)
independently of one another are hydrogen, F, Cl, Br, I, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;
R(30) and R(31)
independently of one another hydrogen or alkyl having 1, 2 or 3 carbon atoms;
or
R(30) and R(31)
together form a chain of 2 methylene groups;
and their pharmaceutically acceptable salts.

Preferred compounds of the formula I are those in which:
R(1) is C(O)OR(9), SO$_2$R(10), COR(11) or C(O)NR(12)R(13);
R(9) is $C_xH_{2x}$—R(14);
x is 0, 1, 2, 3 or 4,
where x cannot be 0 if R(14) is OR(15);
R(14) is alkyl having 1, 2, 3 or 4 carbon atoms, cycloalkyl having 3, 4, 5, 6, 7, 8 or 9 carbon atoms, CF$_3$, C$_2$F$_5$, OR(15), phenyl, furyl, thienyl or an N-containing heteroaromatic having 1, 2, 3, 4, 5, 6, 7, 8 or 9 carbon atoms,
where phenyl, furyl, thienyl and the N-containing heteroaromatic are unsubstituted or substituted by 1, 2 or 3 substituents selected from the group consisting of F, Cl, Br, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(15) is alkyl having 1, 2, 3, 4 or 5 carbon atoms, cycloalkyl having 3, 4, 5 or 6 carbon atoms, CF$_3$ or phenyl,
which is unsubstituted or substituted by 1, 2 or 3 substituents selected from the group consisting of F, Cl, Br, CF$_3$, NO$_2$, CN, COOMe, CONH$_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(10), R(11) and R(12)
independently of one another are defined as R(9);
R(13) is hydrogen, alkyl having 1, 2, 3 or 4 carbon atoms or CF$_3$;
R(2) is hydrogen, alkyl having 1, 2, 3 or 4 carbon atoms or CF$_3$;
R(3) is $C_yH_{2y}$—R(16);
y is 0, 1, 2, 3 or 4,
where y cannot be 0 if R(16) is OR(17);
R(16) is alkyl having 1, 2, 3 or 4 carbon atoms, cycloalkyl having 3, 4, 5, 6, 7, 8 or 9 carbon atoms, CF$_3$, C$_2$F$_5$, OR(17), phenyl, furyl, thienyl or an N-containing hetero-aromatic having 1, 2, 3, 4, 5, 6, 7, 8 or 9 carbon atoms,
where phenyl, furyl, thienyl and the N-containing heteroaromatic are unsubstituted or substituted by 1, 2 or 3 substituents selected from the group consisting of F, Cl, Br, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(17) is alkyl having 1, 2, 3, 4 or 5 carbon atoms, cycloalkyl having 3, 4, 5 or 6 carbon atoms, CF$_3$, phenyl or 2-, 3-, or 4-pyridyl,
where phenyl or 2-, 3- or 4-pyridyl are unsubstituted or substituted by 1, 2 or 3 substituents selected from the group consisting of F, Cl, Br, CF$_3$, OCF$_3$, NO$_2$, CN, COOMe, CONH$_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
or
R(3) is CHR(18)R(19);
R(18) is hydrogen or $C_zH_{2z}$—R(16), where R(16) is defined as indicated above;
z is 0, 1, 2 or 3;
R(19) is CONH$_2$, CONR(20)R(21), COOR(22), CH$_2$OH;
R(20) is hydrogen, alkyl having 1, 2, 3, 4 or 5 carbon atoms, $C_vH_{2v}$—CF$_3$ or $C_wH_{2w}$-phenyl,
where the phenyl ring is unsubstituted or substituted by 1, 2 or 3 substituents selected from the group consisting of F, Cl, Br, CF$_3$, OCF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
v is 0, 1, 2 or 3;
w is 0, 1, 2 or 3;
R(21) is hydrogen or alkyl having 1, 2, 3, 4 or 5 carbon atoms;
R(22) is alkyl having 1, 2, 3, 4 or 5 carbon atoms;
R(4) is hydrogen, alkyl having 1, 2, 3, 4, 5 or 6 carbon atoms or CF$_3$;
R(5), R(6), R(7) and R(8)
independently of one another are hydrogen, F, Cl, Br, CF$_3$, NO$_2$, CN, COOMe, CONH$_2$, COMe, NH$_2$, OH, alkyl having 1, 2, 3 or 4 carbon atoms, alkoxy having 1, 2, 3 or 4 carbon atoms, dimethylamino, sulfamoyl, methylsulfonyl or methylsulfonylamino;
R(30) and R(31)
independently of one another hydrogen or alkyl having 1, 2 or 3 carbon atoms;

or
R(30) and R(31)
    together form a chain of 2 methylene groups;
and their pharmaceutically acceptable salts.

Particularly preferred compounds of the formula I are those in which:
R(1) is C(O)OR(9), $SO_2$R(10), COR(11) or C(O)NR(12)R(13);
  R(9) is $C_xH_{2x}$—R(14);
    x is 0, 1, 2, 3 or 4,
      where x cannot be 0 if R(14) is OR(15);
    R(14) is cycloalkyl having 3, 4, 5, 6, 7, 8 or 9 carbon atoms, $CF_3$, OR(15), phenyl, furyl, thienyl or an N-containing heteroaromatic having 3, 4 or 5 carbon atoms,
      where phenyl, furyl, thienyl and the N-containing heteroaromatic are unsubstituted or substituted by 1 or 2 substituents selected from the group consisting of F, Cl, Br, $CF_3$, $OCF_3$, CN, COOMe, $CONH_2$, COMe, OH, alkyl having 1, 2 or 3 carbon atoms, alkoxy having 1 or 2 carbon atoms, dimethylamino, sulfamoyl, methylsulfonyl and methylsulfonylamino;
    R(15) is alkyl having 1 or 2 carbon atoms, cycloalkyl having 3, 4, 5 or 6 carbon atoms, $CF_3$ or phenyl,
      which is unsubstituted or substituted by 1 or 2 substituents selected from the group consisting of F, Cl, Br, $CF_3$, CN, COOMe, $CONH_2$, COMe, OH, alkyl having 1, 2 or 3 carbon atoms, alkoxy having 1 or 2 carbon atoms, dimethylamino, sulfamoyl, methylsulfonyl and methylsulfonylamino;
  R(10), R(11) and R(12)
    independently of one another are defined as R(9);
  R(13) is hydrogen;
R(2) is hydrogen or alkyl having 1, 2 or 3 carbon atoms;
R(3) is CHR(18)R(19);
  R(18) is hydrogen or $C_zH_{2z}$—R(16);
    z is 0, 1, 2 or 3;
  R(19) is $CONH_2$, CONR(20)R(21), COOR(22) or $CH_2OH$;
    R(20) is hydrogen, alkyl having 1, 2, 3, 4 or 5 carbon atoms, $C_vH_{2v}$-$CF_3$ or $C_wH_{2w}$-phenyl,
      where the phenyl ring is unsubstituted or substituted by 1, 2 or 3 substituents selected from the group consisting of F, Cl, Br, $CF_3$, $OCF_3$, CN, COOMe, $CONH_2$, COMe, OH, alkyl having 1, 2 or 3 carbon atoms, alkoxy having 1 or 2 carbon atoms, dimethylamino, sulfamoyl, methylsulfonyl and methylsulfonylamino;
    v is 0, 1, 2 or 3;
    w is 0, 1, 2 or 3;
    R(21) is hydrogen or alkyl having 1, 2, 3, 4 or 5 carbon atoms;
    R(22) is alkyl having 1, 2, 3, 4 or 5 carbon atoms;
  R(16) is alkyl having 1, 2 or 3 carbon atoms, cycloalkyl having 3, 4, 5, 6, 7, 8 or 9 carbon atoms, $CF_3$, OR(17), phenyl, furyl, thienyl or an N-containing heteroaromatic having 3, 4 or 5 carbon atoms,
    where phenyl, furyl, thienyl and the N-containing heteroaromatic are unsubstituted or substituted by 1 or 2 substituents selected from the group consisting of F, Cl, Br, $CF_3$, $OCF_3$, CN, COOMe, $CONH_2$, COMe, $NH_2$, OH, alkyl having 1, 2 or 3 carbon atoms, alkoxy having 1 or 2 carbon atoms, dimethylamino, sulfamoyl, methylsulfonyl and methylsulfonylamino;
    R(17) is alkyl having 1, 2, 3 or 4 carbon atoms, cycloalkyl having 3, 4, 5 or 6 carbon atoms, $CF_3$, phenyl or 2-, 3- or 4-pyridyl,
      where phenyl or 2-, 3- or 4-pyridyl are unsubstituted or substituted by 1, 2 or 3 substituents selected from the group consisting of F, Cl, Br, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(4) is hydrogen or alkyl having 1 or 2 carbon atoms;
R(5), R(6), R(7) and R(8)
  independently of one another are hydrogen, F, Cl, Br, $CF_3$, CN, COOMe, $CONH_2$, COMe, $NH_2$, OH, alkyl having 1, 2 or 3 carbon atoms, alkoxy having 1 or 2 carbon atoms, dimethylamino, sulfamoyl, methylsulfonyl or methylsulfonylamino;
R(30) and R(31)
  independently of one another hydrogen or methyl;
or
R(30) and R(31)
  together form a chain of 2 methylene groups;
and their pharmaceutically acceptable salts.

Particularly preferred compounds of the formula I are also those in which:
R(1) is C(O)OR(9), $SO_2$R(10), COR(11) or C(O)NR(12)R(13);
  R(9) is $C_xH_{2x}$—R(14);
    x is 0, 1, 2, 3 or 4,
    where x cannot be 0 if R(14) is OR(15);
    R(14) is alkyl having 1, 2, 3 or 4 carbon atoms, cycloalkyl having 3, 4, 5, 6, 7, 8 or 9 carbon atoms, $CF_3$, OR(15), phenyl, furyl, thienyl or an N-containing heteroaromatic having 3, 4 or 5 carbon atoms,
      where phenyl, furyl, thienyl and the N-containing heteroaromatic are unsubstituted or substituted by 1 or 2 substituents selected from the group consisting of F, Cl, Br, $CF_3$, $OCF_3$, CN, COOMe, $CONH_2$, COMe, OH, alkyl having 1, 2 or 3 carbon atoms, alkoxy having 1 or 2 carbon atoms, dimethylamino, sulfamoyl, methylsulfonyl and methylsulfonylamino;
    R(15) is alkyl having 1 or 2 carbon atoms, cycloalkyl having 3, 4, 5 or 6 carbon atoms, $CF_3$ or phenyl,
      which is unsubstituted or substituted by 1 or 2 substituents selected from the group consisting of F, Cl, Br, $CF_3$, CN, COOMe, $CONH_2$, COMe, OH, alkyl having 1, 2 or 3 carbon atoms, alkoxy having 1 or 2 carbon atoms, dimethylamino, sulfamoyl, methylsulfonyl and methylsulfonylamino;
  R(10), R(11) and R(12)
    independently of one another are defined as R(9);
  R(13) is hydrogen;
R(2) is hydrogen or alkyl having 1, 2 or 3 carbon atoms;
R(3) is $C_yH_{2y}$—R(16);
  y is 0, 1, 2, 3 or 4,
  where y cannot be 0 if R(16) is OR(17);
  R(16) is alkyl having 1, 2 or 3 carbon atoms, cycloalkyl having 3, 4, 5, 6, 7, 8 or 9 carbon atoms, $CF_3$, OR(17), phenyl, furyl, thienyl or an N-containing heteroaromatic having 3, 4 or 5 carbon atoms,
    where phenyl, furyl, thienyl and the N-containing heteroaromatic are unsubstituted or substituted by 1 or 2 substituents selected from the group consisting of F, Cl, Br, $CF_3$, $OCF_3$, CN, COOMe, $CONH_2$, COMe, $NH_2$, OH, alkyl having 1, 2 or 3 carbon atoms, alkoxy having 1 or 2 carbon atoms, dimethylamino, sulfamoyl, methylsulfonyl and methylsulfonylamino;
R(17) is alkyl having 1, 2, 3, 4 or 5 carbon atoms, cycloalkyl having 3, 4, 5 or 6 carbon atoms, $CF_3$, phenyl or 2-, 3- or 4-pyridyl,
where phenyl or 2-, 3- or 4-pyridyl are unsubstituted or substituted by 1, 2 or 3 substituents selected from the group consisting of F, Cl, Br, $CF_3$, $OCF_3$, $NO_2$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R(4) is hydrogen or alkyl having 1 or 2 carbon atoms;
R(5), R(6), R(7) and R(8)
independently of one another are hydrogen, F, Cl, Br, $CF_3$, CN, COOMe, $CONH_2$, COMe, $NH_2$, OH, alkyl having 1, 2 or 3 carbon atoms, alkoxy having 1 or 2 carbon atoms, dimethylamino, sulfamoyl, methylsulfonyl or methylsulfonylamino;
R(30) and R(31)
independently of one another hydrogen or methyl;
or
R(30) and R(31)
together form a chain of 2 methylene groups;
and their pharmaceutically acceptable salts.

Very particularly preferred compounds of the formula I are those in which:
R(1) is C(O)OR(9), $SO_2R(10)$, COR(11) or C(O)NR(12)R(13);
R(9) is $C_xH_{2x}$—R(14);
x is 0, 1, 2 or 3;
R(14) is alkyl having 1, 2, 3 or 4 carbon atoms, cycloalkyl having 3, 4, 5, 6, 7, 8 or 9 carbon atoms, $CF_3$, phenyl or pyridyl,
where phenyl and pyridyl are unsubstituted or substituted by 1 or 2 substituents selected from the group consisting of F, Cl, $CF_3$, $OCF_3$, OH, alkyl having 1, 2 or 3 carbon atoms and alkoxy having 1 or 2 carbon atoms;
R(10), R(11) and R(12)
independently of one another are defined as R(9);
R(13) is hydrogen;
R(2) is hydrogen;
R(3) is $C_yH_{2y}$—R(16);
y is 0, 1 or 2;
R(16) is alkyl having 1, 2 or 3 carbon atoms, cycloalkyl having 5 or 6 carbon atoms, $CF_3$, phenyl or pyridyl,
where phenyl and pyridyl are unsubstituted or substituted by 1 or 2 substituents selected from the group consisting of F, Cl, $CF_3$, $OCF_3$, OH, alkyl having 1, 2 or 3 carbon atoms and alkoxy having 1 or 2 carbon atoms;
R(4) is hydrogen;
R(5), R(6), R(7) and R(8)
independently of one another are hydrogen, F, $CF_3$, CN, COOMe, $CONH_2$, $NH_2$, OH, alkyl having 1, 2 or 3 carbon atoms or alkoxy having 1 or 2 carbon atoms;
R(30) and R(31)
independently of one another hydrogen or methyl;
or
R(30) and R(31)
together form a chain of 2 methylene groups;
and their pharmaceutically acceptable salts.

Especially preferred compounds of the formula I are those in which:
R(1) is C(O)OR(9) or COR(11);
R(9) is $C_xH_{2x}$—R(14);
x is 0, 1, 2 or 3;
R(14) is cycloalkyl having 5 or 6 carbon atoms or phenyl,
where phenyl is unsubstituted or substituted by 1 or 2 substituents selected from the group consisting of F, Cl, $CF_3$, $OCF_3$, alkyl having 1, 2 or 3 carbon atoms and alkoxy having 1 or 2 carbon atoms;
R(11) is defined as R(9);
R(2) is hydrogen;
R(3) is $C_yH_{2y}$—R(16);
y is 0, 1 or 2;
R(16) is alkyl having 1, 2 or 3 carbon atoms, cycloalkyl having 5 or 6 carbon atoms, $CF_3$, phenyl or pyridyl
where phenyl and pyridyl are unsubstituted or substituted by 1 or 2 substituents selected from the group consisting of F, Cl, $CF_3$, $OCF_3$, alkyl having 1, 2 or 3 carbon atoms and alkoxy having 1 or 2 carbon atoms;
R(4) is hydrogen;
R(5), R(6), R(7) and R(8)
independently of one another are hydrogen, F, $CF_3$, alkyl having 1, 2 or 3 carbon atoms or alkoxy having 1 or 2 carbon atoms;
R(30) and R(31)
are hydrogen;
and their pharmaceutically acceptable salts.

Alkyl radicals and alkylene radicals can be straight-chain or branched. This also applies to the alkylene radicals of the formulae $C_xH_{2x}$, $C_yH_{2y}$, $C_zH_{2z}$, $C_vH_{2v}$ and $C_wH_{2w}$. Alkyl radicals and alkylene radicals can also be straight-chain or branched if they are substituted or are contained in other radicals, e.g. in an alkoxy radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, eicosyl. The divalent radicals derived from these radicals, e.g. methylene, 1,1-ethylene, 1,2-ethylene, 1,1-propylene, 1,2-propylene, 2,2-propylene, 1,3-propylene, 1,1-butylene, 1,4-butylene, 1,5-pentylene, 2,2-dimethyl-1,3-propylene, 1,6-hexylene, etc., are examples of alkylene radicals.

Cycloalkyl radicals can likewise be branched. Examples of cycloalkyl radicals having 3 to 11 carbon atoms are cyclopropyl, cyclobutyl, 1-methylcyclopropyl, 2-methylcyclopropyl, cyclopentyl, 2-methylcyclobutyl, 3-methylcyclobutyl, cyclopentyl, cyclohexyl, 2-methylcyclohexyl, 3-methylcyclohexyl, 4-methylcyclohexyl, menthyl, cycloheptyl, cyclooctyl etc.

N-containing heteroaromatics having 1, 2, 3, 4, 5, 6, 7, 8 or 9 carbon atoms are considered in particular as 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. The corresponding N-oxides of these compounds are furthermore included, i.e., for example, 1-oxy-2-, -3- or -4-pyridyl.

The N-containing heterocycles pyrrolyl, imidazolyl, quinolyl, pyrazolyl, pyridyl, pyrazinyl, pyrimidinyl and pyridazinyl are particularly preferred.

Pyridyl is either 2-, 3- or 4-pyridyl. Thienyl is either 2- or 3-thienyl. Furyl is either 2- or 3-furyl.

Monosubstituted phenyl radicals can be substituted in the 2, 3 or 4 position, disubstituted in the 2,3, 2,4, 2,5, 2,6, 3,4 or 3,5 position, or trisubstituted in the 2,3,4, 2,3,5, 2,3,6, 2,4,5, 2,4,6 or 3,4,5 position. The same correspondingly also applies analogously to the N-containing heteroaromatics, the thiophene or the furyl radical.

If a radical is di- or trisubstituted, the substituents can be identical or different.

If R(3) and R(4) are together a chain of 4 or 5 methylene groups, of which one methylene group can be replaced by —O—, —S—, —NH— etc., then these radicals together with the nitrogen atom of the compound of the formula I form a 5- or 6-membered nitrogen heterocycle, such as, for example, pyrrolidine, piperidine, morpholine, thiomorpholine etc.

If the compounds of the formula I contain one or more acidic or basic groups or one or more basic heterocycles, the invention also includes the corresponding physiologically or toxicologically tolerable salts, in particular the pharmaceutically utilizable salts. Thus the compounds of the formula I which carry acidic groups, e.g. one or more COOH groups, for example as alkali metal salts, preferably sodium or potassium salts, or as alkaline earth metal salts, e.g. calcium or magnesium salts, or as ammonium salts, e.g. as salts with ammonia or organic amines or amino acids, can be used. Compounds of the formula I which carry one or more basic, i.e. protonatable, groups or contain one or more basic heterocyclic rings can also be used in the form of their physiologically tolerable acid addition salts with inorganic or organic acids, for example as hydrochlorides, phosphates, sulfates, methanesulfonates, acetates, lactates, maleates, fumarates, malates, gluconates etc. If the compounds of the formula I simultaneously contain acidic and basic groups in the molecule, the invention also includes internal salts, so-called betaines, in addition to the salt forms described. Salts can be obtained from the compounds of the formula I according to customary processes, for example by combination with an acid or base in a solvent or dispersant or alternatively from other salts by anion exchange.

If they are appropriately substituted, the compounds of the formula I can be present in stereoisomeric forms. If the compounds of the formula I contain one or more asymmetric centers, these independently of one another can have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus includes enantiomers, for example, in enantiomerically pure form, both as levo- and as dextrorotatory antipodes, and also in the form of mixtures of the two enantiomers in different ratios or in the form of racemates. If desired, the individual stereoisomers can be prepared by resolution of a mixture according to customary methods or, for example, by stereoselective synthesis. If mobile hydrogen atoms are present, the present invention also comprises all tautomeric forms of the compounds of the formula I.

The compounds of the formula I can be prepared by different chemical processes, which are likewise included in the present invention. Some typical routes are outlined in the reaction sequences designated below as schemes 1, 2, 3 and 4. The radicals R(1) to R(8) used here are in each case defined as indicated above, if not stated otherwise below.

Thus a compound of the formula I according to scheme 1 is obtained, for example, starting from diphenic anhydride derivatives of the formula II as precursors which are commercially obtainable or known from the literature. Reduction of the compounds II using sodium borohydride followed by reaction with potassium phthalimide as described in Tetrahedron 45 (1989) 1365-1376 yields the biphenylcarboxylic acids of the formula IV. By coupling with amines of the formula HNR(3)R(4) followed by hydrazinolysis of the phthalimide, the aminomethyl compounds of the formula VI are obtained, from which, by reaction with suitable derivatives of the formula R(1)-X, the compounds of the formula I according to the invention are obtained in which R(2) is hydrogen and R(1), R(3), R(4), R(5), R(6), R(7) and R(8) have the meanings indicated above. Subsequent alkylation using suitable alkylating agents of the formula R(2)Y, in which Y is a nucleofugic leaving group, e.g. Cl, Br or I, yields the corresponding compounds of the formula I in which R(2) is alkyl having 1 to 4 carbon atoms.

Alternatively, the biphenylcarboxylic acids of the formula IV can also be converted by hydrazinolysis to the aminocarboxylic acids of the formula VII which are then converted by reaction of the amino group with compounds of the formulae R(1)-X and R(2)-Y followed by amidation of the carboxylic acids with amines of the formula HNR(3)R(4) to give compounds of the formula I according to the invention (scheme 2).

In some cases, it can be useful to first prepare compounds of the formula Ia (scheme 3) in which R(9) is an easily removable radical, such as, for example, tert-butyl or benzyl, by one of the previously mentioned methods. After removal of the corresponding protective group, e.g. with trifluoroacetic acid for the Boc group or by catalytic hydrogenation for the benzyloxycarbonyl radical, the compounds of the formula IX are obtained, which can then in turn be converted into other compounds of the formula I according to the invention by reaction with compounds of the formula R(1)-X.

Another possibility for the preparation of compounds of the formula Ia consists in the palladium-catalyzed coupling of a phenyl bromide or iodide of the formula X with a phenylboronic acid of the formula XI (Suzuki coupling; scheme 4), which can be carried out, for example, in the presence of $Pd[(PPh)_3]_4$ as a catalyst, sodium carbonate as a base and 1,2-dimethoxyethane as a solvent. The compounds of the formula Ia can then be converted into other compounds of the formula I according to the invention as described above and in scheme 3.

The necessary boronic acids XI can be obtained from the compounds XII, in which Z represents hydrogen, bromine or iodine, by ortholithiation respectively metal-halogen exchange and subsequent reaction with boric acid trimethylate.

The abovementioned reactions of the compounds of the formulae VI, VII and IX with compounds of the formula R(1)-X correspond to the known conversion of an amine to a carboxamide, sulfonamide, carbamate, urea or thiourea derivative. The radical X here is a suitable nucleofugic leaving group, such as, for example, F, Cl, Br, imidazole, O-succinimide etc.

For the preparation of compounds of the formula I or VIII in which R(1) is C(O)OR(9), i.e. carbamates, compounds of the formula R(1)-X, for example, are used in which X is chlorine or O-succinimide, i.e. chloroformates or succinimidocarbonates.

For the preparation of compounds of the formula I or VIII in which R(1) is SO₂R(10), i.e. sulfonamides, as a rule compounds of the formula R(1)-X are used in which X is chlorine, i.e. sulfonyl chlorides.

For the preparation of compounds of the formula I or VIII in which R(1) is COR(11), i.e. carboxamides, compounds of the formula R(1)-X, for example, are used in which X is chlorine, imidazole or acetoxy, i.e. carbonyl chlorides, carboxylic acid imidazolides or mixed anhydrides. However, the free acids of the formula R(1)—OH can also be used in the presence of suitable condensing agents such as carbodiimides or uronium salts such as TOTU.

For the preparation of compounds of the formula I or VIII in which R(1) is CONR(12)R(13) or C(S)NR(12)R(13), i.e. ureas or thioureas, instead of the compounds of the formula R(1)-X it is also possible to use compounds of the formula R(12)N(=C=O), or R(12)N(=C=S), i.e. isocyanates or isothiocyanates.

The abovementioned reactions of the compounds of the formula IV or VIII with amines of the formula HNR(3)R(4) correspond to the known conversion of a carboxylic acid to a carboxamide. Numerous methods have been described in the literature for carrying out these reactions. They can be carried out particularly advantageously by activation of the carboxylic acid, e.g. with dicyclohexylcarbodiimide (DCC), if appropriate with addition of hydroxybenzotriazole (HOBT) or dimethylaminopyridine (DMAP), or with O—[(cyano (ethoxycarbonyl)methylene)amino]-1,1,3,3-tetramethyluronium tetrafluoroborate (TOTU). However, reactive acid derivatives can also be synthesized first according to known methods, e.g. acid chlorides by reaction of the carboxylic acids of the formula IV or VIII with inorganic acid halides, such as, for example, SOCl₂, or acid imidazolides by reaction with carbonyldiimidazole, which are then reacted with the amines of the formula HNR(3)R(4), if appropriate with the addition of an auxiliary base.

In all procedures, it may be appropriate to temporarily protect functional groups in the molecule in certain reaction steps. Such protective group techniques are familiar to the person skilled in the art. The choice of a protective group for groups under consideration and the processes for their introduction and removal are described in the literature and can if necessary be adapted to the individual case without difficulties.

Scheme 1:

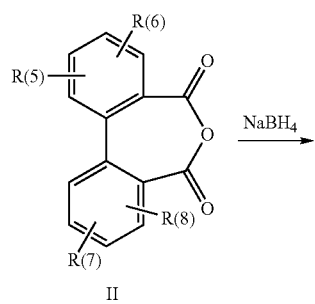

II

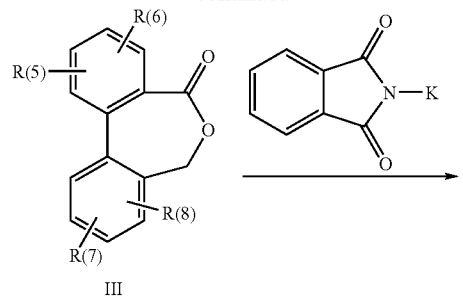

III

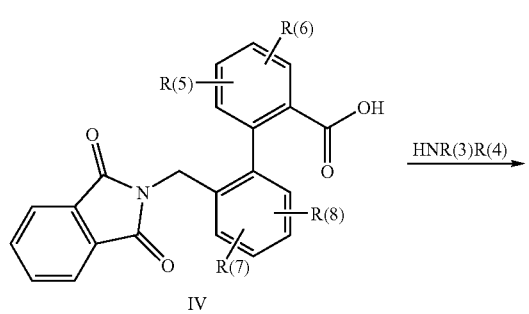

IV

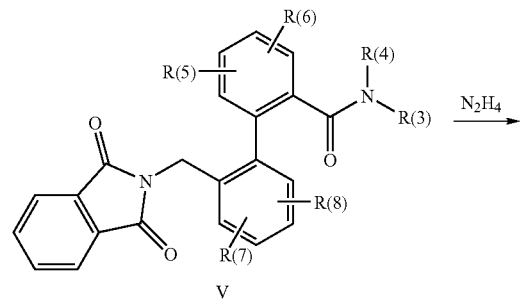

V

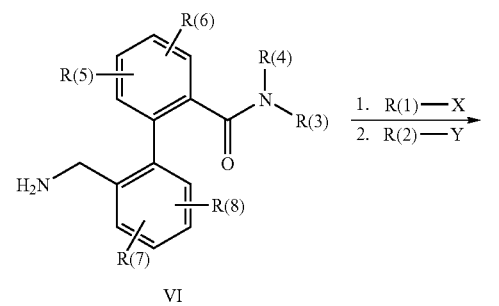

VI

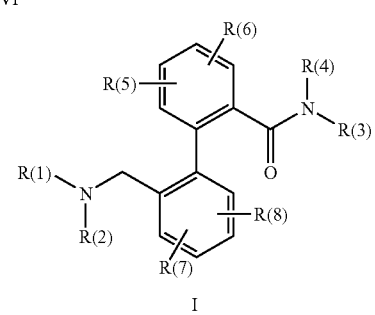

I

Scheme 2:
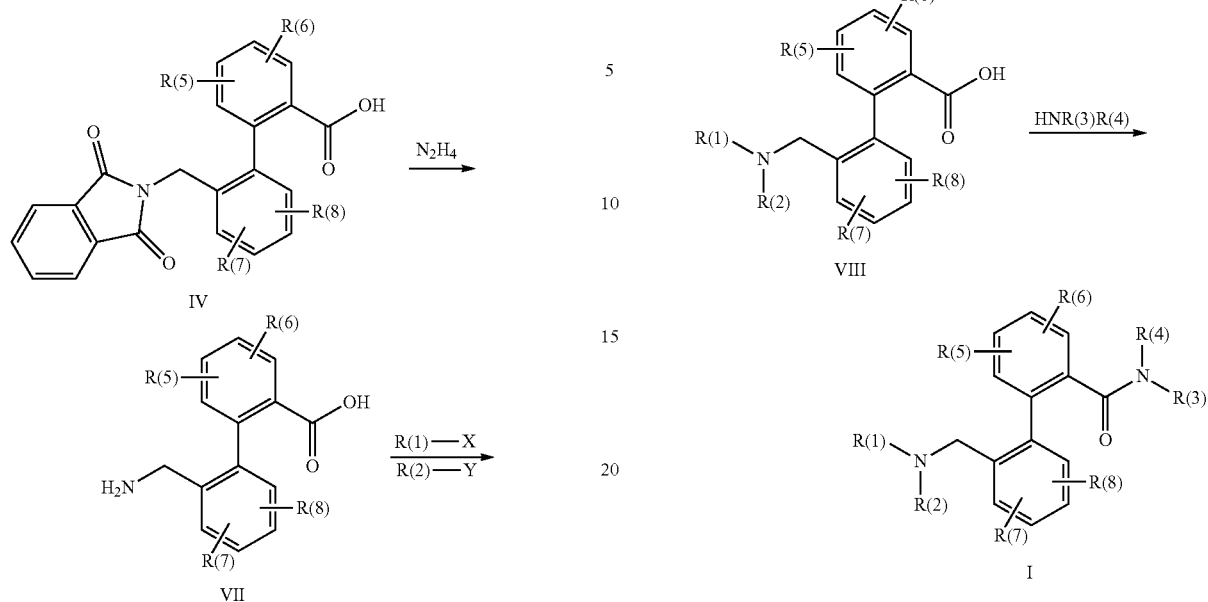
Scheme 3:
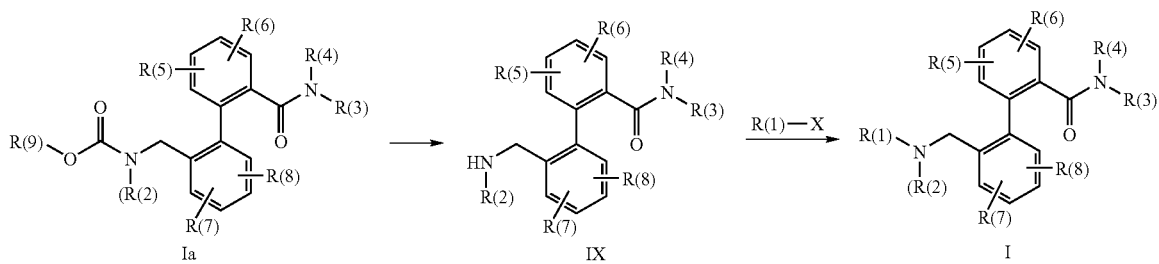
Scheme 4:
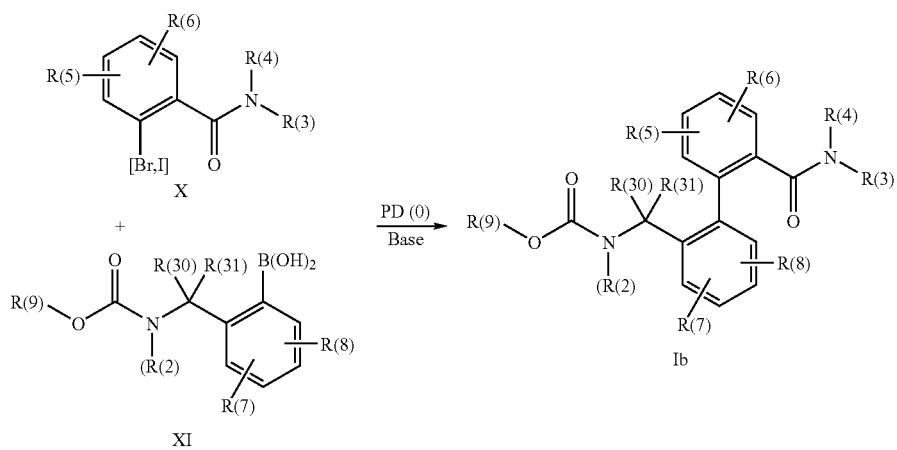

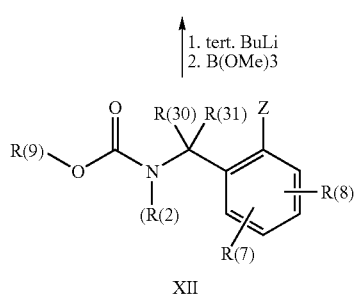

XII

The compounds of the formula I according to the invention and their physiologically tolerable salts can thus be used in animals, preferably in mammals, and in particular in humans, as pharmaceuticals on their own, in mixtures with one another or in the form of pharmaceutical preparations. The present invention also relates to the compounds of the formula I and their physiologically tolerable salts for use as pharmaceuticals, their use in the therapy and prophylaxis of the syndromes mentioned and their use for the production of medicaments therefor and of medicaments having $K^+$ channel-blocking action. The present invention furthermore relates to pharmaceutical preparations which, as active constituent, contain an efficacious dose of at least one compound of the formula I and/or of a physiologically tolerable salt thereof in addition to customary, pharmaceutically innocuous vehicles and excipients. The pharmaceutical preparations normally contain 0.1 to 90% by weight of the compounds of the formula I and/or their physiologically tolerable salts. The pharmaceutical preparations can be prepared in a manner known per se. To this end, the compounds of the formula I and/or their physiologically tolerable salts are brought, together with one or more solid or liquid pharmaceutical vehicles and/or excipients and, if desired, in combination with other pharmaceutical active compounds, into a suitable administration form or dose form, which can then be used as a pharmaceutical in human medicine or veterinary medicine.

Pharmaceuticals which contain compounds of the formula I according to the invention and/or their physiologically tolerable salts can be administered orally, parenterally, e.g. intravenously, rectally, by inhalation or topically, the preferred administration being dependent on the individual case, e.g. the particular form of the disease to be treated.

The person skilled in the art is familiar on the basis of his/her expert knowledge with which excipients are suitable for the desired pharmaceutical formulation. In addition to solvents, gel-forming agents, suppository bases, tablet excipients and other active compound carriers, it is possible to use, for example, antioxidants, dispersants, emulsifiers, antifoams, flavor corrigents, preservatives, solubilizers, agents for achieving a depot effect, buffer substances or colorants.

For the obtainment of an advantageous therapeutic action, the compounds of the formula I can also be combined with other pharmaceutical active compounds. Thus in the treatment of cardiovascular diseases advantageous combinations with substances having cardiovascular activity are possible. Possible combination partners of this type which are advantageous for cardiovascular disorders are, for example, other antiarrhythmics, i.e. class I, class II or class III antiarrhythmics, such as, for example, $IK_s$ or $IK_r$ channel blockers, e.g. dofetilide, or furthermore hypotensive substances such as ACE inhibitors (for example enalapril, captopril, ramipril), angiotensin antagonists, $K^+$ channel activators, and also alpha- and betareceptor blockers, but also sympathomimetic compounds and compounds having adrenergic activity, as well as $Na^+/H^+$ exchange inhibitors, calcium channel antagonists, phosphodiesterase inhibitors and other substances having a positive inotropic action, such as, for example, digitalis glycosides, or diuretics.

For an oral administration form, the active compounds are mixed with the additives suitable therefor, such as vehicles, stabilizers or inert diluents, and brought by the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular cornstarch. In this case, preparation can be carried out both as dry and as moist granules. Suitable oily vehicles or solvents are, for example, vegetable or animal oils, such as sunflower oil or cod-liver oil. Suitable solvents for aqueous or alcoholic solutions are, for example, water, ethanol or sugar solutions or mixtures thereof. Further excipients, also for other administration forms, are, for example, polyethylene glycols and polypropylene glycols.

For subcutaneous or intravenous administration, the active compounds, if desired with the substances customary therefor such as solubilizers, emulsifiers or further excipients, are brought into solution, suspension or emulsion. The compounds of the formula I and their physiologically tolerable salts can also be lyophilized and the lyophilizates obtained used, for example, for the production of injection or infusion preparations. Suitable solvents are, for example, water, physiological saline solution or alcohols, e.g. ethanol, propanol, glycerol, and in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also contain other pharmaceutical excipients such as surfactants, emulsifiers and stabilizers, and a propellant. Such a preparation contains the active compound customarily in a concentration of approximately 0.1 to 10, in particular of approximately 0.3 to 3, percent by weight.

The dose of the active compound of the formula I or of the physiologically tolerable salts thereof to be administered depends on the individual case and is to be adjusted to the conditions of the individual case as customary for an optimum action. Thus it depends, of course, on the frequency of administration and on the potency and duration of action of the compounds in each case employed for therapy or prophylaxis, but also on the nature and severity of the illness to be treated and on sex, age, weight and individual responsiveness of the human or animal to be treated and on whether treatment is acute or prophylactic. Customarily, the daily dose of a compound of the formula I on administration to a patient weighing approximately 75 kg is 0.001 mg/kg of body weight to 100 mg/kg of body weight, preferably 0.01 mg/kg of body weight to 20 mg/kg of body weight. The dose can be administered in the form of an individual dose or can be divided into two or more, e.g. 2, 3 or 4, individual doses. In particular in the treatment of acute cases of cardiac arrhythmias, for example in an intensive care unit, parenteral administration by injection or infusion, e.g. by an intravenous continuous infusion, can also be advantageous.

EXPERIMENTAL SECTION

List of Abbreviations

CDI Carbonyldiimidazole
DIC Diisopropylcarbodiimide
DMAP 4-Dimethylaminopyridine
DMF N,N-Dimethylformamide
EDAC N-Ethyl-N'-(3-dimethylaminopropyl)carbodiimide hydrochloride
EA Ethyl acetate
m.p. Melting point (if not stated otherwise the melting points of the unpurified crude products are stated; the melting points of the respective pure substances can definitely be markedly higher)
HOBT 1-Hydroxy-1H-benzotriazole
in vac. In vacuo
S Solvent
Me Methyl
RT Room temperature
THF Tetrahydrofuran
TOTU O-[(Cyano(ethoxycarbonyl)methylene)amino]-1,1,3,3-tetramethyluronium tetrafluoroborate Precursor 1: 7H-Dibenzo[c,e]oxepin-5-one 9.0 g (0.24 mol) of sodium borohydride were added in portions at 5° C. in the course of 10 min to a suspension of 50.0 g (0.22 mol) of diphenic anhydride in 220 ml of DMF. After stirring at RT for 1 h, the reaction mixture was poured onto 220 ml of 6 M hydrochloric acid, diluted with 750 ml of water and stirred for 2 h. The deposited precipitate was filtered off with suction and 35.0 g of 7H-dibenzo[c,e]oxepin-5-one were obtained; m.p. 131° C.

Precursor 2: 2'-Phthalimidomethylbiphenyl-2-carboxylic acid

A mixture of 35 g (0.17 mol) of 7H-dibenzo[c,e]oxepin-5-one and 30.8 g (0.17 mol) of potassium phthalimide in 330 ml of DMF was heated at 170° C. for 18 h. After cooling, the deposited precipitate was filtered off with suction and introduced into 160 ml of glacial acetic acid. After stirring for 1 h, the mixture was diluted with 650 ml of ice water and the deposited product was filtered off with suction and dried in vacuo. 44.8 g of 2'-phthalimidomethylbiphenyl-2-carboxylic acid were obtained; m.p. 198° C.

Precursor 3: 2'-Aminomethylbiphenyl-2-carboxylic acid

A suspension of 10.0 g (28 mmol) of 2'-phthalimidomethylbiphenyl-2-carboxylic acid in 450 ml of methanol was treated with 20 ml of hydrazine hydrate and heated at 40° C. for 1.5 h. The reaction mixture was concentrated and the residue was taken up in 250 ml of methylene chloride. After filtering off undissolved 2,3-dihydrophthalazine-1,4-dione, the mother liquor was concentrated and 4.8 g of 2'-aminomethylbiphenyl-2-carboxylic acid were obtained.

General Procedure for the Synthesis of Mixed Succinimidocarbonates from Alcohols (Precursors 4 a-4 k)

5.0 g (19.5 mmol) of disuccinimidyl carbonate are added in portions at 0° C. to a solution of 19.5 mmol of the appropriate alcohol and 1.2 g (9.8 mmol) of DMAP in 30 ml of methylene chloride and 30 ml of acetonitrile. After stirring at RT for 2.5 to 10 h, 25 ml of water are added and the organic phase is washed a further 2 times with water. After drying and concentration, the corresponding succinimidocarbonates are obtained, usually as crystalline solids.

Precursor 4 a

According to the general procedure, 3.2 g of 4-fluorobenzyl N-succinimidocarbonate were obtained; m.p. 89° C. (ether).

Precursor 4 b

From 11.7 mmol of 4-trifluoromethylbenzyl alcohol, corresponding to the general procedure 2.3 g of 4-trifluoromethylbenzyl N-succinimidocarbonate were obtained; m.p. 102° C. (ether).

Precursor 4 c

From 10.5 mmol of a-methyl-4-(trifluoromethyl)benzyl alcohol, corresponding to the general procedure 1.6 g of α-methyl-4-(trifluoromethyl)benzyl N-succinimidocarbonate were obtained; m.p. 115° C. (ether).

Precursor 4 d

From 19.5 mmol of 4,4,4-trifluorobutanol, corresponding to the general procedure 4.0 g of 4,4,4-trifluorobutyl N-succinimidocarbonate were obtained; m.p. 72° C. (ether).

Precursor 4 e

From 26.3 mmol of a-methyl-3-(trifluoromethyl)benzyl alcohol, corresponding to the general procedure 5.1 g of α-methyl-3-(trifluoromethyl)benzyl N-succinimidocarbonate were obtained; m.p. 77° C. (ether).

Precursor 4 f

From 31.6 mmol of α-methyl-2,6-difluorobenzyl alcohol, corresponding to the general procedure 1.6 g of α-methyl-2,6-difluorobenzyl N-succinimidocarbonate were obtained; m.p. 108° C. (ether).

Precursor 4 g

From 25 mmol of α-methyl-2-(trifluoromethyl)benzyl alcohol, corresponding to the general procedure 3.5 g of α-methyl-2-(trifluoromethyl)benzyl N-succinimidocarbonate were obtained.

Precursor 4 h

From 25 mmol of (S)-1-phenylethanol, corresponding to the general procedure 3.5 g of (S)-α-methylbenzyl N-succinimidocarbonate were obtained.

Precursor 4 i

From 25 mmol of (R)-1-phenylethanol, corresponding to the general procedure 3.5 g of (R)-α-methylbenzyl N-succinimidocarbonate were obtained.

Precursor 4 j

From 25 mmol of α-methyl-4-fluorobenzyl alcohol, corresponding to the general procedure 4.3 g of α-methyl-4-fluorobenzyl N-succinimidocarbonate were obtained.

Precursor 4 k

From 9.8 mmol of (S)-1-phenyl-1-butanol, corresponding to the general procedure 1.7 g of (S)-α-propylbenzyl N-succinimidocarbonate were obtained.

Precursor 5 a: 2'-Aminomethylbiphenyl-2-carboxylic Acid phenethylamide

From 2'-phthalimidomethylbiphenyl-2-carboxylic acid (precursor 2), after activation with CDI and reaction with phenethylamine, 2'-phthalimidomethylbiphenyl-2-carboxylic acid phenethylamide was obtained; m.p. 156° C.

5.0 g (10.9 mmol) of the product were dissolved in 200 ml of methanol and treated with 5 ml of hydrazine hydrate. After stirring at 40° C. for 1 h, the reaction mixture was concentrated and the residue was taken up in methylene chloride. After filtering off the 2,3-dihydrophthalazine-1,4-dione formed, the mother liquor was concentrated and the residue was purified by flash chromatography using methylene chloride/methanol 20:1. 3 g of 2'-aminomethylbiphenyl-2-carboxylic acid phenethylamide were obtained.

Precursor 5 b: 2'-Aminomethylbiphenyl-2-carboxylic Acid Benzylamide

From 2'-phthalimidomethylbiphenyl-2-carboxylic acid (precursor 2), after conversion into the acid chloride using thionyl chloride and reaction with benzylamine, 2'-phthalimidomethylbiphenyl-2-carboxylic acid benzylamide was obtained. 1.2 g (2.7 mmol) of the product were dissolved in 55 ml of methanol and treated with 1.35 ml of hydrazine hydrate. After stirring at 40° C. for 1 h, the reaction mixture was concentrated and the residue was taken up in methylene chloride. After filtering off the 2,3-dihydrophthalazine-1,4-dione formed, the mother liquor was concentrated and the residue was purified by flash chromatography using methylene chloride/methanol 30:1. 0.49 g of 2'-aminomethylbiphenyl-2-carboxylic acid benzylamide was obtained.

Precursor 5 c: 2'-Aminomethylbiphenyl-2-carboxylic Acid Isopentylamide

From 3 g (8.4 mmol) of 2'-phthalimidomethylbiphenyl-2-carboxylic acid (precursor 2), by reaction with isopentylamine in the presence of HOBT and DIC, 3.2 g of 2'-phthalimidomethylbiphenyl-2-carboxylic acid isopentylamide were obtained; m.p. 169° C. The product was dissolved in 100 ml of methanol and treated with 5 ml of hydrazine hydrate. After stirring at 40° C. for 1 h, the cooled reaction mixture was filtered. The filtrate was concentrated and the residue was taken up in methylene chloride. After washing with water, drying and concentrating, 1.8 g of 2'-aminomethylbiphenyl-2-carboxylic acid isopentylamide were obtained.

Precursor 5 d

2'-Aminomethylbiphenyl-2-carboxylic acid 2-(2-pyridyl)ethylamide

From 10 g (28 mmol) of 2'-phthalimidomethylbiphenyl-2-carboxylic acid (precursor 2), by reaction with 2-(2-pyridyl)ethylamine in the presence of HOBT and DIC, 13 g of 2'-phthalimidomethylbiphenyl-2-carboxylic acid 2-(2-pyridyl)ethylamide were obtained; m.p. 155° C. The product was suspended in 300 ml of methanol and treated with 20 ml of hydrazine hydrate. After stirring at 40° C. for 1 h, the cooled reaction mixture was filtered. The filtrate was concentrated and the residue was taken up in EA. The product was extracted into the aqueous phase 2 times using 2 M hydrochloric acid. The aqueous phase was then rendered alkaline with potassium carbonate and extracted 2 times with EA. After washing with water, drying and concentrating, 7.3 g of 2'-aminomethylbiphenyl-2-carboxylic acid 2-(2-pyridyl)ethylamide were obtained.

Precursor 6: 2'-(Benzyloxycarbonylaminomethyl)biphenyl-2-carboxylic Acid 500 mg (2 mmol) of benzyl N-succinimidocarbonate dissolved in 2.5 ml of dioxane were added dropwise at 0° C. to a solution of 455 mg (2 mmol) of 2'-aminomethylbiphenyl-2-carboxylic acid (precursor 3) and 336 mg (4 mmol) of sodium hydrogencarbonate in 5 ml of dioxane and 5 ml of water. After stirring at RT for 4 h, the mixture was concentrated in vacuo, diluted with water, acidified and extracted with ethyl acetate. 590 mg of 2'-(benzyloxycarbonylaminomethyl)biphenyl-2-carboxylic acid were obtained.

Precursor 7: 2'-(tert-Butoxycarbonylaminomethyl)biphenyl-2-carboxylic Acid 65 ml of 1 M sodium hydroxide solution were added to a solution of 12.0 g (53 mmol) of 2'-aminomethylbiphenyl-2-carboxylic acid (precursor 3) in 130 ml of 1,4-dioxane and 65 ml of water and, after complete dissolution, 12.6 g (58 mmol) of di-tert-butyl dicarbonate were added. After stirring at RT for 2 h, the mixture was concentrated in vacuo, diluted with water and extracted 2 times with methylene chloride. The aqueous phase was acidified with 1 M potassium hydrogensulfate solution and extracted with ethyl acetate. After extensive concentration, addition of n-heptane and allowing to stand overnight, the product precipitated and 7.6 g of 2'-(tertbutoxycarbonylaminomethyl)biphenyl-2-carboxylic acid were obtained;
m.p. 136° C.

General Procedure for the Removal of the Boc Protective Group:

The n-Boc-protected aminomethylbiphenyl derivative (1 g to 10 ml of solution) was added to a solution of trifluoroacetic acid in dichloromethane (30% strength). The mixture was stirred at room temperature for 30 minutes and the solvent was then removed in vacuo on a rotary evaporator. The residue was taken up in ethyl acetate and washed with saturated sodium hydrogencarbonate solution. The organic phase was dried over magnesium sulfate, the solvent was removed in vacuo and the corresponding 2'-aminomethylbiphenyl-2-carboxamides were obtained.

Precursor 8 a: 2'-Aminomethylbiphenyl-2-carboxylic Acid (2,4-difluorobenzyl)amide The compound was obtained from the Boc-protected compound (Example 8 c) according to the general procedure. Alternatively, the compound can also be isolated directly as the trifluoroacetate and reacted further.

Further Precursors 8

The corresponding amines were analogously liberated from the Boc-protected compounds of Examples 8 d-8 o and 10 a-10 o.

General Procedure for the Reaction of aminomethylbiphenyls with succinimidocarbonates to Give Carbamates (Examples 1 a to 1 u)

0.45 mmol of the respective succinimidocarbonate dissolved in 2 ml of dioxane is slowly added dropwise to a solution of 0.45 mmol of the respective 2'-aminomethylbiphenyl and 38 mg (0.45 mmol) of sodium hydrogencarbonate in 2 ml of dioxane and 2 ml of water. The mixture is stirred at RT for 2 to 12 h, concentrated, diluted with water and extracted with EA, and the organic phase is washed with water. After drying and concentration, the corresponding carbamates are obtained.

Example 1 a

2'-(4-Trifluoromethylbenzyloxycarbonylaminomethyl)biphenyl-2-carboxylic acid phenethylamide

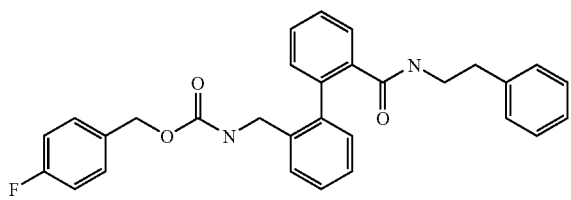

From 0.45 mmol of 2'-aminomethylbiphenyl-2-carboxylic acid phenethylamide and 4-trifluoromethylbenzyl N succinimidocarbonate (precursor 4 b), according to the general working procedure 226 mg of 2'-(4-trifluoromethylbenzyloxycarbonylaminomethyl)biphenyl-2-carboxylic acid phenethylamide were obtained. MS (ES+): m/e=533 (M+1).

Example 1 b

2'-(Benzyloxycarbonylaminomethyl)biphenyl-2-carboxylic acid phenethylamide

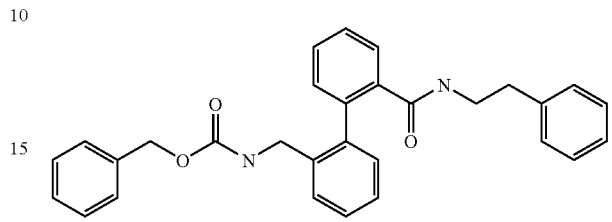

From 0.3 mmol of 2'-aminomethylbiphenyl-2-carboxylic acid phenethylamide and benzyl N-succinimidocarbonate, according to the general working procedure 66 mg of 2'-(benzyloxycarbonylaminomethyl)biphenyl-2-carboxylic acid phenethylamide were obtained as an oil. MS (ES+): m/e=456 (M+1).

Example 1c

2'-(Methylsulfonylethyloxycarbonylaminomethyl)biphenyl-2-carboxylic acid phenethylamide

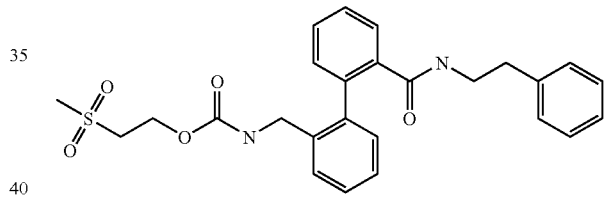

From 0.45 mmol of 2'-aminomethylbiphenyl-2-carboxylic acid phenethylamide (precursor 5 a) and methylsulfonylethyl N-succinimidocarbonate, according to the general working procedure 164 mg of 2'-(methylsulfonylethyloxycarbonylaminomethyl)biphenyl-2-carboxylic acid phenethylamide were obtained as an oil. MS (ES+): m/e=481 (M+1).

Example 1 d

2'-(4-Trifluoromethylbenzyloxycarbonylaminomethyl)biphenyl-2-carboxylic acid 2-(2-pyridyl)ethylamide

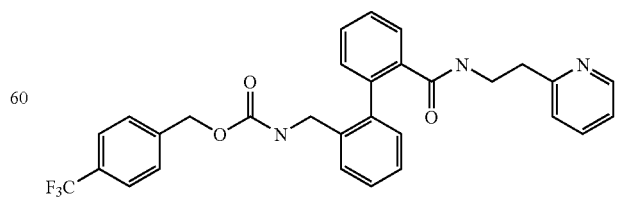

From 0.3 mmol of 2'-aminomethylbiphenyl-2-carboxylic acid 2-(2-pyridyl)ethylamide (precursor 5 d) and 4-trifluoromethylbenzyl N-succinimidocarbonate (precursor 4 b), according to the general working procedure 170 mg of 2'-(4-trifluoromethylbenzyloxycarbonylaminomethyl)biphenyl-2-carboxylic acid 2-(2-pyridyl)ethylamide were obtained. MS (ES+): m/e=534 (M+1).

Example 1 e

2'-(4-Fluorobenzyloxycarbonylaminomethyl)biphenyl-2-carboxylic acid 2-(2-pyridyl)ethylamide

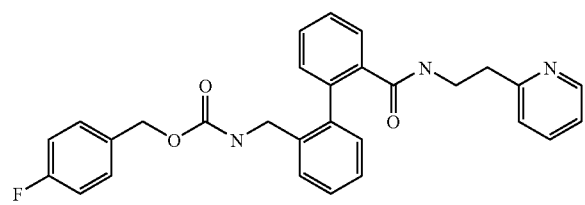

From 0.3 mmol of 2'-aminomethylbiphenyl-2-carboxylic acid 2-(2-pyridyl)ethylamide (precursor 5 d) and 4-fluorobenzyl N-succinimidocarbonate (precursor 4 a), according to the general working procedure 150 mg of 2'-(4-fluorobenzyloxycarbonylaminomethyl)biphenyl-2-carboxylic acid 2-(2-pyridyl)ethylamide were obtained. MS (ES+): m/e=484 (M+1).

Example 1 f (±)-2'-(α-Methyl-4-(trifluoromethyl)benzyloxycarbonylaminomethyl)biphenyl-2-carboxylic acid 2-(2-pyridyl)ethylamide

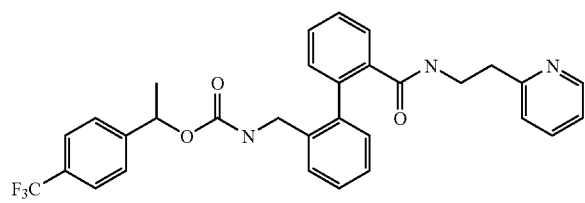

From 0.3 mmol of 2'-aminomethylbiphenyl-2-carboxylic acid 2-(2-pyridyl)ethylamide (precursor 5 d) and α-methyl-4-(trifluoromethyl)benzyl N-succinimidocarbonate (precursor 4 c), according to the general working procedure 170 mg of 2'-α-methyl-4-(trifluoromethyl)benzyloxycarbonylaminomethyl)biphenyl-2-carboxylic acid 2-(2-pyridyl)ethylamide were obtained as a racemate. MS (ES+): m/e=548 (M+1).

Example 1 g (S)-2'-(α-Methyl-4-(trifluoromethyl)benzyloxycarbonylaminomethyl)biphenyl-2-carboxylic acid 2-(2-pyridyl)ethylamide

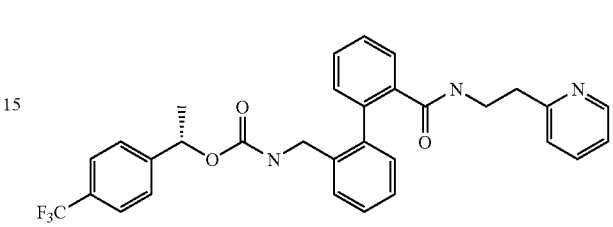

The S enantiomer was obtained from the corresponding racemate (Example 1 f) by preparative HPLC on a Chiralpak AD 250×4.6 column using n-hexane/ethanol/isopropanol (10:1:1, 0.3% each of trifluoroacetic acid/diethylamine) as solvent.

Example 1 h (R)-2'-(α-Methyl-4-(trifluoromethyl)benzyloxycarbonylaminomethyl)biphenyl-2-carboxylic acid 2-(2-pyridyl)ethylamide

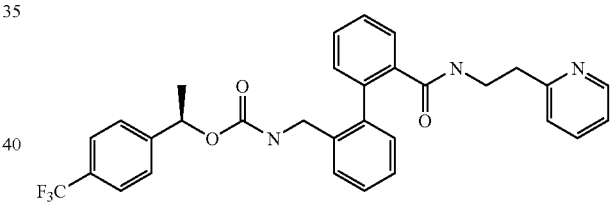

The R enantiomer was obtained from the corresponding racemate (Example 1 f) by preparative HPLC on a Chiralpak AD 250×4.6 column using n-hexane/ethanol/isopropanol (10:1:1, 0.3% each of trifluoroacetic acid/diethylamine) as solvent.

Example 1 i

2'-(4,4,4-Trifluorobutyloxycarbonylaminomethyl)biphenyl-2-carboxylic acid 2-(2-pyridyl)ethylamide

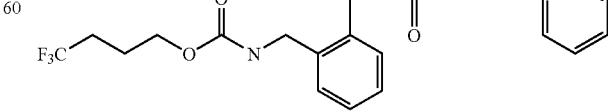

From 0.3 mmol of 2'-aminomethylbiphenyl-2-carboxylic acid 2-(2-pyridyl)ethylamide (precursor 5 d) and 4,4,4-trifluorobutyl N-succinimidocarbonate (precursor 4 d), according to the general working procedure 140 mg of 2' (4,4,4-trifluorobutyloxycarbonylaminomethyl)biphenyl-2-carboxylic acid 2-(2-pyridyl)ethylamide were obtained. MS (ES+): m/e=486 (M+1).

Example 1 j (S)-2'-(α-Methylbenzyloxycarbonylaminomethyl)biphenyl-2-carboxylic acid 2-(2-pyridyl)-ethylamide

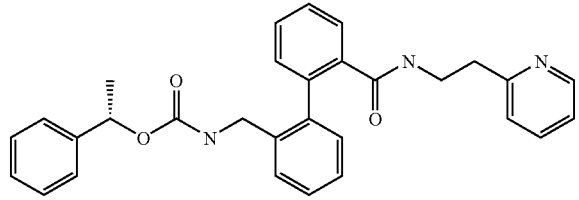

From 0.3 mmol of 2'-aminomethylbiphenyl-2-carboxylic acid 2-(2-pyridyl)ethylamide (precursor 5 d) and (S)-α-methylbenzyl N-succinimidocarbonate (precursor 4 h), according to the general working procedure 60 mg of (S)-2'-α-methylbenzyloxycarbonylaminomethyl)biphenyl-2-carboxylic acid 2-(2-pyridyl)ethylamide were obtained. MS (ES+): m/e=480 (M+1).

Example 1 k (R)-2'-(α-Methylbenzyloxycarbonylaminomethyl)biphenyl-2-carboxylic acid 2-(2-pyridyl)ethylamide

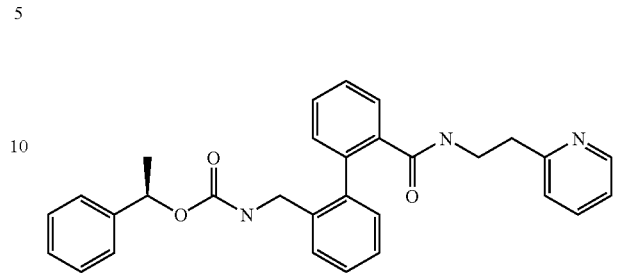

From 0.3 mmol of 2'-aminomethylbiphenyl-2-carboxylic acid 2-(2-pyridyl)ethylamide (precursor 5 d) and (R)-α-methylbenzyl N-succinimidocarbonate (precursor 4 i), according to the general working procedure 60 mg of (R)-2'-α-methylbenzyloxycarbonylaminomethyl)biphenyl-2-carboxylic acid 2-(2-pyridyl)ethylamide were obtained. MS (ES+): m/e=480 (M+1).

Examples 1 l-1 u

The following compounds were obtained from the respective precursors according to the general working procedure and analogously to Examples 1 a-1 k:

| Example No. | Precursors | Structure | MS (ES+): m/e = |
|---|---|---|---|
| 1 l | 5 d + 4 g | 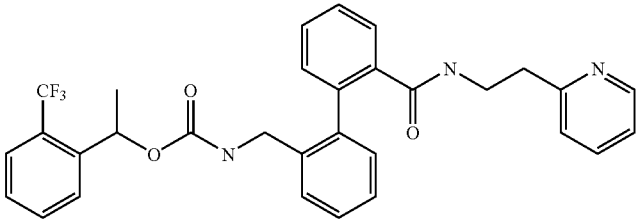 | 548 |
| 1 m | 5 d + 4 e | 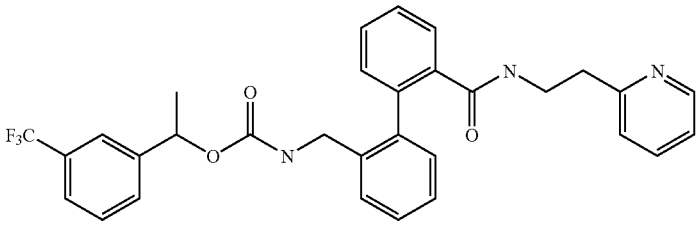 | 548 |
| 1 n | 5 d + 4 f | 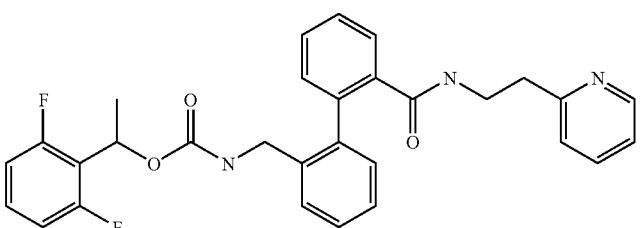 | 516 |

-continued

| Example No. | Precursors | Structure | MS (ES+): m/e = |
|---|---|---|---|
| 1 o | 8 a + 4 i | 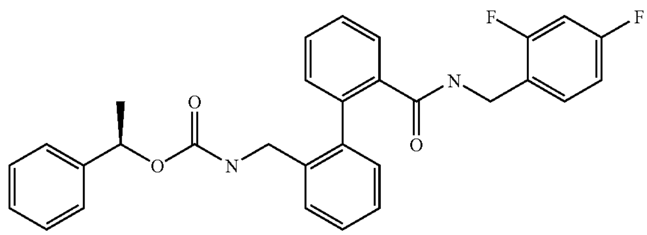 | 501 |
| 1 p | 8 a + 4 c | 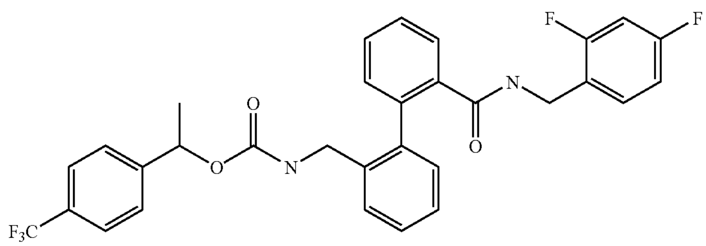 | 569 |
| 1 q | 8 a + 4 k | 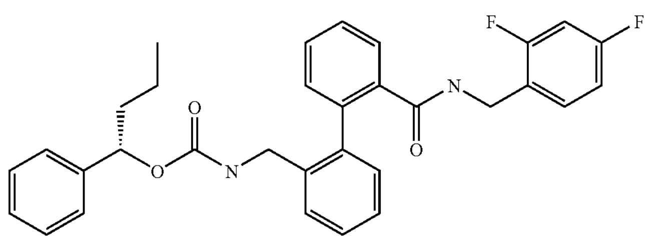 | 529 |
| 1 r | 5 d + 4 k | 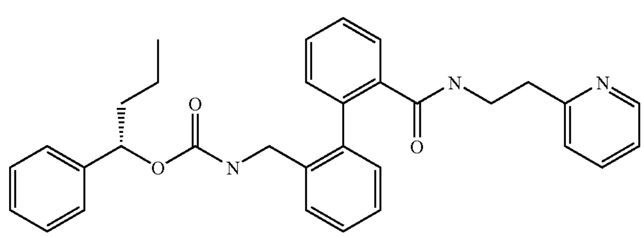 | 508 |
| 1 s | 8 a + 4 a | 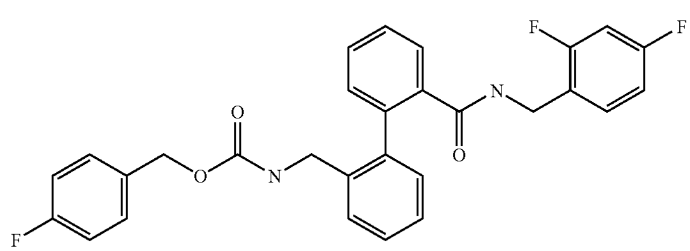 | 505 (m.p. 104° C.) |
| 1 t | 8 a + 4 d | 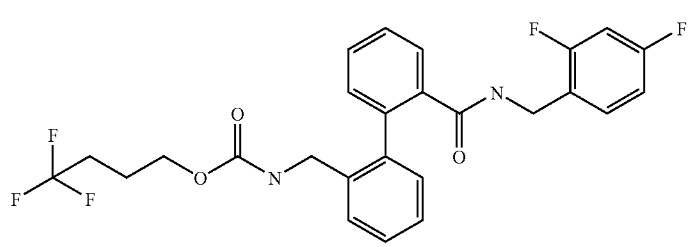 | 507 (m.p. 111° C.) |

| Example No. | Precursors | Structure | MS (ES+): m/e = |
|---|---|---|---|
| 1 u | | 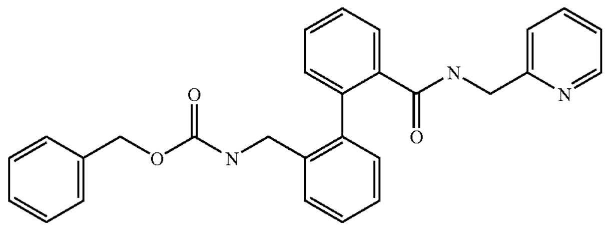 | 452 |

-continued

General Procedure for the Reaction of Aminomethylbiphenyls with Chloroformic Acid Esters to Give Carbamates (Examples 2 a to 2 m):

0.32 mmol of the respective chloroformic acid ester dissolved in 1 ml of methylene chloride is slowly added dropwise at 5° C. to a solution of 0.3 mmol of the respective 2'-aminomethylbiphenyl and 37 mg (0.36 mmol) of triethylamine in 6 ml of methylene chloride. The mixture is stirred at RT overnight, poured onto water and the organic phase is washed once more with water. After concentration, the residue is purified by flash chromatography.

Example 2 a

2'-(Butoxycarbonylaminomethyl)biphenyl-2-carboxylic acid 2-(2-pyridyl)ethylamide

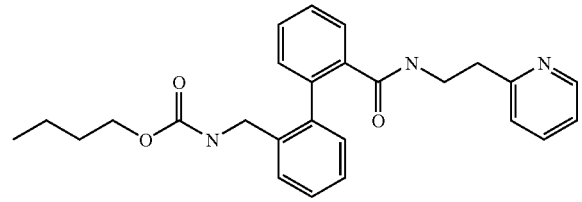

From 0.3 mmol of 2'-aminomethylbiphenyl-2-carboxylic acid 2-(2-pyridyl)ethylamide (precursor 5 d) and butyl chloroformate, according to the general working procedure 69 mg of 2'-(butoxycarbonylaminomethyl)biphenyl-2-carboxylic acid 2-(2-pyridyl)ethylamide were obtained as an oil. MS (ES+): m/e=432 (M+1).

Example 2 b

2'-(Benzyloxycarbonylaminomethyl)biphenyl-2-carboxylic acid (3-methylbutyl)amide

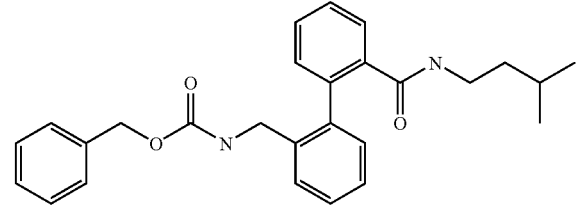

From 0.27 mmol of 2'-aminomethylbiphenyl-2-carboxylic acid (3-methylbutyl)amide (precursor 5 c) and benzyl chloroformate, according to the general working procedure 44 mg of 2'-(benzyloxycarbonylaminomethyl)biphenyl-2-carboxylic acid (3-methylbutyl)amide were obtained; m.p. 112° C. MS (ES+): m/e=431 (M+1).

Example 2 c

2'-(Benzyloxycarbonylaminomethyl)biphenyl-2-carboxylic acid 2-(2-pyridyl)ethylamide

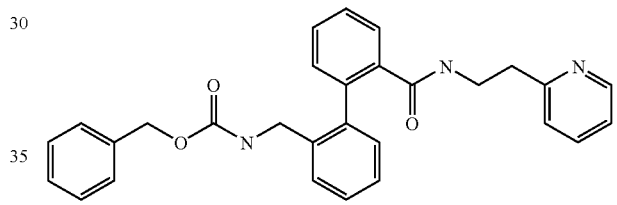

From 0.24 mmol of 2'-aminomethylbiphenyl-2-carboxylic acid 2-(2-pyridyl)-ethylamide (precursor 5 d) and benzyl chloroformate, according to the general working procedure 59 mg of 2'-(benzyloxycarbonylaminomethyl)-biphenyl-2-carboxylic acid 2-(2-pyridyl)ethylamide were obtained; m.p. 140° C. (heptane/EA). MS (ES+): m/e=466 (M+1).

Example 2 d

2'-(Butoxycarbonylaminomethyl)biphenyl-2-carboxylic acid (3-methylbutyl)amide

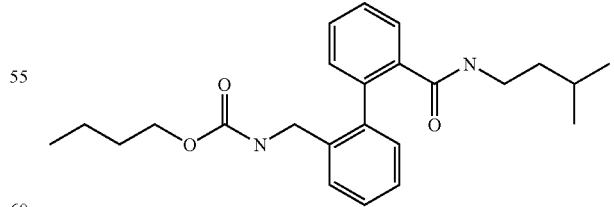

From 0.34 mmol of 2'-aminomethylbiphenyl-2-carboxylic acid (3-methylbutyl)amide (precursor 5 c) and butyl chloroformate, according to the general working procedure 66 mg of 2'-(butoxycarbonylaminomethyl)biphenyl-2-carboxylic acid (3-methylbutyl)amide were obtained as a resin.
MS (ES+): m/e=397 (M+1).

Example 2 e

2'-(2-Chlorobenzyloxycarbonylaminomethyl)biphenyl-2-carboxylic acid (3-methylbutyl)amide

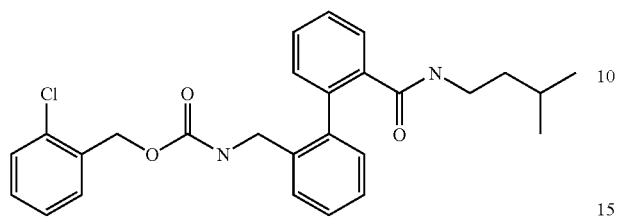

From 0.34 mmol of 2'-aminomethylbiphenyl-2-carboxylic acid (3-methylbutyl)amide (precursor 5 c) and 2-chlorobenzyl chloroformate, according to the general working procedure 75 mg of 2'-( 2-chlorobenzyloxycarbonylaminomethyl) biphenyl-2-carboxylic acid (3-methylbutyl)amide were obtained as a resin. MS (ES+): m/e=465 (M+1).

Example 2 f

2'-(Methoxycarbonylaminomethyl)biphenyl-2-carboxylic acid (3-methylbutyl)amide

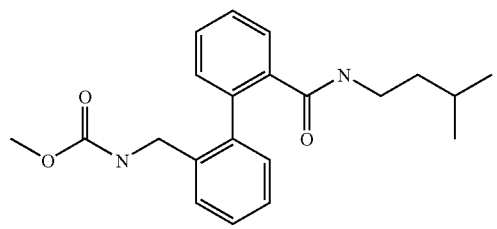

From 0.34 mmol of 2'-aminomethylbiphenyl-2-carboxylic acid (3-methylbutyl)amide (precursor 5 c) and methyl chloroformate, according to the general working procedure followed by extraction with EA and purification by flash chromatography 29 mg of 2'-(methoxycarbonylaminomethyl) biphenyl-2-carboxylic acid (3-methylbutyl)amide were obtained as a resin.
MS (ES+): m/e=355 (M+1).

Example 2 g

2'-(Phenoxycarbonylaminomethyl)biphenyl-2-carboxylic acid (3-methylbutyl)amide

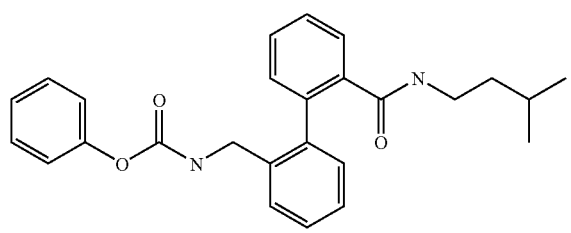

From 0.34 mmol of 2'-aminomethylbiphenyl-2-carboxylic acid ( 3-methylbutyl)amide (precursor 5 c) and phenyl chloroformate, according to the general working procedure followed by extraction with EA and purification by flash chromatography 55 mg of 2'-(phenoxycarbonylaminomethyl) biphenyl-2-carboxylic acid (3-methylbutyl)amide were obtained as a resin. MS (ES+): m/e=417 (M+1).

Example 2 h

2'-(4-Carbomethoxyphenoxycarbonylaminomethyl) biphenyl-2-carboxylic acid 3-methylbutyl)amide

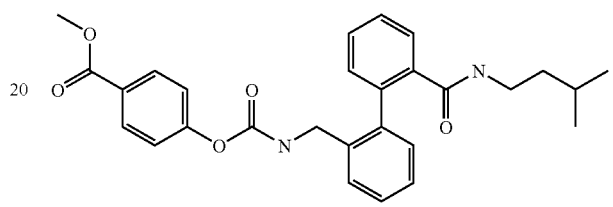

From 0.34 mmol of 2'-aminomethylbiphenyl-2-carboxylic acid (3-methylbutyl)amide (precursor 5 c) and (4-carbomethoxy)-phenyl chloroformate, according to the general working procedure followed by extraction with EA and purification by flash chromatography 77 mg of 2'-(4-carbomethoxyphenoxycarbonylaminomethyl)biphenyl-2-carboxylic acid (3-methylbutyl)amide were obtained as a resin. MS (ES+): m/e=475 (M+1).

Example 2 i

2'-(2,2-Dimethylpropoxycarbonylaminomethyl)biphenyl-2-carboxylic acid phenethylamide

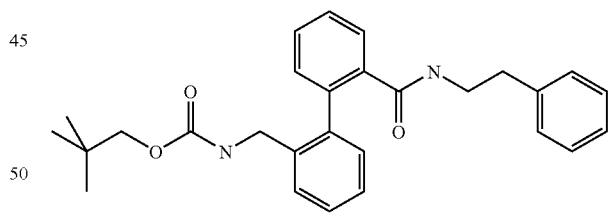

From 0.45 mmol of 2'-aminomethylbiphenyl-2-carboxylic acid phenethylamide (precursor 5 a) and neopentyl chloroformate, according to the general working procedure followed by extraction with EA and purification by flash chromatography 156 mg of 2'-(2,2-dimethylpropoxycarbonylaminomethyl)biphenyl-2-carboxylic acid phenethylamide were obtained.
MS (ES+): m/e=445 (M+1).

Examples 2 j-2 m

The following compounds were obtained analogously to Examples 2 a-2 i:

| Example No. | Structure | MS (ES+): m/e = | M.p. |
|---|---|---|---|
| 2 j | 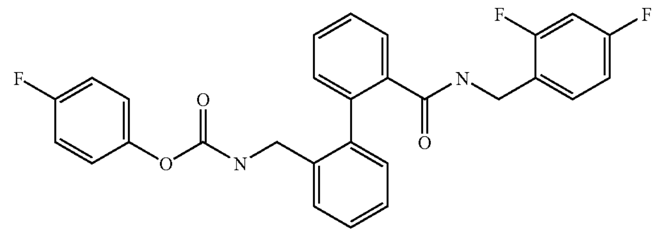 | 491 | |
| 2 k | 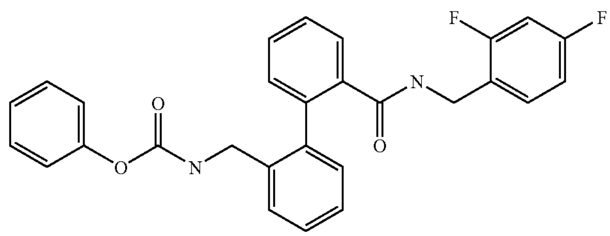 | 473 | 107 |
| 2 l | 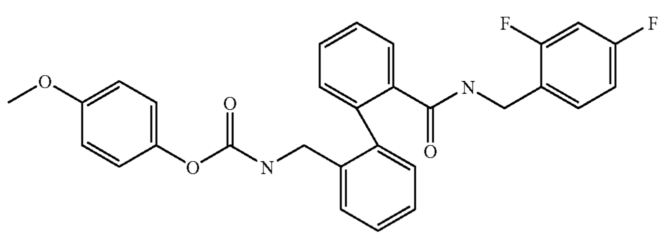 | 503 | 123 |
| 2 m | 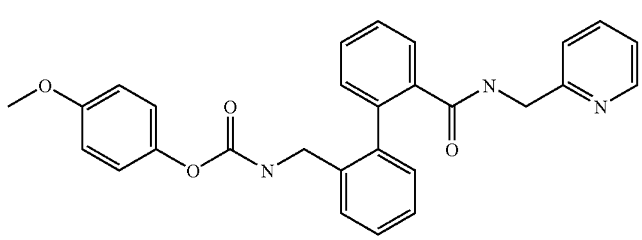 | 482 | |

General Procedure for the Reaction of Aminomethylbiphenyls with Sulfonyl Chlorides to give Sulfonamides (Examples 3 a to 3 t):

0.66 mmol of the respective sulfonyl chloride is slowly added dropwise at 0° C. to a solution of 0.61 mmol of the respective 2'-aminomethylbiphenyl and 74 mg (0.73 mmol) of triethylamine in 5 ml of methylene chloride. After stirring at RT for 12 h, the reaction mixture is concentrated in vacuo, the residue is stirred with 25 ml of water for 2 h and the crystallized product is filtered off with suction.

Example 3 a 2'-(3-Trifluoromethylphenylsulfonylaminomethyl)biphenyl-2-carboxylic acid phenethylamide

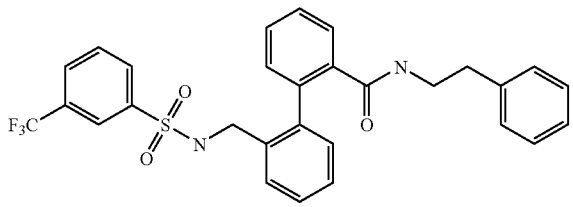

From 0.61 mmol of 2'-aminomethylbiphenyl-2-carboxylic acid phenethylamide (precursor 5 a) and 3-trifluoromethylphenylsulfonyl chloride, according to the general working procedure 272 mg of 2'-(3-trifluoromethylphenylsulfonylaminomethyl)biphenyl-2-carboxylic acid phenethylamide were obtained; m.p. 145° C. MS (ES+): m/e=539 (M+1).

Example 3 b

2'-(4-Acetylphenylsulfonylaminomethyl)biphenyl-2-carboxylic acid phenethylamide

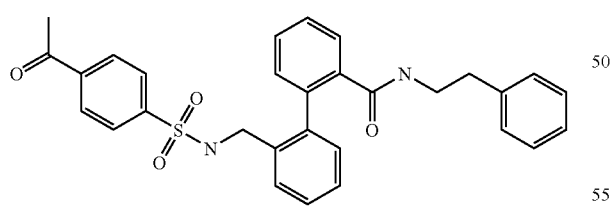

From 0.61 mmol of 2'-aminomethylbiphenyl-2-carboxylic acid phenethylamide (precursor 5 a) and 4-acetylphenylsulfonyl chloride, according to the general working procedure 258 mg of 2'-(4-acetylphenylsulfonylaminomethyl)biphenyl-2-carboxylic acid phenethylamide were obtained;

m.p. 145° C. MS (ES+): m/e=513 (M+1).

Example 3 c

2'-(3-Nitrophenylsulfonylaminomethyl)biphenyl-2-carboxylic acid phenethylamide

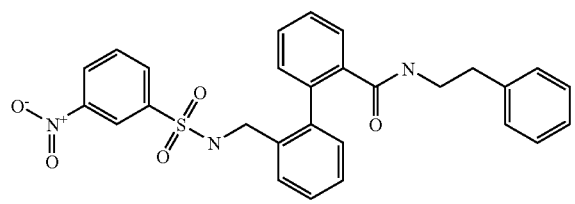

From 0.61 mmol of 2'-aminomethylbiphenyl-2-carboxylic acid phenethylamide (precursor 5 a) and 3-nitrophenylsulfonyl chloride, according to the general working procedure 272 mg of 2'-(3-nitrophenylsulfonylaminomethyl)biphenyl-2-carboxylic acid phenethylamide were obtained; m.p. 145° C. MS (ES+): m/e=516 (M+1).

Example 3 d

2'-(Phenylsulfonylaminomethyl)biphenyl-2-carboxylic acid phenethylamide

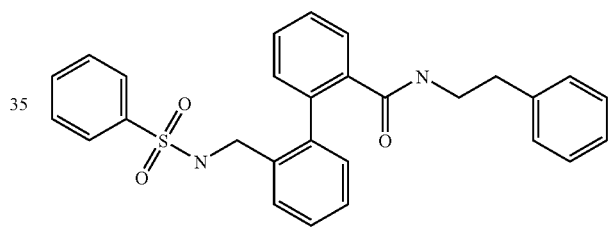

From 0.61 mmol of 2'-aminomethylbiphenyl-2-carboxylic acid phenethylamide (precursor 5 a) and phenylsulfonyl chloride according to the general working procedure 224 mg of 2'-(phenylsulfonylaminomethyl)biphenyl-2-carboxylic acid phenethylamide were obtained; m. p. 154° C. MS (ES+): m/e=471 (M+1).

Example 3 e

2'-(3-Fluorophenylsulfonylaminomethyl)biphenyl-2-carboxylic acid phenethylamide

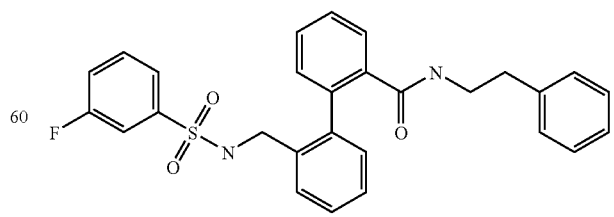

From 0.61 mmol of 2'-aminomethylbiphenyl-2-carboxylic acid phenethylamide (precursor 5 a) and 3-fluorophenylsulfonyl chloride, according to the general working procedure 221 mg of 2'-(3-fluorophenylsulfonylaminomethyl)biphenyl-2-carboxylic acid phenethylamide were obtained;

m.p. 153° C. MS (ES+): m/e=489 (M+1).

Example 3 f

2'-(4-Ethylphenylsulfonylaminomethyl)biphenyl-2-carboxylic acid phenethylamide

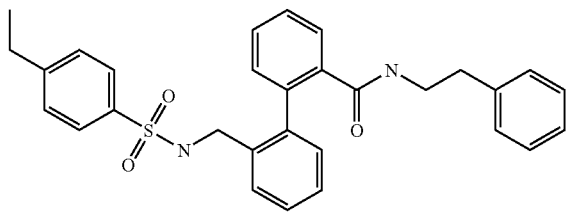

From 0.61 mmol of 2'-aminomethylbiphenyl-2-carboxylic acid phenethylamide (precursor 5 a) and 4-ethylphenylsulfonyl chloride, according to the general working procedure 250 mg of 2'-(4-ethylphenylsulfonylaminomethyl)biphenyl-2-carboxylic acid phenethylamide were obtained; m.p. 163° C. MS (ES+): m/e=499 (M+1).

Example 3 g

2'-(3-Trifluoromethylphenylsulfonylaminomethyl)biphenyl-2-carboxylic acid benzylamide

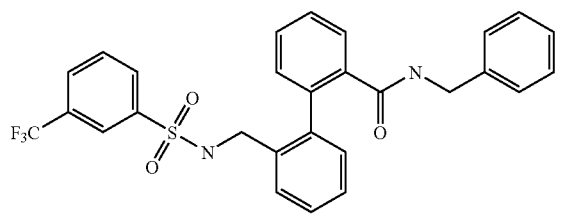

From 0.28 mmol of 2'-aminomethylbiphenyl-2-carboxylic acid benzylamide (precursor 5 b) and 3-trifluoromethylphenylsulfonyl chloride, according to the general working procedure 131 mg of 2'-(3-trifluoromethylphenylsulfonylaminomethyl)biphenyl-2-carboxylic acid benzylamide were obtained; m.p. 126° C. MS (ES+): m/e=525 (M+1).

Example 3 h

2'-(3-Acetylphenylsulfonylaminomethyl)biphenyl-2-carboxylic acid benzylamide

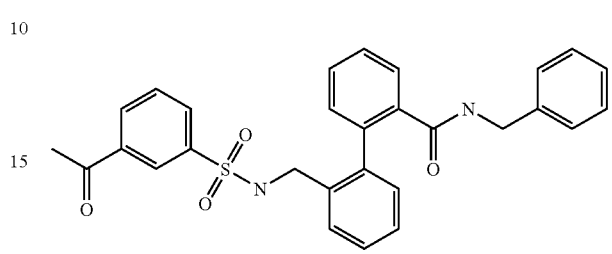

From 0.28 mmol of 2'-aminomethylbiphenyl-2-carboxylic acid benzylamide (precursor 5 b) and 3-acetylphenylsulfonyl chloride, according to the general working procedure 110 mg of 2'-(3-acetylphenylsulfonylaminomethyl)biphenyl-2-carboxylic acid benzylamide were obtained;

m.p. 182° C. MS (ES+): m/e=499 (M+1).

Example 3 i

2'-(3-Nitrophenylsulfonylaminomethyl)biphenyl-2-carboxylic acid benzylamide

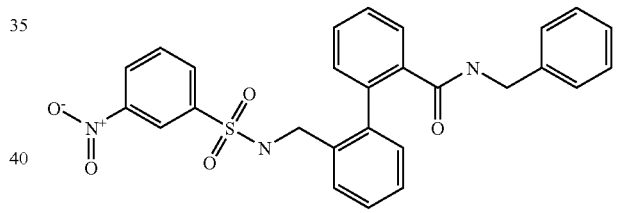

From 0.28 mmol of 2'-aminomethylbiphenyl-2-carboxylic acid benzylamide (precursor 5 b) and 3-nitrophenylsulfonyl chloride, according to the general working procedure 115 mg of 2'-(3-nitrophenylsulfonylaminomethyl)biphenyl-2-carboxylic acid benzylamide were obtained; m.p. 175° C. MS (ES+): m/e=502 (M+1).

Example 3 j

2'-(3-Phenylsulfonylaminomethyl)biphenyl-2-carboxylic acid benzylamide

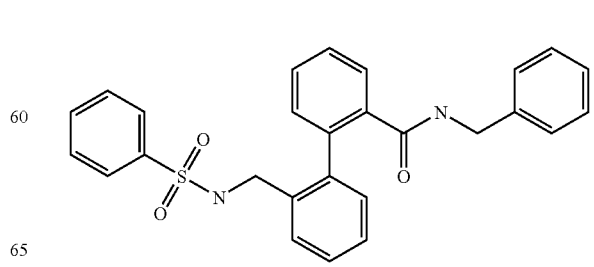

From 0.28 mmol of 2'-aminomethylbiphenyl-2-carboxylic acid benzylamide (precursor 5 b) and phenylsulfonyl chloride, according to the general working procedure 95 mg of 2'-(phenylsulfonylaminomethyl)biphenyl-2-carboxylic acid benzylamide were obtained; m.p. 162° C. MS (ES+): m/e=457 (M+1).

Example 3 k

2'-(3-Fluorophenylsulfonylaminomethyl)biphenyl-2-carboxylic acid benzylamide

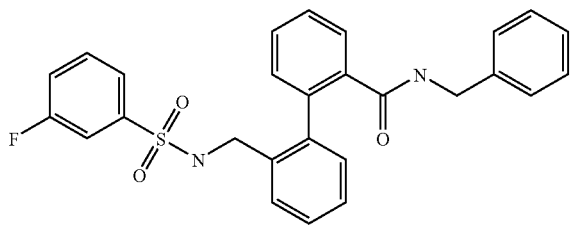

From 0.28 mmol of 2'-aminomethylbiphenyl-2-carboxylic acid benzylamide (precursor 5 b) and 3-fluorophenylsulfonyl chloride, according to the general working procedure 112 mg of 2'-(3-fluorophenylsulfonylaminomethyl)biphenyl-2-carboxylic acid benzylamide were obtained; m.p. 147° C. MS (ES+): m/e=475 (M+1).

Example 3 l

2'-(Phenylsulfonylaminomethyl)biphenyl-2-carboxylic acid (3-methylbutyl)amide

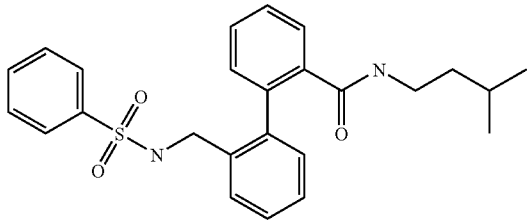

From 0.34 mmol of 2'-aminomethylbiphenyl-2-carboxylic acid (3-methylbutyl)amide (precursor 5 c) and phenylsulfonyl chloride, according to the general working procedure 100 mg of 2'-(phenylsulfonylaminomethyl)biphenyl-2-carboxylic acid (3-methylbutyl)amide were obtained; m.p. 127° C. MS (ES+): m/e=437 (M+1).

Example 3 m

2'-(4-Fluorophenylsulfonylaminomethyl)biphenyl-2-carboxylic acid (3-methylbutyl)amide

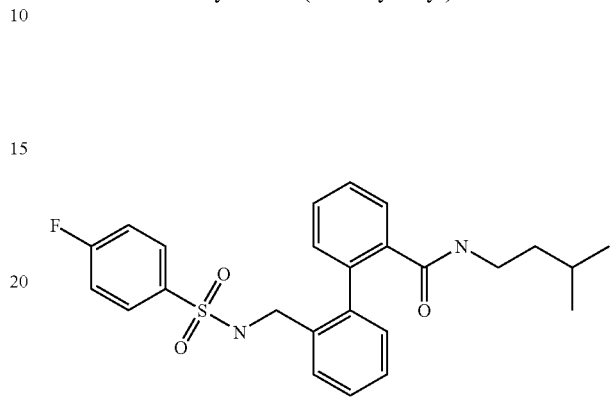

From 0.34 mmol of 2'-aminomethylbiphenyl-2-carboxylic acid (3-methylbutyl)amide (precursor 5 c) and 4-fluorophenylsulfonyl chloride, according to the general working procedure 122 mg of 2'-(4-fluorophenylsulfonylaminomethyl)biphenyl-2-carboxylic acid (3-methylbutyl)amide were obtained; m.p. 149° C. MS (ES+): m/e=455 (M+1).

Example 3 n

2'-(3-Fluorophenylsulfonylaminomethyl)biphenyl-2-carboxylic acid (3-methylbutyl)amide

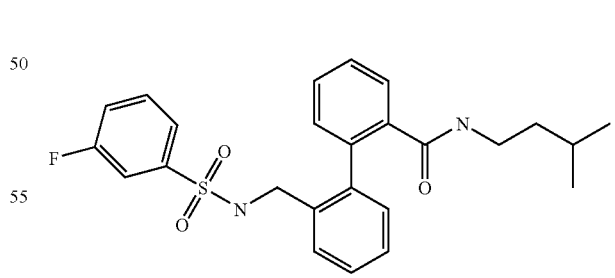

From 0.34 mmol of 2'-aminomethylbiphenyl-2-carboxylic acid (3-methylbutyl)amide (precursor 5 c) and 3-fluorophenylsulfonyl chloride, according to the general working procedure 118 mg of 2'-(3-fluorophenylsulfonylaminomethyl)

biphenyl-2-carboxylic acid (3-methylbutyl)amide were obtained; m.p. 141° C. MS (ES+): m/e=455 (M+1).

Example 3 o

2'-(Isopropylsulfonylaminomethyl)biphenyl-2-carboxylic acid (3-methylbutyl)amide

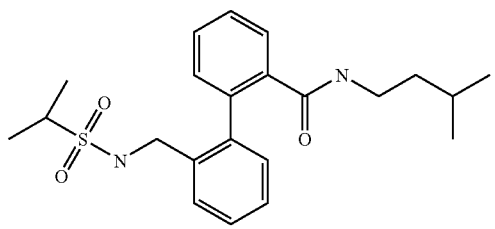

From 0.34 mmol of 2'-aminomethylbiphenyl-2-carboxylic acid (3-methylbutyl)amide (precursor 5 c) and isopropylsulfonyl chloride, according to the general working procedure followed by purification by flash chromatography 16 mg of 2'-(isopropylsulfonylaminomethyl)biphenyl-2-carboxylic acid (3-methylbutyl)amide were obtained as an oil. MS (ES+): m/e=403 (M+1).

Example 3 p

2'-(Phenylsulfonylaminomethyl)biphenyl-2-carboxylic acid 2-(2-pyridyl)ethylamide

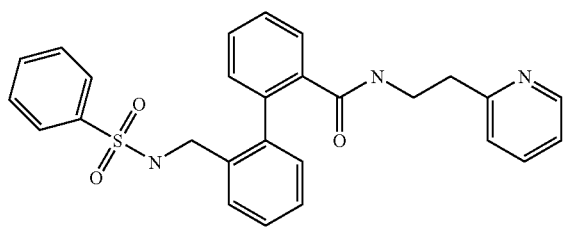

From 0.3 mmol of 2'-aminomethylbiphenyl-2-carboxylic acid 2-(2-pyridyl)ethylamide (precursor 5 d) and phenylsulfonyl chloride, according to the general working procedure 117 mg of 2'-(phenylsulfonylaminomethyl)biphenyl-2-carboxylic acid 2-(2-pyridyl)ethylamide were obtained; m.p. 131° C. MS (ES+): m/e=472 (M+1).

Example 3 q

2'-(4-Fluorophenylsulfonylaminomethyl)biphenyl-2-carboxylic acid 2-(2-pyridyl)ethylamide

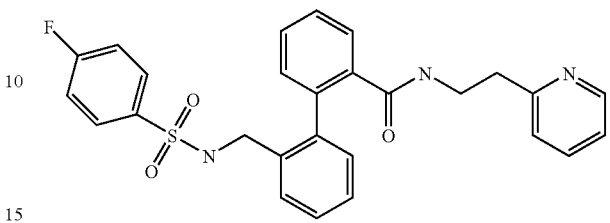

From 0.3 mmol of 2'-aminomethylbiphenyl-2-carboxylic acid 2-(2-pyridyl)ethylamide (precursor 5 d) and 4-fluorophenylsulfonyl chloride, according to the general working procedure 106 mg of 2'-(4-fluorophenylsulfonylaminomethyl)biphenyl-2-carboxylic acid 2-(2-pyridyl)ethylamide were obtained; m.p. 130° C. MS (ES+): m/e=490 (M+1).

Example 3 r

2'-(3-Fluorophenylsulfonylaminomethyl)biphenyl-2-carboxylic acid 2-(2-pyridyl)ethylamide

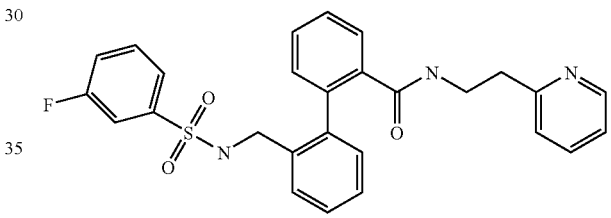

From 0.3 mmol of 2'-aminomethylbiphenyl-2-carboxylic acid 2-(2-pyridyl)ethylamide (precursor 5 d) and 3-fluorophenylsulfonyl chloride, according to the general working procedure 102 mg of 2'-(3-fluorophenylsulfonylaminomethyl)biphenyl-2-carboxylic acid 2-(2-pyridyl)ethylamide were obtained; m.p. 123° C. MS (ES+): m/e=490 (M+1).

Example 3 s

2'-(Isopropylsulfonylaminomethyl)biphenyl-2-carboxylic acid 2-(2-pyridyl)ethylamide

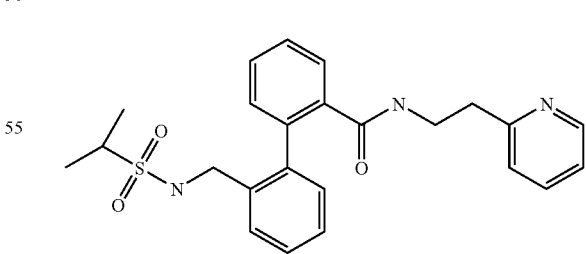

From 0.3 mmol of 2'-aminomethylbiphenyl-2-carboxylic acid 2-(2-pyridyl)ethylamide (precursor 5 d) and isopropylsulfonyl chloride, according to the general working procedure and subsequent extraction with EA 40 mg of 2'-(isopropylsulfonylaminomethyl)biphenyl-2-carboxylic acid 2-(2-pyridyl)ethylamide were obtained as an oil. MS (ES+): m/e=438 (M+1).

The following compound was obtained analogously to Examples 3 a-3 s:

| Example No. | Structure | MS (ES+): m/e = |
|---|---|---|
| 3 t | 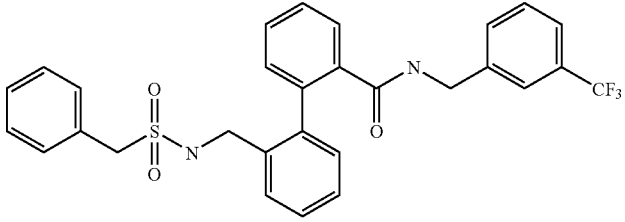 | 539 |

General Procedure for the Reaction of Aminomethylbiphenyls with Carbonyl Chlorides to Give Carboxamides (Examples 4 a to 4 l):

0.36 mmol of the respective sulfonyl chloride is slowly added dropwise at 0° C. to a solution of 0.34 mmol of the respective 2'-aminomethylbiphenyl and 41 mg (0.41 mmol) of triethylamine in 5 ml of methylene chloride. After stirring at RT for 3 h, the reaction mixture is concentrated in vacuo, the residue is stirred with 25 ml of water and the precipitated product is filtered off with suction or isolated by extraction with EA.

Example 4 a 2'-(Benzoylaminomethyl)biphenyl-2-carboxylic acid (3-methylbutyl)amide

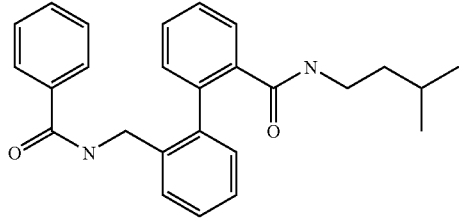

From 0.34 mmol of 2'-aminomethylbiphenyl-2-carboxylic acid (3-methylbutyl)amide (precursor 5 c) and benzoyl chloride, according to the general working procedure 75 mg of 2'-(benzoylaminomethyl)biphenyl-2-carboxylic acid (3-methylbutyl)amide were obtained; m.p. 147° C. MS (ES+): m/e=401 (M+1).

Example 4 b

2'-(Benzoylaminomethyl)biphenyl-2-carboxylic acid 2-(2-pyridyl)ethylamide

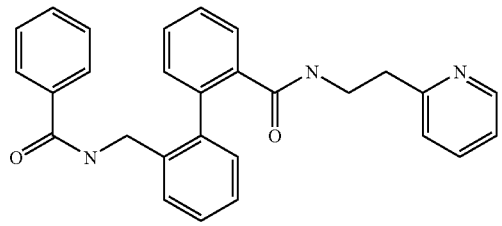

From 0.3 mmol of 2'-aminomethylbiphenyl-2-carboxylic acid 2-(2-pyridyl)ethylamide (precursor 5 d) and benzoyl chloride, according to the general working procedure 98 mg of 2'-(benzoylaminomethyl)biphenyl-2-carboxylic acid 2-(2-pyridyl)ethylamide were obtained; m.p. 135° C. MS (ES+): m/e=436 (M+1).

Example 4 c

2'-{[2-(4-Methoxyphenyl)acetylamino]methyl}biphenyl-2-carboxylic acid 2,4-difluorobenzylamide

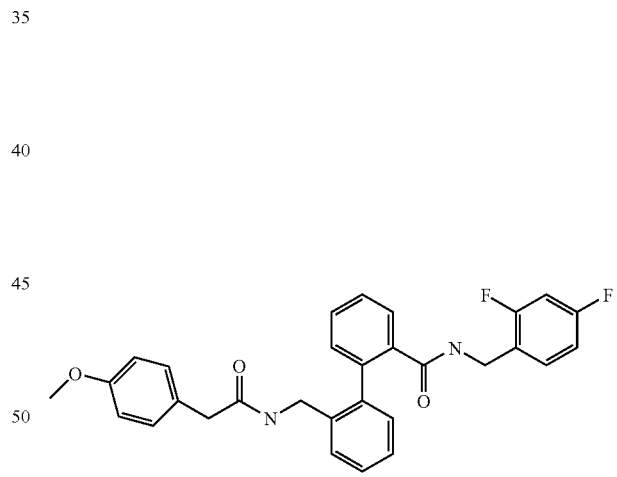

From 0.5 mmol of 2'-aminomethylbiphenyl-2-carboxylic acid (2,4-difluorobenzyl)amide (precursor 8 a) and 4-methoxyphenylacetyl chloride, according to the general working procedure 160 mg of 2'-{[2-(4-methoxyphenyl)acetylamino]methyl}biphenyl-2-carboxylic acid 2,4-difluorobenzylamide were obtained; m.p. 138° C. MS (ES+): m/e=501 (M+1).

The following compounds were obtained analogously to Examples 4 a-4 c:

| Example No. | Structure | ME (ES+) m/e = | M.p. |
|---|---|---|---|
| 4 d | 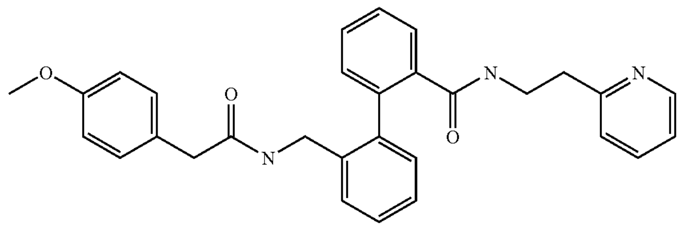 | 480 | |
| 4 e | 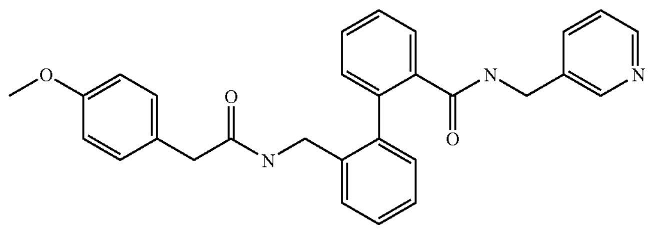 | 466 | |
| 4 f | 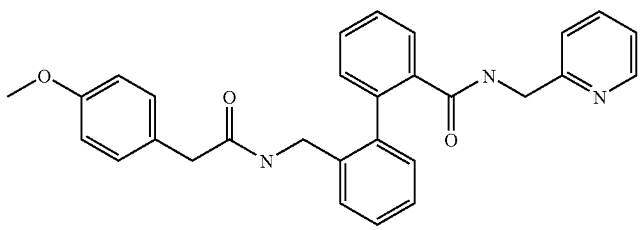 | 466 | |
| 4 g | 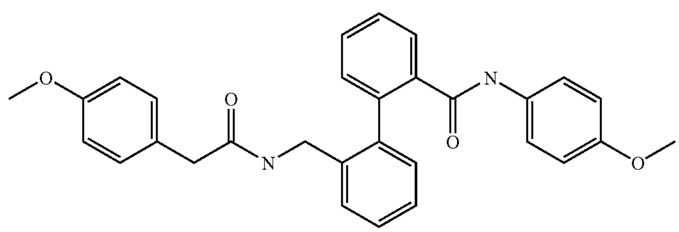 | 481 | |
| 4 h | 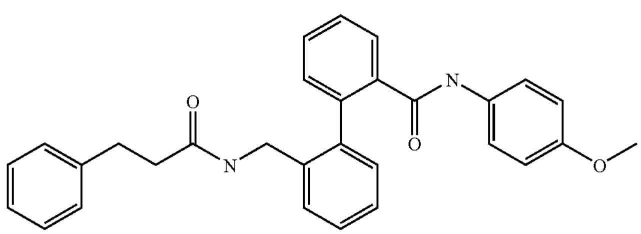 | 465 | |
| 4 i | 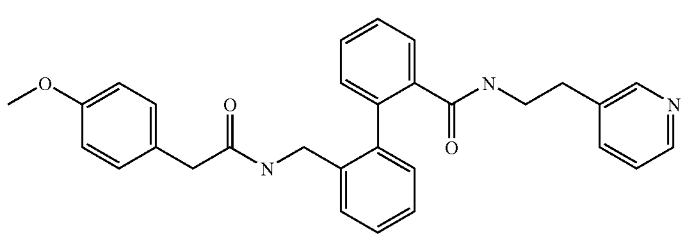 | 480 | 116° C. |

| Example No. | Structure | ME (ES+) m/e = | M.p. |
|---|---|---|---|
| 4 j | 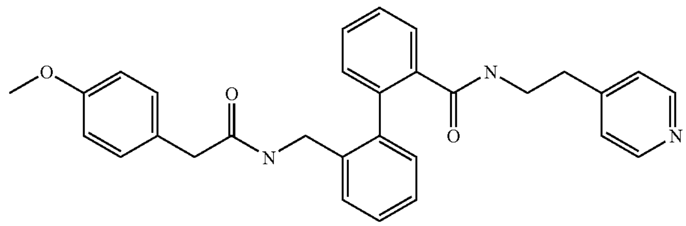 | 480 | |
| 4 k | 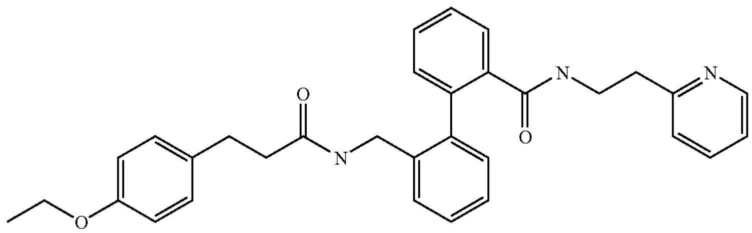 | 508 | |
| 4 l | 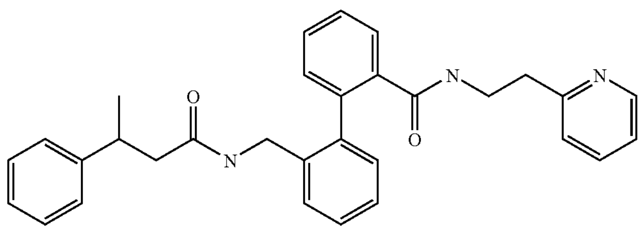 | 478 | |

General Procedure for the Reaction of Aminomethylbiphenyls with Isocyanates to Give Ureas (Examples 5 a-5 e):

0.36 mmol of the respective isocyanate dissolved in 0.5 ml of methylene chloride is slowly added dropwise at 0° C. to a solution of 0.34 mmol of the respective 2'-aminomethylbiphenyl and 41 mg (0.41 mmol) of triethylamine in 5 ml of methylene chloride. After stirring at RT for 3 h, the reaction mixture is concentrated in vacuo, the residue is stirred with 25 ml of water and the precipitated product is filtered off with suction or isolated by extraction with EA.

Example 5 a

2'-[(3-Phenylureido)methyl]biphenyl-2-carboxylic acid (3-methylbutyl)amide

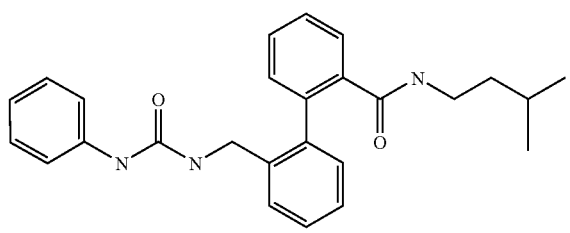

From 0.34 mmol of 2'-aminomethylbiphenyl-2-carboxylic acid (3-methylbutyl)amide (precursor 5 c) and phenyl isocyanate, according to the general working procedure 85 mg of 2'-[(3-phenylureido)methyl]biphenyl-2-carboxylic acid (3-methylbutyl)amide were obtained; m.p. 194° C. MS (ES+): m/e=416 (M+1).

Example 5 b

2'-[(3-Phenylureido)methyl]biphenyl-2-carboxylic acid 2-(2-pyridyl)ethylamide

From 0.3 mmol of 2'-aminomethylbiphenyl-2-carboxylic acid 2-(2-pyridyl)ethylamide (precursor 5 d) and phenyl isocyanate, according to the general working procedure 101 mg of 2'-[(3-phenylureido)methyl]biphenyl-2-carboxylic acid 2-(2-pyridyl)ethylamide were obtained; m.p. 99° C. MS (ES+): m/e=451 (M+1).

Examples 5 c-5 e

The following compounds were obtained analogously from 2'-aminomethylbiphenyl-2-carboxylic acid 2-(2-pyridyl)ethylamide (precursor 5 d) and the corresponding isocyanates:

| Example No. | Structure | | MS (ES+): m/e = |
|---|---|---|---|
| 5 c | 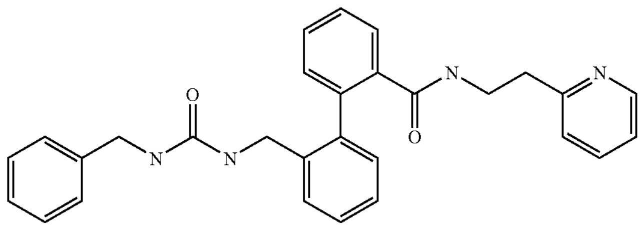 | | 465 |
| 5 d | 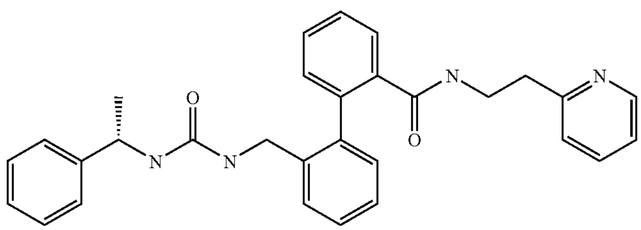 | Chiral | 479 |
| 5 e | 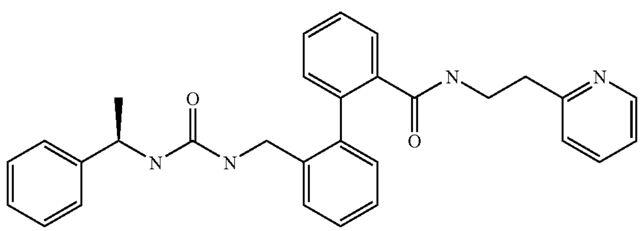 | Chiral | 479 |

General Procedure for the Reaction of Biphenylcarboxylic Acids with Amines to Give Amides (Examples 6 a-6 h):

0.3 mmol of the respective amine is added dropwise at 0° C. to a solution of 0.28 mmol of the appropriate biphenylcarboxylic acid, 0.3 mmol of HOBT and 0.3 mmol of DIC in 5 ml of THF and it is stirred at RT for 12 h. The reaction mixture is diluted with EA and washed with dilute hydrochloric acid and sodium bicarbonate solution. After drying over magnesium sulfate and concentrating in vacuo, the corresponding amide is obtained.

Example 6 a

2'-(Benzyloxycarbonylaminomethyl)biphenyl-2-carboxylic acid benzylmethylamide

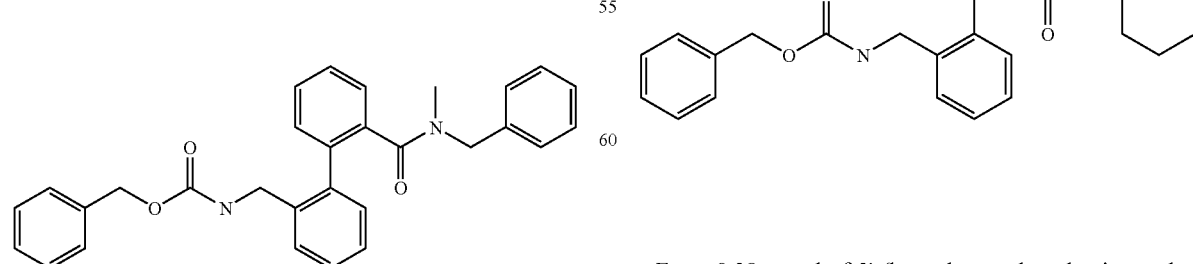

From 0.28 mmol of 2'-(benzyloxycarbonylaminomethyl)biphenyl-2-carboxylic acid (precursor 6) and benzylmethylamine, according to the general working procedure 89 mg of 2'-(benzyloxycarbonylaminomethyl)biphenyl-2-carboxylic acid benzylmethylamide were obtained. MS (ES+): m/e=465 (M+1).

Example 6 b

2'-(Benzyloxycarbonylaminomethyl)biphenyl-2-carboxylic acid cyclohexylamide

From 0.28 mmol of 2'-(benzyloxycarbonylaminomethyl)biphenyl-2-carboxylic acid (precursor 6) and cyclohexylamine, according to the general working procedure 99 mg of 2'-(benzyloxycarbonylaminomethyl)biphenyl-2-carboxylic acid cyclohexylamide were obtained. MS (ES+): m/e=443 (M+1).

Example 6 c

2'-(Benzyloxycarbonylaminomethyl)biphenyl-2-carboxylic acid phenylamide

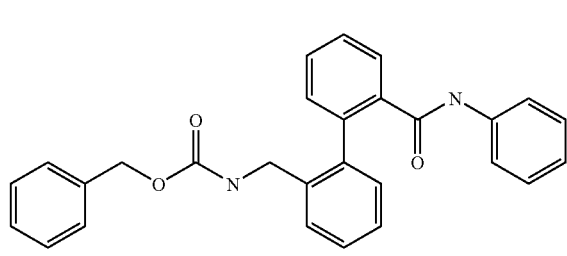

From 0.28 mmol of 2'-(benzyloxycarbonylaminomethyl) biphenyl-2-carboxylic acid (precursor 6) and aniline, according to the general working procedure 66 mg of 2'-(benzyloxycarbonylaminomethyl)biphenyl-2-carboxylic acid phenylamide were obtained. MS (ES+): m/e=437 (M+1).

Example 6 d

2'-(Benzyloxycarbonylaminomethyl)biphenyl-2-carboxylic acid {N-methyl-N-[2-(2-pyridyl)ethyl]}amide

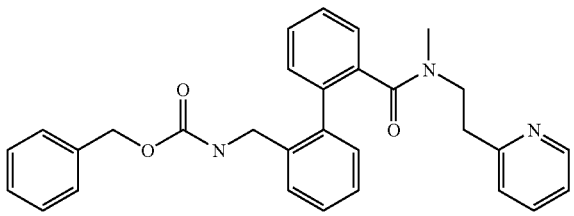

From 0.28 mmol of 2'-(benzyloxycarbonylaminomethyl) biphenyl-2-carboxylic acid (precursor 6) and 2-[2-(methylaminoethyl)]pyridine, according to the general working procedure and subsequent purification by flash chromatography 54 mg of 2'-(benzyloxycarbonylaminomethyl)biphenyl-2-carboxylic acid {N-methyl-N-[2-(2-pyridyl)ethyl]}amide were obtained. MS (ES+): m/e=480 (M+1).

Example 6 e

2'-(Benzyloxycarbonylaminomethyl)biphenyl-2-carboxylic acid dibutylamide

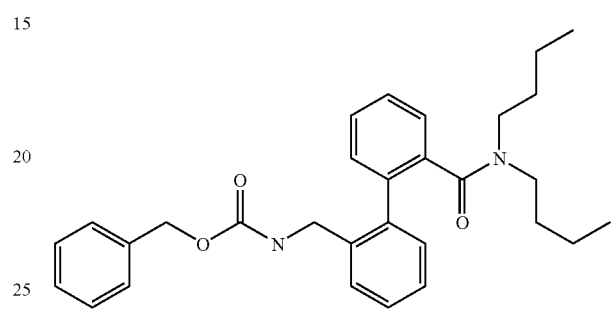

From 0.28 mmol of 2'-(benzyloxycarbonylaminomethyl) biphenyl-2-carboxylic acid (precursor 6) and dibutylamine, according to the general working procedure and subsequent purification by flash chromatography 82 mg of 2'-(benzyloxycarbonylaminomethyl)biphenyl-2-carboxylic acid dibutylamide were obtained. MS (ES+): m/e=473 (M+1).

Example 6 f

2'-(Benzyloxycarbonylaminomethyl)biphenyl-2-carboxylic Acid 2-(2-pyridyl)ethylamide

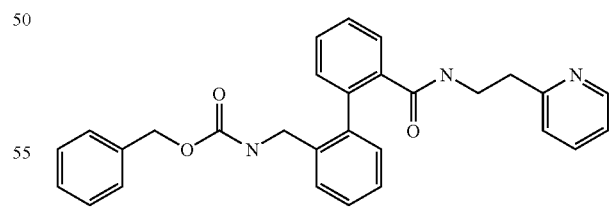

From 0.28 mmol of 2'-(benzyloxycarbonylaminomethyl) biphenyl-2-carboxylic acid (precursor 6) and 2-(2-pyridyl) ethylamine, according to the general working procedure and subsequent purification by flash chromatography 85 mg of 2'-(benzyloxycarbonylaminomethyl)biphenyl-2-carboxylic acid 2-(2-pyridyl)ethylamide were obtained; m.p. 140° C. (heptane/EA); MS (ES+): m/e=466 (M+1).

Example 6 g

2'-(Benzyloxycarbonylaminomethyl)biphenyl-2-carboxylic acid (2,4-difluorobenzyl)amide

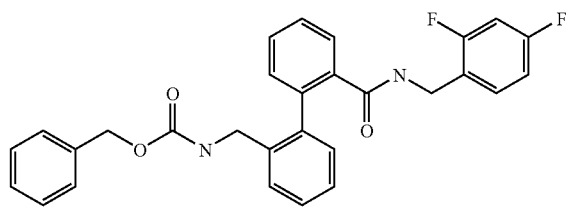

From 0.28 mmol of 2'-(benzyloxycarbonylaminomethyl) biphenyl-2-carboxylic acid (precursor 6) and 2,4-difluorobenzylamine, according to the general working procedure and subsequent purification by flash chromatography 99 mg of 2'-(benzyloxycarbonylaminomethyl)biphenyl-2-carboxylic acid (2,4-difluorobenzyl)amide were obtained. MS (ES+): m/e=487 (M+1).

Example 6 h

2'-(Benzyloxycarbonylaminomethyl)biphenyl-2-carboxylic acid (2,2,2-trifluoroethyl)amide

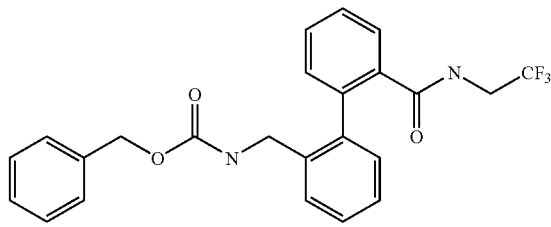

From 0.28 mmol of 2'-(benzyloxycarbonylaminomethyl) biphenyl-2-carboxylic acid (precursor 6) and 2,2,2-trifluoroethylamine, according to the general working procedure and subsequent purification by flash chromatography 19 mg of 2'-(benzyloxycarbonylaminomethyl)biphenyl-2-carboxylic acid (2,2,2-trifluoroethyl)amide were obtained. MS (ES+): m/e=443 (M+1).

Example 7 a

2'-(Benzyloxycarbonylaminomethyl)biphenyl-2-carboxylic acid 2-[2-(1-oxypyridyl)]ethylamide

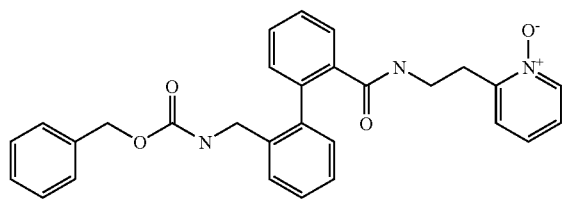

47 mg of m-chloroperbenzoic acid dissolved in 2 ml of methylene chloride were added dropwise at 0° C. to a solution of 85 mg (0.18 mmol) of 2'-(benzyloxycarbonylaminomethyl)biphenyl-2-carboxylic acid 2-(2-pyridyl)ethylamide (Example 6 f) in 13 ml of methylene chloride and the reaction mixture was stirred at RT for 12 h. The organic phase was washed 2 times with sodium bicarbonate solution, dried over magnesium sulfate and concentrated in vacuo. 79 mg of 2'-(benzyloxycarbonylaminomethyl)biphenyl-2-carboxylic acid 2-[2-(1-oxypyridyl)]ethylamide were obtained. MS (ES+): m/e=482 (M+1).

The following compounds were obtained from the corresponding pyridines analogously to Example 7 a:

| Example No. | Structure | MS (ES+): m/e = |
|---|---|---|
| 7 b | ![structure] | 482 |

| Example No. | Structure | MS (ES+): m/e = |
|---|---|---|
| 7 c | 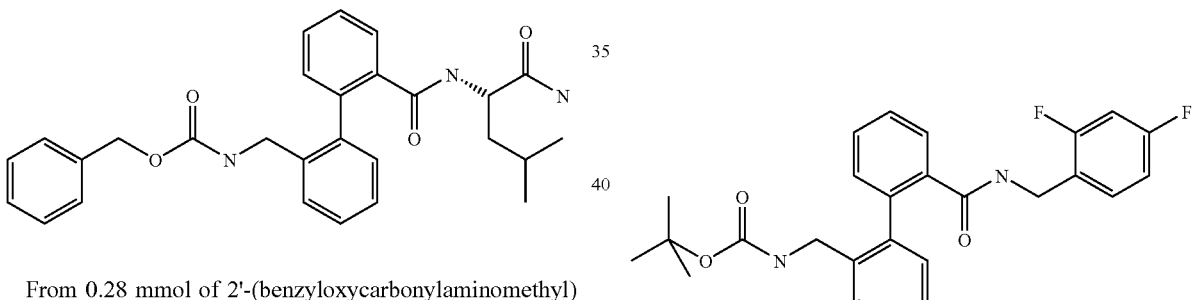 | 496 |

General Procedure for the Reaction of Biphenylcarboxylic Acids with Amines to Give Amides (Examples 8 a-8 c):

0.44 mmol of the respective amine is added dropwise at 0° C. to a solution of 0.42 mmol of the appropriate biphenylcarboxylic acid, 0.44 mmol of HOBT and 0.44 mmol of EDAC in 5 ml of THF and it is stirred at RT for 4 to 12 h. The reaction mixture is diluted with EA and washed with dilute hydrochloric acid and sodium bicarbonate solution. After drying over magnesium sulfate and concentrating in vacuo, the corresponding amide is obtained.

Example 8 a

Benzyl [2'-(1-carbamoyl-3-methylbutylcarbamoyl) biphenyl-2-ylmethyl]carbamate

From 0.28 mmol of 2'-(benzyloxycarbonylaminomethyl) biphenyl-2-carboxylic acid (precursor 6) and L-leucinamide hydrochloride/triethylamine, according to the general working procedure 180 mg of benzyl [2'-(1-carbamoyl-3-methylbutylcarbamoyl)biphenyl-2-ylmethyl]carbamate were obtained. MS (ES+): m/e=474 (M+1).

Example 8 b methyl 2-{[2'-(benzyloxycarbonylaminomethyl)biphenyl-2-carbonyl]amino}-3-phenylpropionate

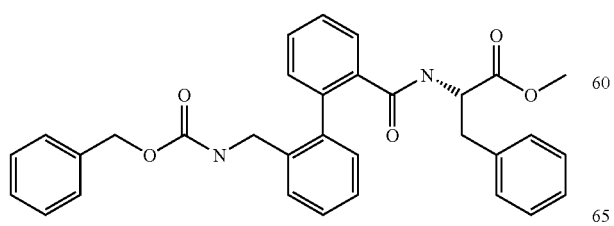

From 0.28 mmol of 2'-(benzyloxycarbonylaminomethyl) biphenyl-2-carboxylic acid (precursor 6) and L-phenylalanine methyl ester hydrochloride/triethylamine, according to the general working procedure 230 mg of methyl 2-{[2'-(benzyloxycarbonylaminomethyl)biphenyl-2-carbonyl] amino}-3-phenylpropionate were obtained. MS (ES+): m/e=523 (M+1).

Example 8 c

2'-(tert-Butoxycarbonylaminomethyl)biphenyl-2-carboxylic acid (2,4-difluorobenzyl)amide From 10 mmol of 2'-(tert-butoxycarbonylaminomethyl)biphenyl-2-carboxylic acid (precursor 7) and 2,4-difluorobenzylamine, according to the general working procedure 3.8 g of 2'-(tert-butoxycarbonylaminomethyl)biphenyl-2-carboxylic acid (2,4-difluorobenzyl)amide were obtained. MS (ES+): m/e=453 (M+1).

Examples 8 d-8 p

The following products were obtained from 2'-(tert-butoxycarbonylaminomethyl)biphenyl-2-carboxylic acid (precursor 7) and the corresponding amines analogously to Examples 8 a-8 c:

| Example No. | Structure | MS (ES+): m/e = | M.p. |
|---|---|---|---|
| 8 d | 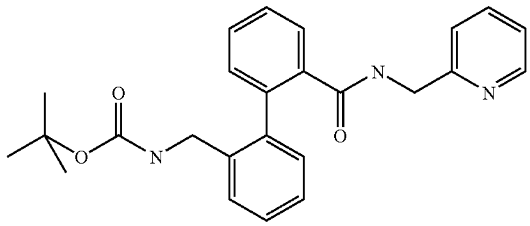 | 418 | 139 |
| 8 e | 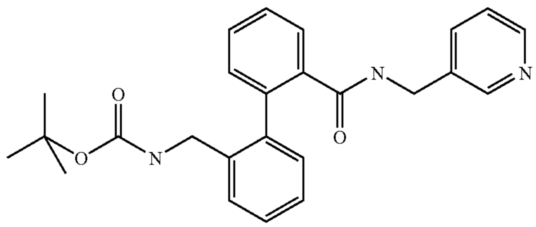 | 418 | 171 |
| 8 f | 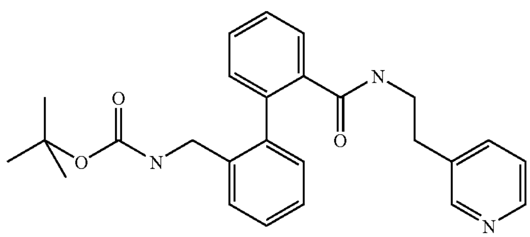 | 432 | 161 |
| 8 g | 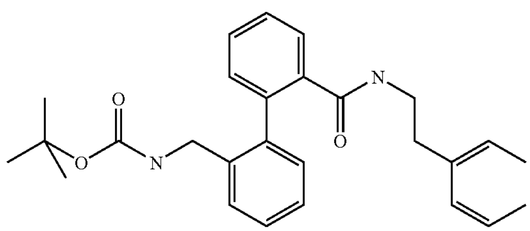 | 432 | 59 |
| 8 i | 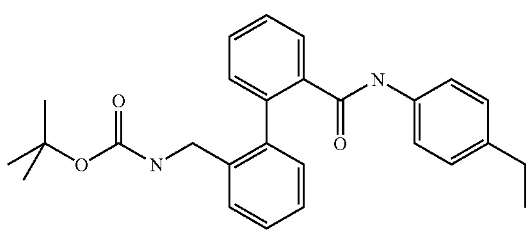 | 431 | 171 |
| 8 j | 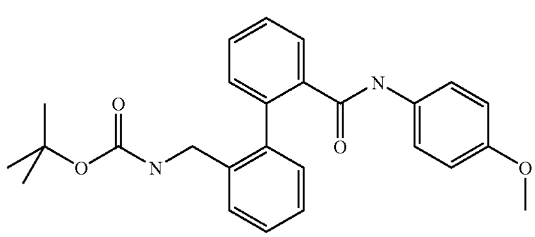 | 433 | 165 |

-continued

| Example No. | Structure | MS (ES+): m/e = | M.p. |
|---|---|---|---|
| 8 k | 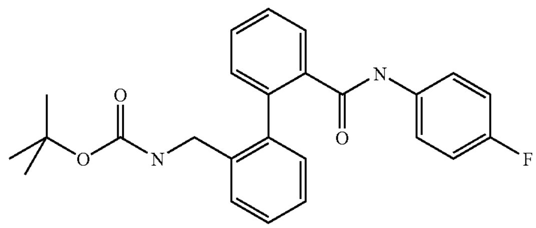 | 421 | 199 |
| 8 l | 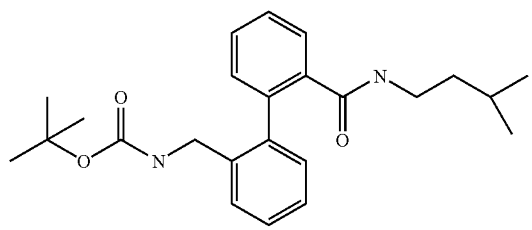 | 397 | |
| 8 m | Chiral | 461 | |
| 8 n | 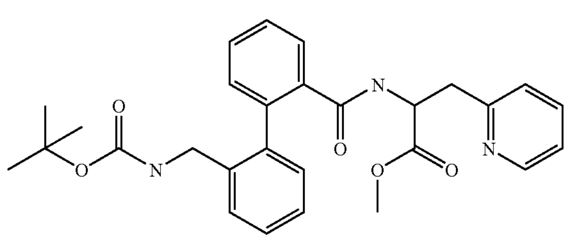 | 490 | |
| 8 o | 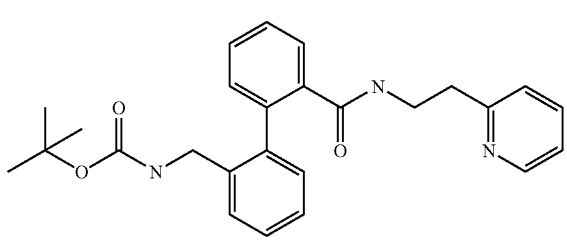 | 432 | |

Examples 8 p-8 ac

The following products were obtained from 2'-(benzyloxycarbonylaminomethyl)biphenyl-2-carboxylic acid (precursor 6) and the corresponding amines analogously to Examples 8 a-8 c:

| Example No. | Structure | MS (ES+): m/e = | M.p. |
|---|---|---|---|
| 8 p | 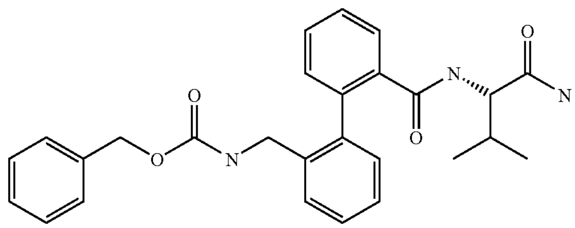 | 460 | 119° C. |
| 8 q | 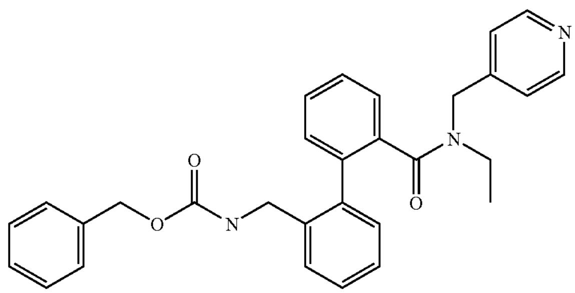 | 480 | |
| 8 r | 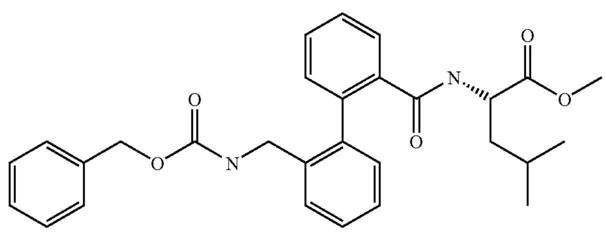 | 489 | |
| 8 s | 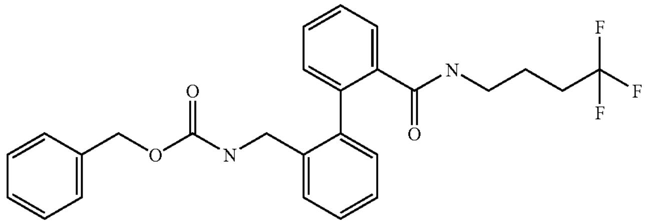 | 471 | |
| 8 x | 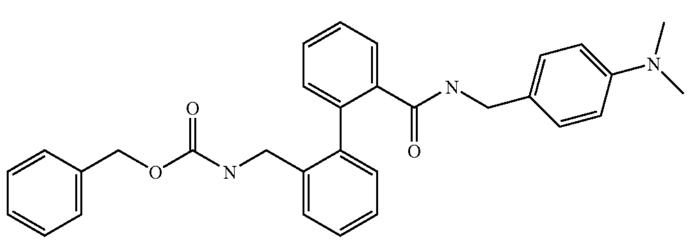 | 494 | |

-continued

| Example No. | Structure | MS (ES+): m/e = | M.p. |
|---|---|---|---|
| 8 y | 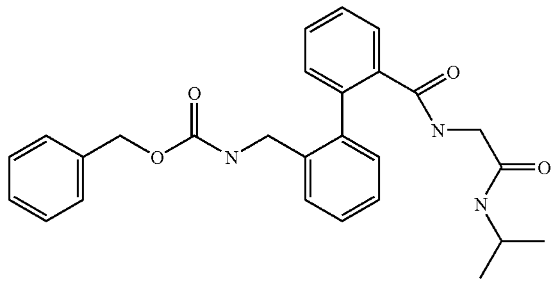 | 460 | |
| 8 z | 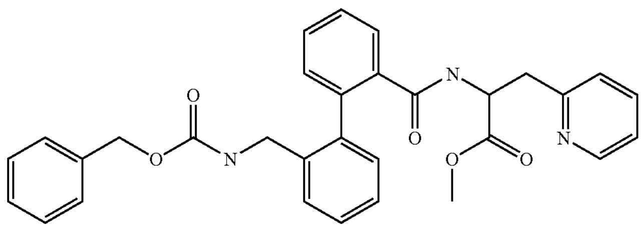 | 524 | |
| 8 aa | 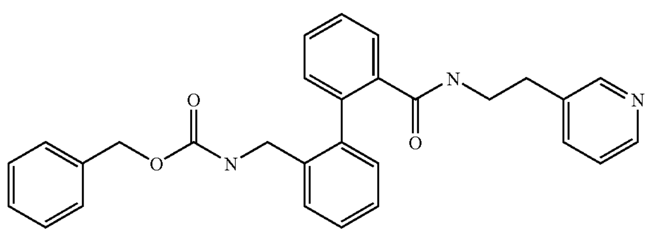 | 466 | |
| 8 ab | 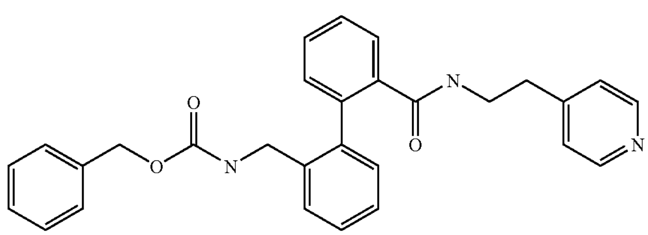 | 466 | 132° C. |
| 8 ac | 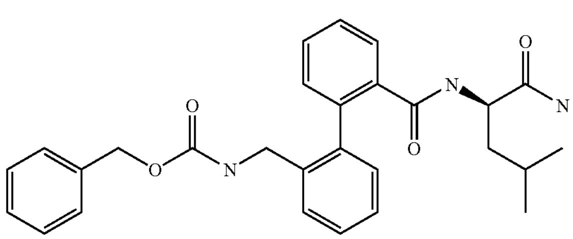 | 474 | |

General Procedure for the Reaction of Aminomethylbiphenyls with Isothiocyanates to Give Thioureas (Examples 9 a-9 i):

0.36 mmol of the respective isothiocyanate dissolved in 0.5 ml of methylene chloride is slowly added dropwise at 0° C. to a solution of 0.34 mmol of the respective 2'-aminomethylbiphenyl and 41 mg (0.41 mmol) of triethylamine in 5 ml of methylene chloride. After stirring at RT for 3 h, the reaction mixture is concentrated in vacuo, the residue is stirred with 25 ml of water and the precipitated product is filtered off with suction or purified by preparative HPLC.

The following products, inter alia, were obtained in this way:

| Example No. | Structure | MS (ES+): m/e = |
|---|---|---|
| 9 a | 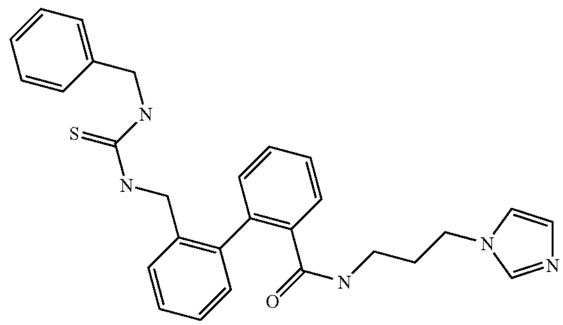 | 483 |
| 9 c | 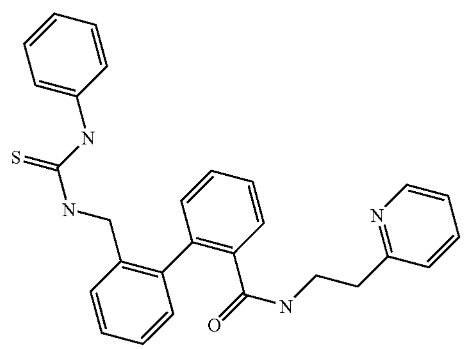 | 466 |
| 9 d | 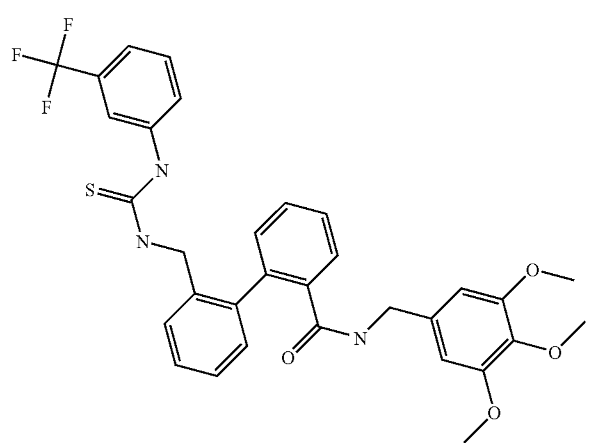 | 609 |

-continued

| Example No. | Structure | MS (ES+): m/e = |
|---|---|---|
| 9 e | 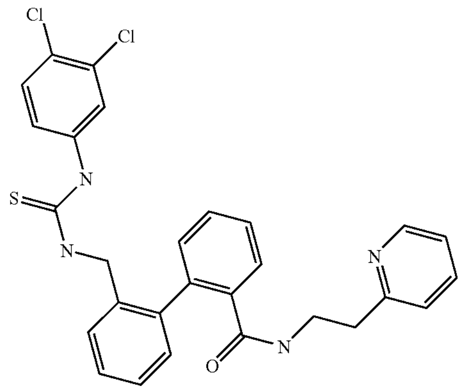 | 534 |
| 9 f | 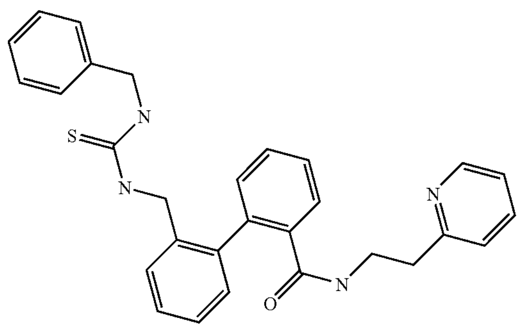 | 480 |
| 9 g | 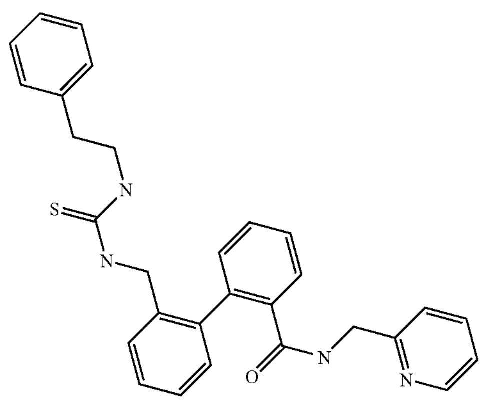 | 480 |
| 9 h | 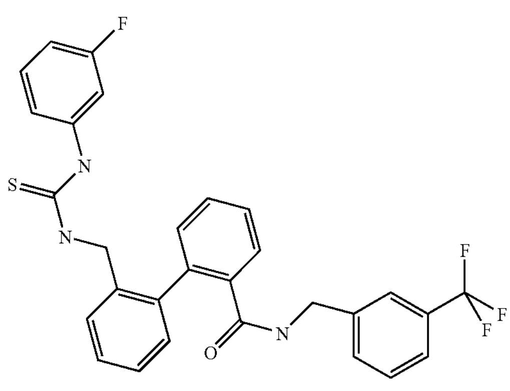 | 537 |

| Example No. | Structure | MS (ES+): m/e = |
|---|---|---|
| 9 i | 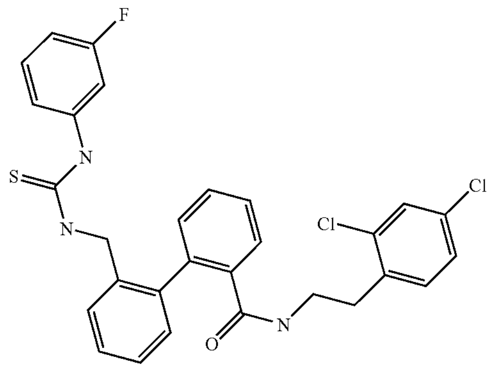 | 551 |

Examples 10 a-10 o

The following products, inter alia, were obtained by coupling 2'-(tertbutyloxycarbonylaminomethyl)biphenyl-2-carboxylic acid (precursor 7) with corresponding amines analogously to the methods described for Example 6 or 8:

| Example No. | Structure | MS (ES+): m/e = |
|---|---|---|
| 10 a | 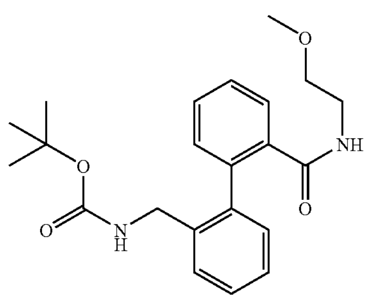 | 384 |
| 10 b | 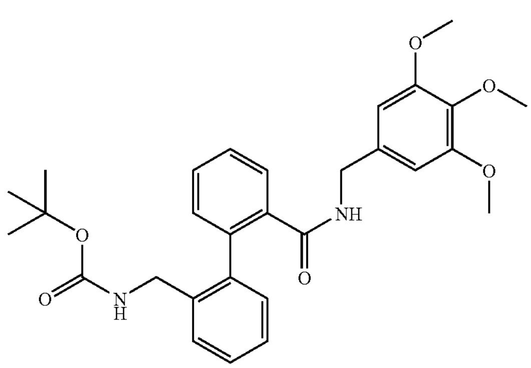 | 506 |

| Example No. | Structure | MS (ES+): m/e = |
|---|---|---|
| 10 c | 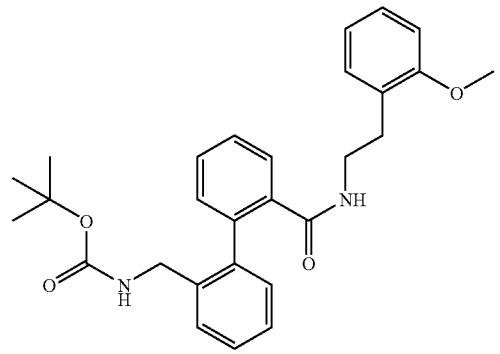 | 460 |
| 10 d | 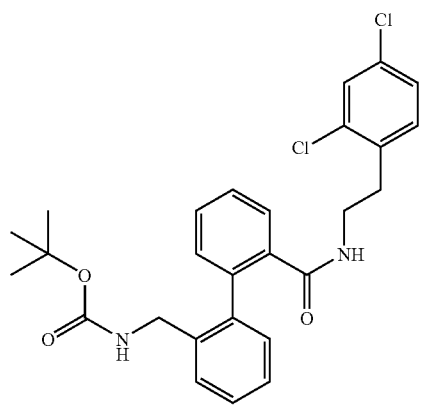 | 498 |
| 10 e | 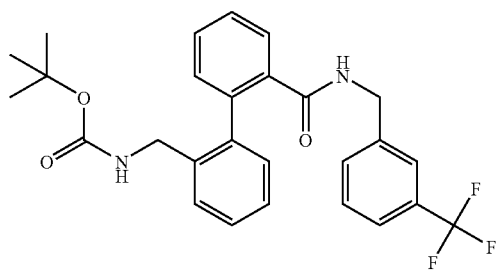 | 484 |
| 10 f | 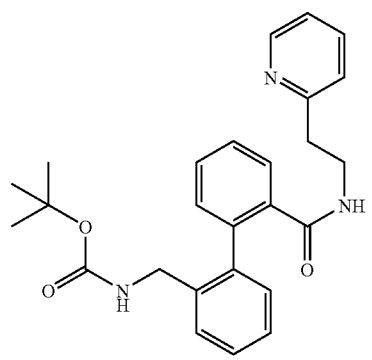 | 431 |

-continued
| Example No. | Structure | MS (ES+): m/e = |
|---|---|---|
| 10 g | 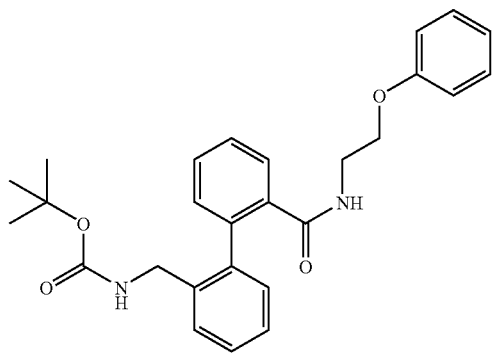 | 446 |
| 10 h | 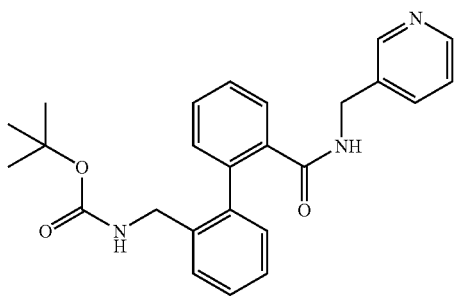 | 417 |
| 10 i | 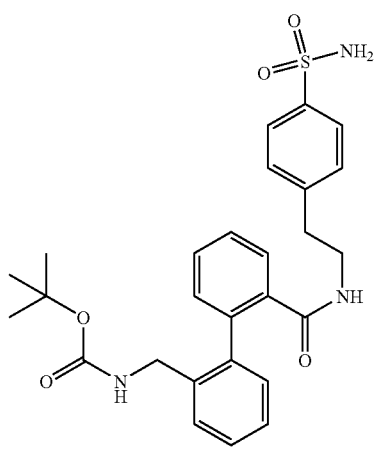 | 509 |
| 10 j | 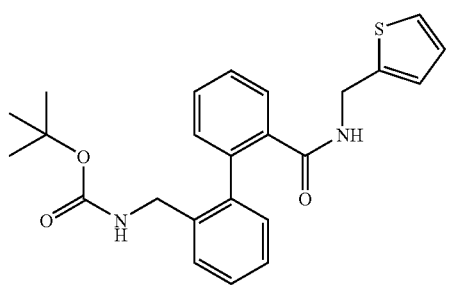 | 422 |

-continued
| Example No. | Structure | MS (ES+): m/e = |
|---|---|---|
| 10 k | 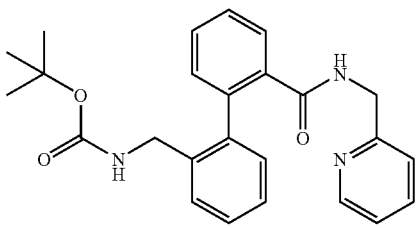 | 417 |
| 10 l | 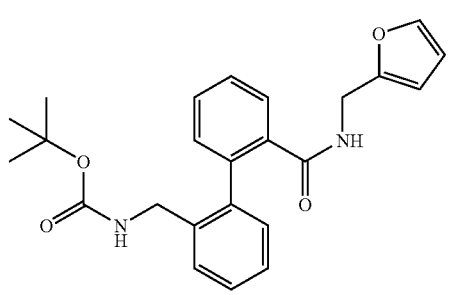 | 406 |
| 10 m | 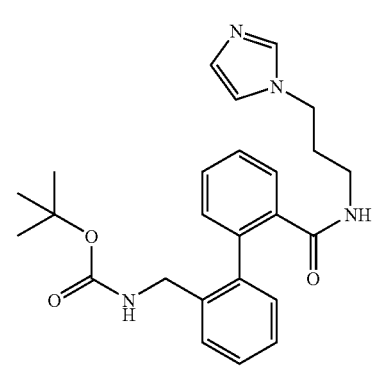 | 434 |
| 10 n | 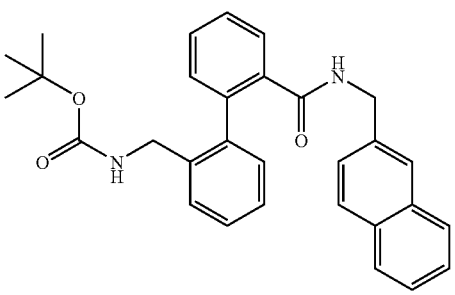 | 466 |
| 10 o | 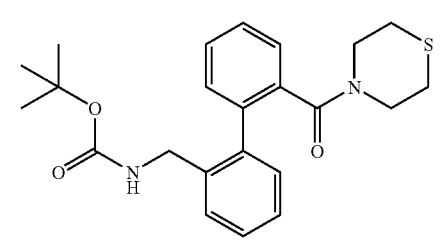 | 412 |

Examples 11 a-11 r

General Procedure for the Conversion of the Boc Derivatives of Examples 10 to Ureas For the removal of the Boc protective group, 1 g of the appropriate compound of Example 10 was added to 10 ml of a 30% solution of TFA in dichloromethane. The mixture was stirred at RT for 30 min and the solvent was removed in vacuo on a rotary evaporator. The residue was taken up in ethyl acetate and washed with saturated sodium hydrogencarbonate solution. The organic phase was dried over magnesium sulfate and filtered, and the solvent was removed in vacuo. The 2'-aminomethylbiphenyl-2-carboxamides obtained were then reacted with isocyanates to give the corresponding ureas according to the procedure for Examples 5.

The following products, inter alia, were obtained in this way:

| Example No. | Structure | MS (ES+): m/e = |
|---|---|---|
| 11 a | 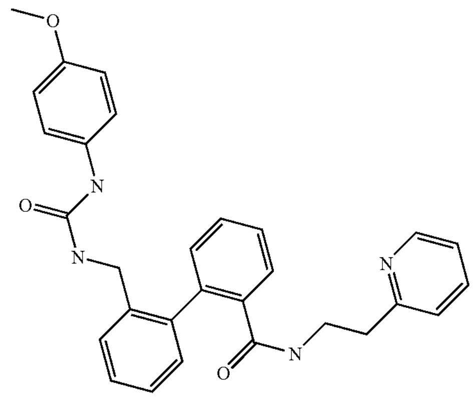 | 480 |
| 11 b | 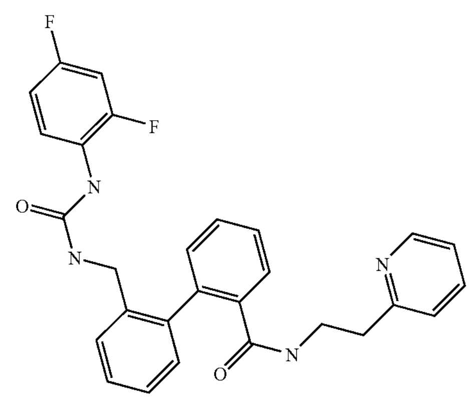 | 486 |
| 11 c | 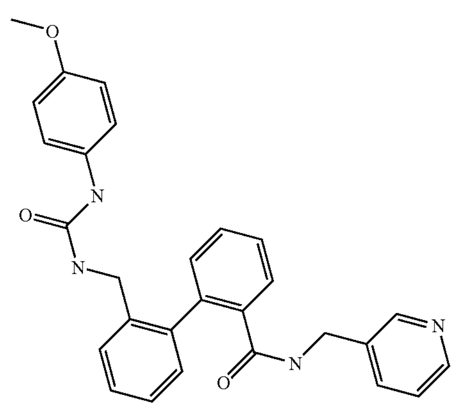 | 466 |

-continued
| Example No. | Structure | MS (ES+): m/e = |
|---|---|---|
| 11 d | 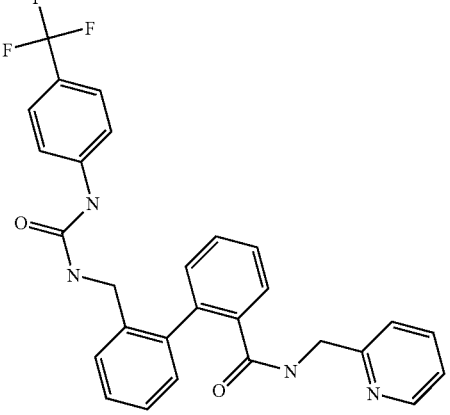 | 504 |
| 11 e | 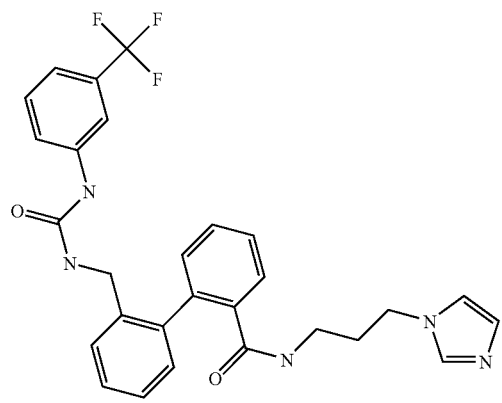 | 521 |
| 11 f | 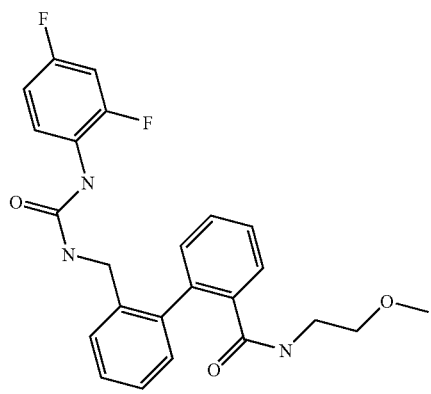 | 439 |

-continued
| Example No. | Structure | MS (ES+): m/e = |
|---|---|---|
| 11 g | 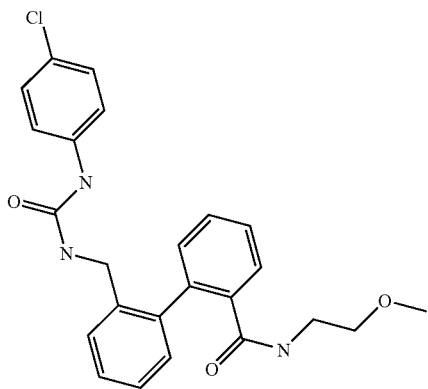 | 437 |
| 11 h | 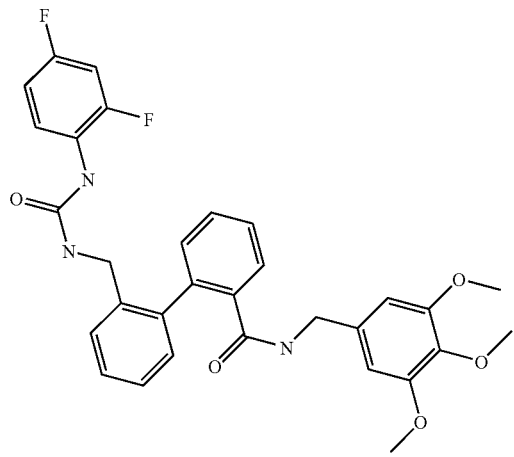 | 561 |
| 11 i | 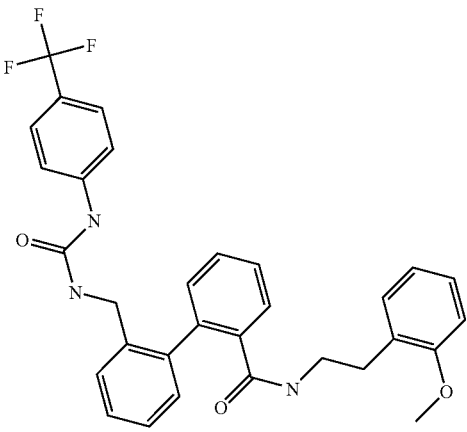 | 547 |

| Example No. | Structure | MS (ES+): m/e = |
|---|---|---|
| 11 j | 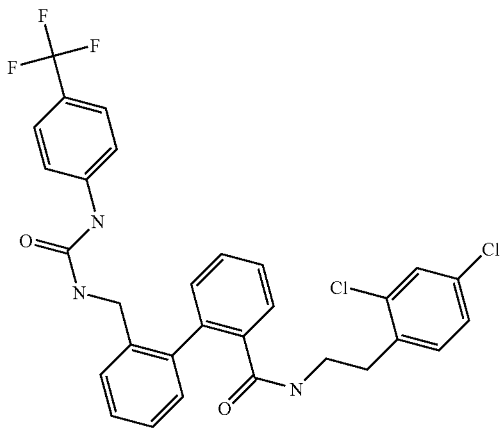 | 585 |
| 11 k | 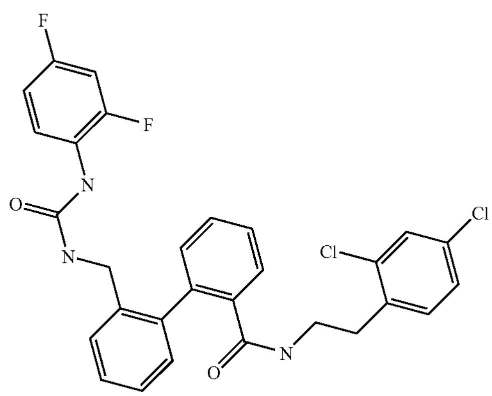 | 553 |
| 11 l | 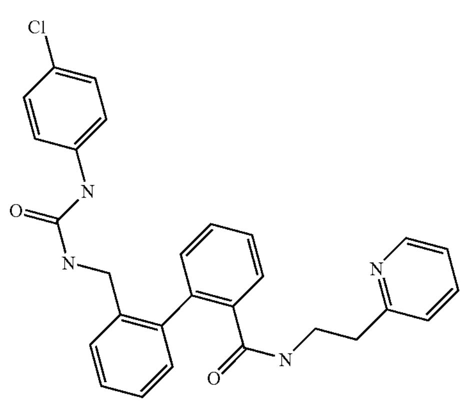 | 484 |

-continued
| Example No. | Structure | MS (ES+): m/e = |
|---|---|---|
| 11 m | 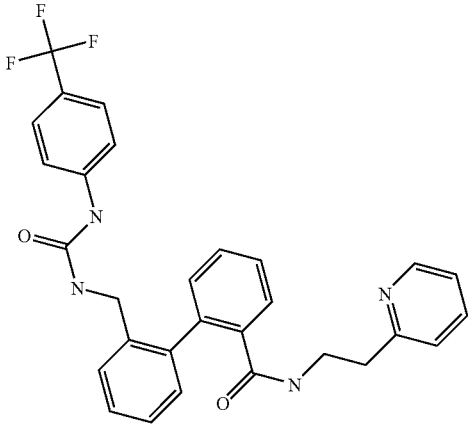 | 519 |
| 11 n | 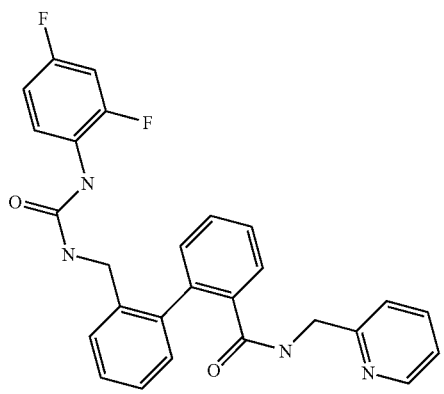 | 473 |
| 11 o | 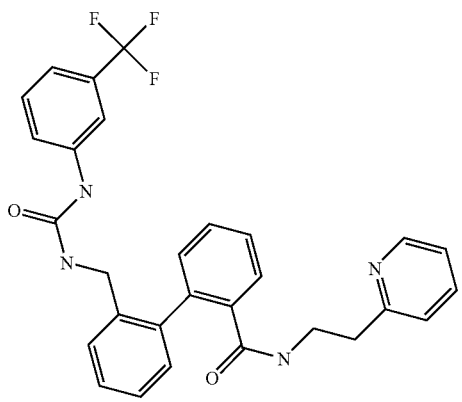 | 519 |

-continued

| Example No. | Structure | MS (ES+): m/e = |
|---|---|---|
| 11 p | 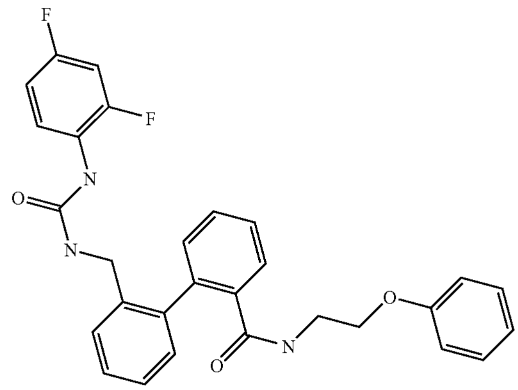 | 502 |
| 11 q | 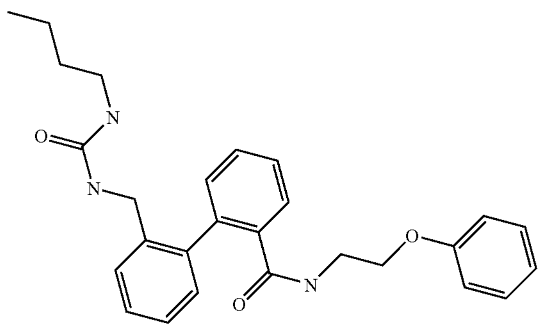 | 446 |
| 11 r | 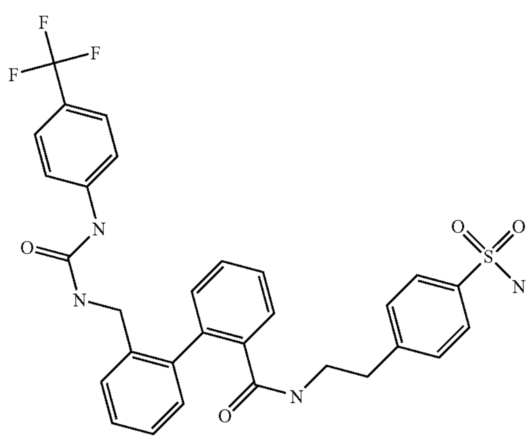 | 597 |

General Working Procedures for the Preparation of Compounds According to the Invention by Means of Solid-phase Synthesis:

The quantitative data in the procedures in each case always relate to the resin loading, which was determined by UV photometry after removal of the Fmoc protective group (see for example "The Combinatorial Chemistry Catalog", Novabiochem).

General Procedure for the Coupling of α-Fmoc-amino Acids to Rink Amide Resin

A solution of 1.5 equivalents each of HOBT, TOTU, DIPEA and the α-Fmoc amino acid in DMF (5 ml/g of resin) was added to Rink amide polystyrene resin (loading 1.2 mmol/g) and the mixture was shaken at room temperature for 12 h. The resin was filtered off and washed 3 times with 10 ml each of DMF, once with 10 ml of toluene, once with 10 ml of methanol and 3 times with 10 ml of dichloromethane. Determination of the loading according to the Fmoc method showed a loading of 0.9 mmol/g of carrier.

Removal of the Fmoc Protective Group

For the removal of the Fmoc protective group, the resin was preswollen in DMF at room temperature for 5 min. After addition of a solution of DMF/piperidine (4 ml/g of resin, 1:1), the mixture was shaken at room temperature for 20 min. The solution was filtered off with suction and the process was repeated. The removal of an analytical sample showed complete reaction according to HPLC/MS investigation. After complete reaction, the resin was washed three times with dichloromethane and employed directly in the coupling.

General Working Procedure for the Coupling of the Resin-bonded Amino Acids with the 2'-phthalimidomethylbiphenyl-2-carboxylic Acid (Precursor 2)

A solution of 12.2 mg (0.09 mmol) of HOBT, 29.5 mg (0.09 mmol) of TOTU, 16 µl (0.09 mmol) of DIPEA and 0.09 mmol of 2'-phthalimidomethylbiphenyl-2-carboxylic acid (precursor 2) in 5 ml of DMF was added to 100 mg of resin loaded with the amino acid (0.6-0.8 mmol/g) and the mixture was shaken at room temperature for 12 h. The resin was filtered off and washed 3 times with 10 ml each of DMF, once with 10 ml of toluene, once with 10 ml of methanol and 3 times with 10 ml of dichloromethane.

General Procedure for the Removal of the Phthalimido Protective Group on the Carrier 5 ml of a 10% strength solution of hydrazine in DMF were added to 1 g of resin loaded with the Fmoc-protected amino compound and the mixture was shaken at room temperature for 2 h. The resin was filtered off with suction. The resin was then washed 3 times each with 10 ml each of DMF and dichloromethane. The removal of an analytical sample showed complete reaction according to HPLC/MS investigation.

General Procedure for Coupling with Sulfonyl Chlorides

A solution of 0.16 ml (0.027 mmol) of DIPEA and 0.027 mmol of the sulfonyl chloride in 5 ml of DMF was added to 100 mg of resin loaded with the functionalized 2'-aminomethylbiphenyl-2-carboxylic acid and the mixture was shaken at room temperature for 12 h. The resin was filtered off and washed 3 times with 10 ml each of DMF, once with 10 ml of toluene, once with 10 ml of methanol and 3 times with 10 ml of dichloromethane.

General Working Procedure for Removal from the Resin

For removal, the resin was suspended in dichloromethane/trifluoroacetic acid (3 ml/0.1 g of resin) and shaken for 1 h. The resin was filtered and washed with 1 ml of dichloromethane. The combined removal solution was concentrated in a rotary concentrator. The residue was taken up in dichloromethane and chromatographed on silica gel using dichloromethane and ethyl acetate or purified by preparative HPLC.

The following products, inter alia, were obtained in this way:

| Example No. | Structure | | MS (ES+): m/e = |
|---|---|---|---|
| 12 a | 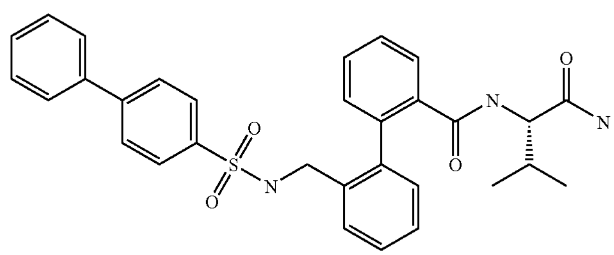 | Chiral | 542 |
| 12 b | 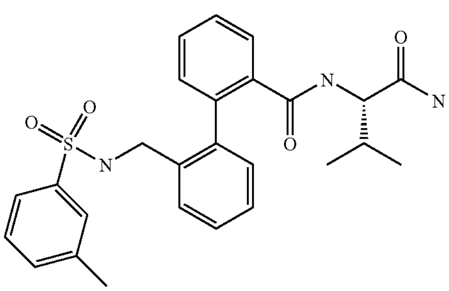 | Chiral | 480 |
| 12 c | 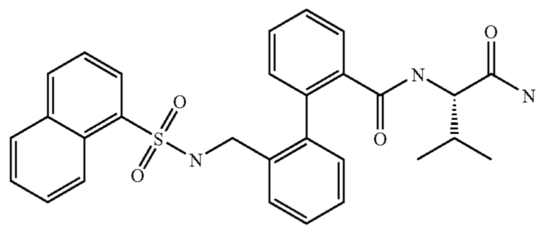 | Chiral | 516 |

-continued

| Example No. | Structure | MS (ES+): m/e = |
|---|---|---|
| 12 d | Chiral | 534 |
| 12 e | Chiral | 506 |
| 12 f | Chiral | 528 |
| 12 g | Chiral | 564 |
| 12 h | Chiral | 582 |

-continued

| Example No. | Structure | | MS (ES+): m/e = |
|---|---|---|---|
| 12 i | 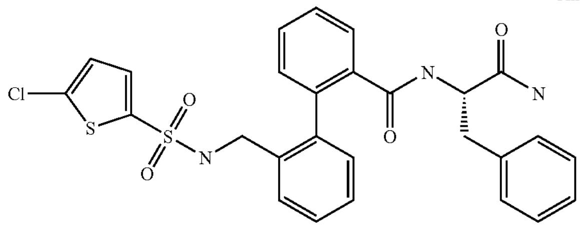 | Chiral | 554 |
| 12 j | 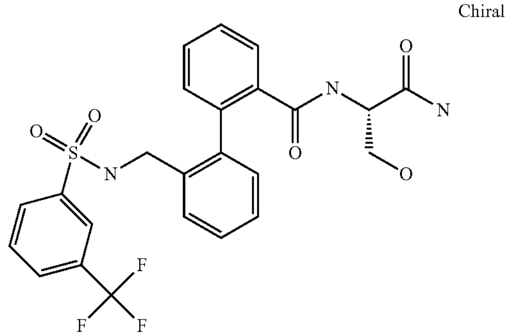 | Chiral | 522 |
| 12 k | 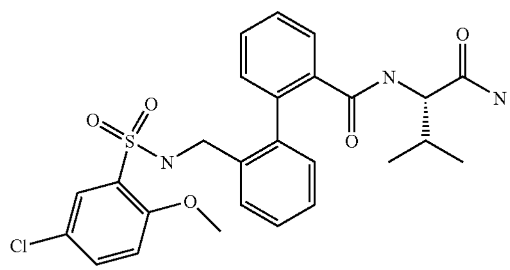 | Chiral | 530 |
| 12 l | 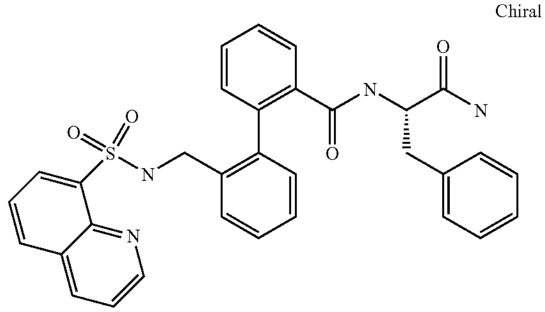 | Chiral | 565 |
| 12 m | 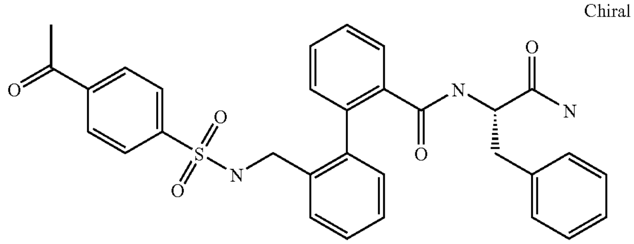 | Chiral | 556 |

Example 13 a

2-{[2'-(Benzyloxycarbonylaminomethyl)biphenyl-2-carbonyl]amino}-4-methylpentanoic acid

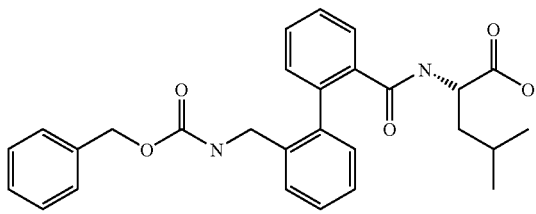

The compound was obtained from the methyl ester of Example 8 r by hydrolysis with potassium hydroxide in methanol/water at 60° C.

Examples 13 b-13 e

The following compounds were obtained by coupling of the carboxylic acid of Example 13 a with the appropriate amines according to the general method indicated in Example 8:

| Example No. | Structure | | MS (ES+): m/e = |
|---|---|---|---|
| 13 b | 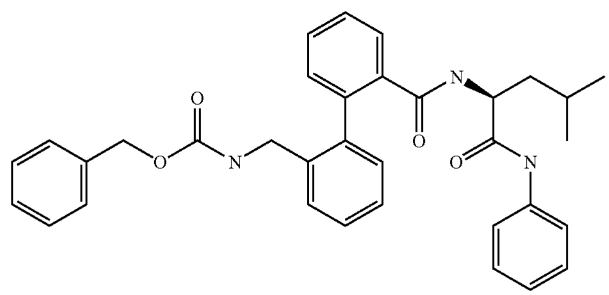 | Chiral | 550 |
| 13 c | 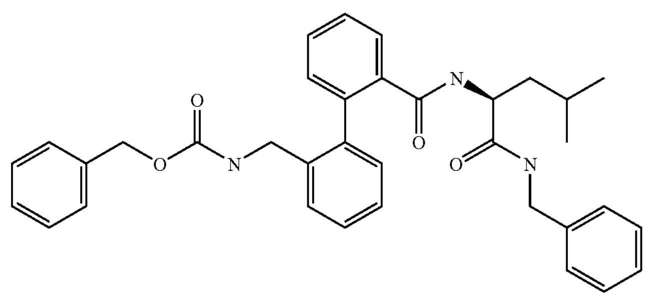 | Chiral | 564 |
| 13 d | 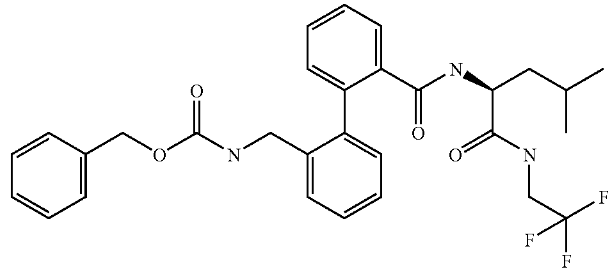 | Chiral | 556 |

| Example No. | Structure | | MS (ES+): m/e = |
|---|---|---|---|
| 13 e | (structure) | Chiral | 544 |

The following compounds were obtained by hydrogenolytic removal of the Z protective group of the compound of Example 13 c and subsequent reaction with the appropriate acid chlorides:

| Example No. | Structure | | MS (ES+): m/e = |
|---|---|---|---|
| 13 f | (structure) | Chiral | 556 |
| 13 g | (structure) | Chiral | 554 |

| Example No. | Structure | MS (ES+): m/e = |
|---|---|---|
| 13 h | Chiral | 592 |

20

Starting from the compound of Example 8 z, the following compound was obtained by hydrolysis and reaction with isopropylamine analogously to Examples 13 a-13 e:

| Example No. | Structure | MS (ES+): m/e = |
|---|---|---|
| 13 i | 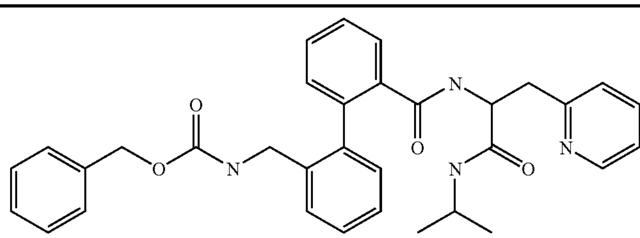 | 551 |

General Procedure for the Coupling of 2'-aminomethylbiphenyl-2-carboxylic acid (2,4-difluorobenzyl)amide with carboxylic acids to give carboxamides (Examples 14 a-14 f):

0.27 mmol of the appropriate carboxylic acid was stirred at RT for 30 min with 0.27 mmol of HOBT and 0.27 mmol of EDAC in 1 ml of THF. 0.26 mmol of 2'-aminomethylbiphenyl-2-carboxylic acid (2,4-difluorobenzyl)amide trifluoroacetate dissolved in 1 ml of THF was then added and the mixture was stirred at RT overnight. The reaction mixture was diluted with EA and washed with sodium bicarbonate solution and water. After concentrating the organic phase, the products were purified by means of preparative HPLC.

The following compounds were prepared in this way:

| Example No. | Structure | MS (ES+): m/e = |
|---|---|---|
| 14 a | 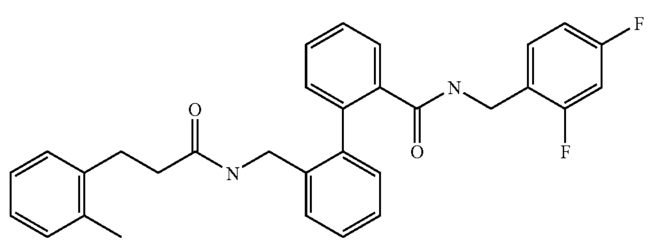 | 499 |

-continued
| Example No. | Structure | MS (ES+): m/e = |
|---|---|---|
| 14 b | 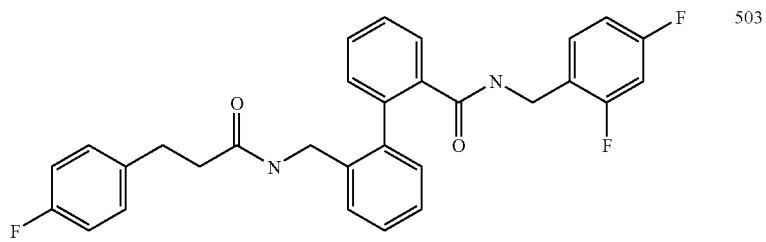 | 503 |
| 14 c | 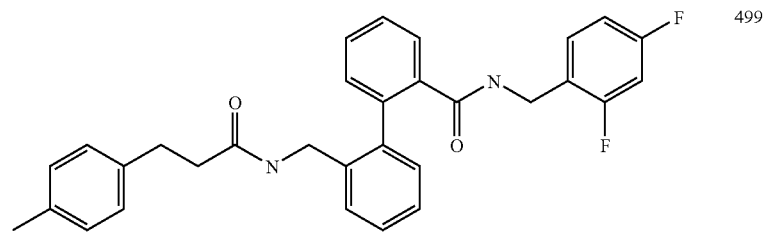 | 499 |
| 14 d | 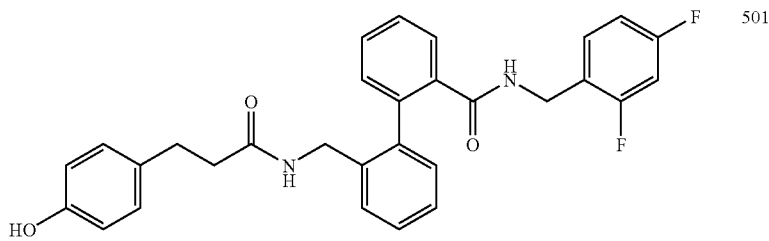 | 501 |
| 14 e | 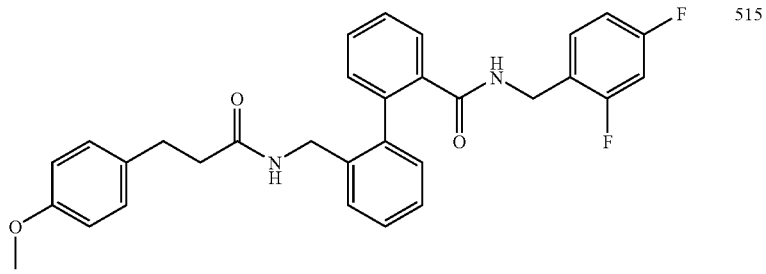 | 515 |
| 14 f | 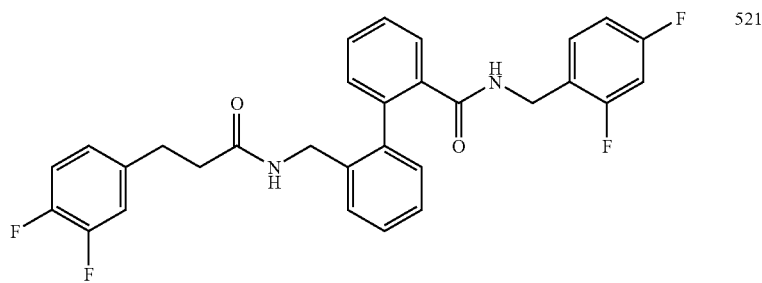 | 521 |

General Procedure for the Synthesis of Biphenyls by Suzuki Coupling (Examples 15 a-15 b)

58 mg (0.05 mmol) of tetrakistriphenylphosphine palladium and 1 mmol of the appropriate bromide were added to dimethoxyethane (10 ml) gassed with argon. After 10 min, 1.5 mmol of the appropriate boronic acid were added and finally 1 ml of a 2 molar sodium carbonate solution (2 mmol). The mixture was heated to reflux under argon for 18 h, cooled and diluted with 30 ml of methylene chloride. The mixture was washed with water and saturated sodium chloride solution, dried over sodium sulfate, concentrated and purified by chromatography on silica gel.

Example 15 a

2'-(tert.-Butyloxycarbonylaminomethyl)-4-nitrobiphenyl-2-carboxylic acid (3-methylbutyl)amide

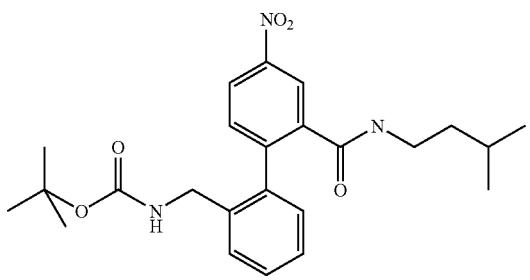

According to the general procedure, 350 mg (79% yield) of the nitro-substituted compound were obtained as a yellow solid.

Example 15 b

2'-(tert-Butyloxycarbonylaminomethyl)-4-methoxy-biphenyl-2-carboxylic acid (3-methylbutyl)amide

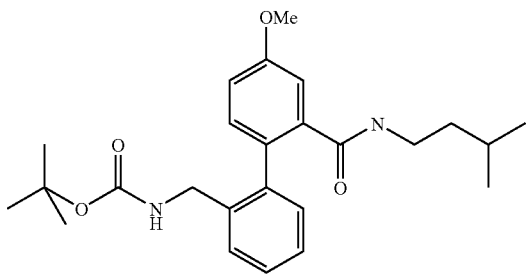

According to the general procedure, 170 mg (41% yield) of the methoxy-substituted compound were obtained as a viscous pale oil.

Example 16 a

2'-(tert.-Butyloxycarbonylaminomethyl)-4-aminobiphenyl-2-carboxylic acid (3-methylbutyl)amide

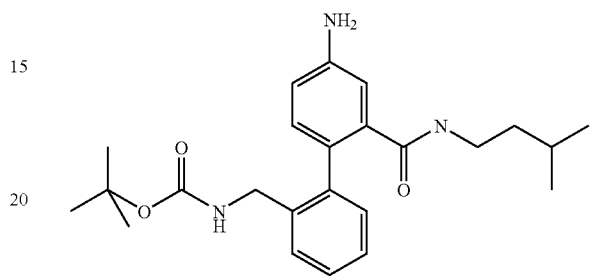

330 mg (0.75 mmol) of the nitro-substituted compound of Example 15 a were dissolved in ethyl acetate and hydrogenated under a hydrogen atmosphere (1 bar) using a spatula tipful of 10% palladium on carbon. After 2 h, the mixture was filtered through Celite and the clear solution was concentrated. Yield: 260 mg (84%).

Example 16 b

2'-(Benzyloxycarbonylaminomethyl)-4-hydroxybiphenyl-2-carboxylic Acid (3-methylbutyl)amide

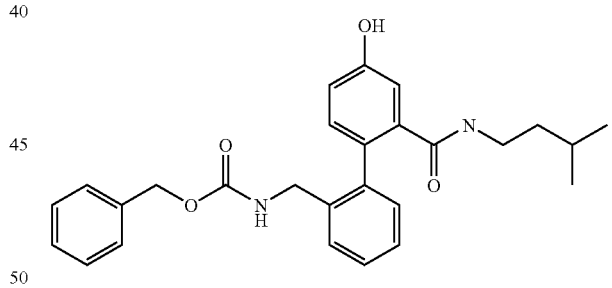

150 mg (0.35 mmol) of the methoxy-substituted compound of Example 15 b were dissolved in 5 ml of anhydrous methylene chloride and slowly treated at −70° C. with 1.4 ml (1.4 mmol) of a 1 molar solution of boron tribromide in n-hexane. After 10 min, the reaction solution was slowly warmed to 0° C. After 2 h at this temperature, it was neutralized with saturated sodium hydrogencarbonate solution, extracted with a total of 40 ml of methylene chloride, dried over sodium sulfate and concentrated. Of the crude product (88 mg) of 2'-aminomethyl-4-hydroxybiphenyl-2-carboxylic acid (3-methylbutyl)amide obtained, 30 mg (0.1 mmol) were dissolved in 3 ml of methylene chloride and treated with 11 mg (0.11 mmol) of triethylamine and 27 mg (0.11 mmol) of benzyloxycarbonyloxysuccinimide. After 3 h, the mixture was diluted with methylene chloride, washed with water, and the organic phase was dried over sodium sulfate and purified by RP-HPLC. 8 mg of 2'-(benzyloxycarbonylaminomethyl)-4-hydroxybiphenyl-2-carboxylic acid (3-methylbutyl)amide were obtained as a dark oil.

Example 17 a

{1-[2'-(3-Methyl-butylcarbamoyl)-biphenyl-2-yl]-ethyl}-carbamin acid tert.-butylate

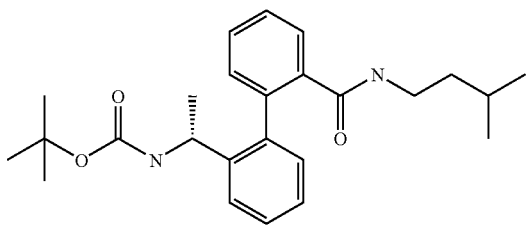

2.2 g (10 mmol) of N-Boc-(R)-phenethylamine were dissolved in 50 ml dry THF, it was cooled down to −78° C., and 14 ml of an 1.5 M solution of t-butyl lithium in pentane were added drop by drop (21 mmol). It was warmed up during 2 h to −20° C. Then 4.5 ml (40 mmol) of boric acid trimethylate was added, and it was warmed to RT. The solution was cooled to 0° C., it was acidified with 10% HCl until pH 6, the aqueous phase was extracted with dichloromethane, the unified organic phases were washed with saturated NaCl-solution, were dried and distilled off. The boron acid was obtained as a pale yellow solid foam, which was processed without further purification. The Suzuki coupling was carried out according to the general procedure (see example 15) using 1 mmol of 2-bromo-N-(3-methyl-butyl)-benzamide. After chromatograhic purification, 85 mg (0.2 mmol) of the biphenyl resulted.

Examples 17 b -17 e

The enantiomer 17 b was obtained analogously to Example 17 a. By removing the Boc-group and production of the respective carbamates the compounds 17a and 17b were transformed into the compounds of examples 17 c -17 e.

| example No. | structure | MS (ES+): m/z = |
|---|---|---|
| 17 b | 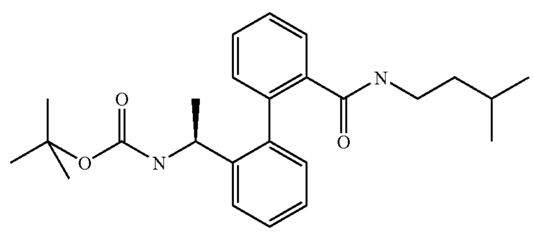 | 411 |
| 17 c | 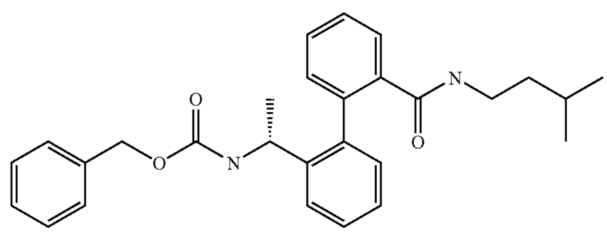 | 445 |
| 17 d | 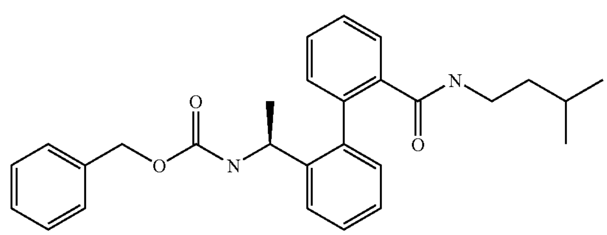 | 445 |
| 17 e | 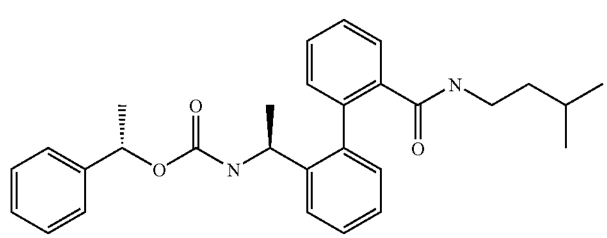 | 459 |

Analogously to the procedures described in examples 1 to 17, the following compounds were synthesized:

| example No. | structure | MS (ES+): m/z = |
|---|---|---|
| 18 a | 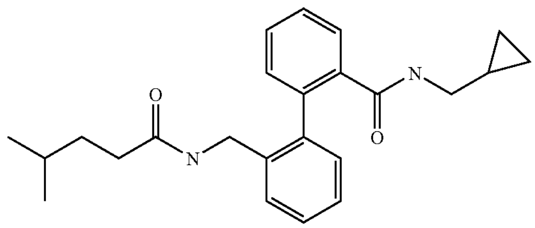 | 379 |
| 18 b | 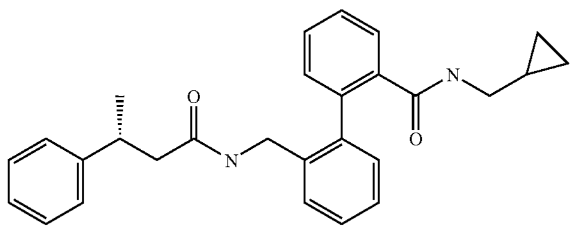 | 427 |
| 18 c | 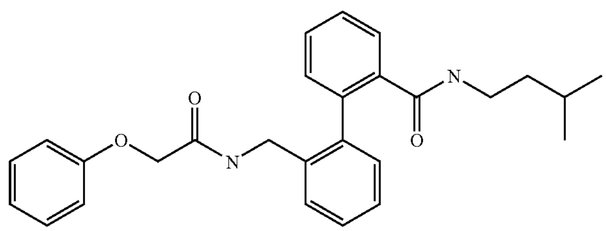 | 431 |
| 18 d | 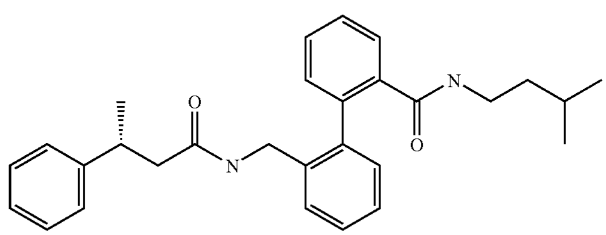 | 443 |
| 18 e | 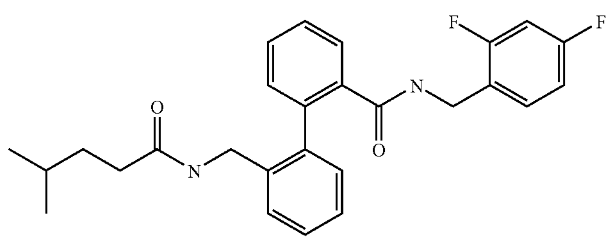 | 451 |
| 18 f | 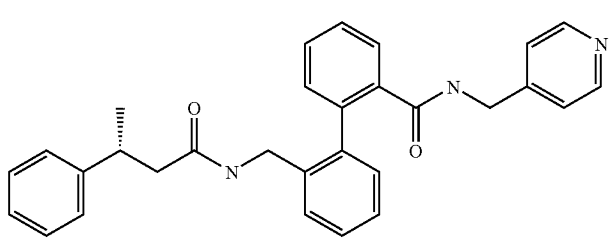 | 464 |

-continued

| example No. | structure | MS (ES+): m/z = |
|---|---|---|
| 18 g | 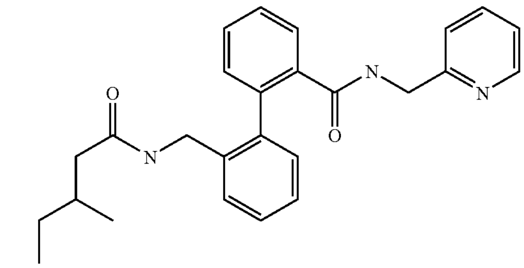 | 416 |
| 18 h | 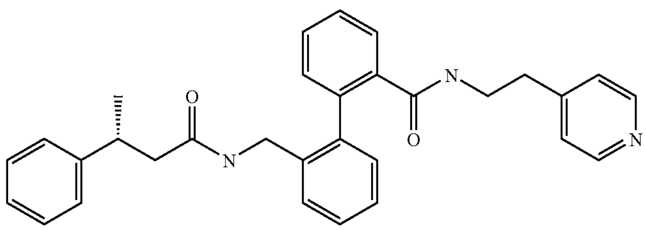 | 478 |
| 18 i | 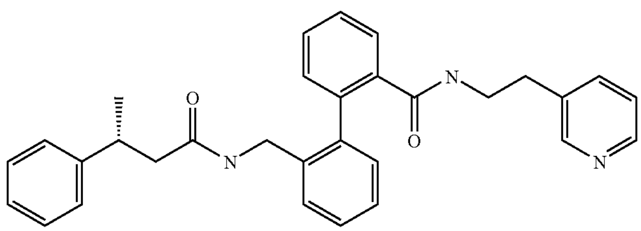 | 478 |
| 18 j | 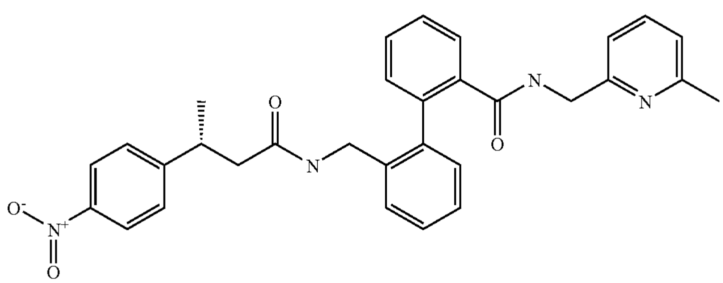 | 523 |
| 18 k | 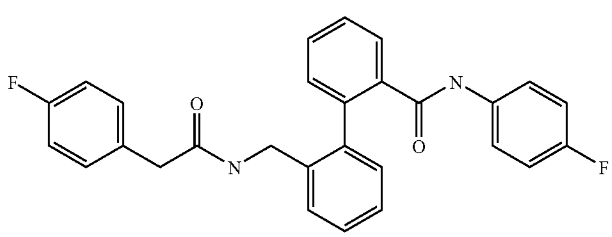 | 457 |
| 18 l | 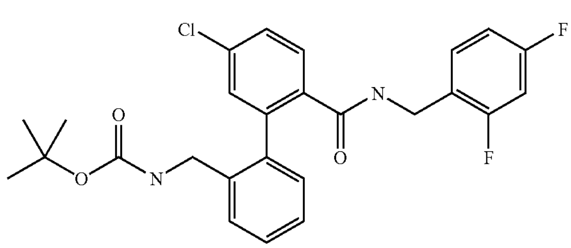 | 487 |

-continued

| example No. | structure | MS (ES+): m/z = |
|---|---|---|
| 18 m | 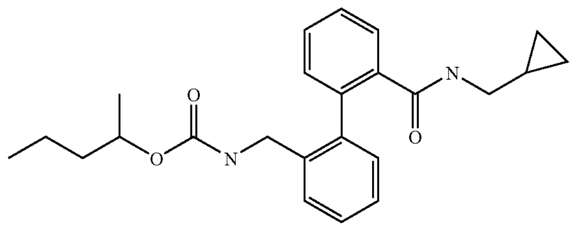 | 395 |
| 18 n | 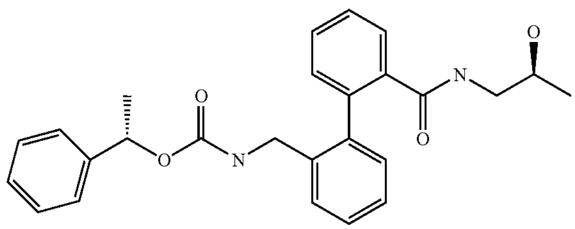 | 433 |
| 18 o | 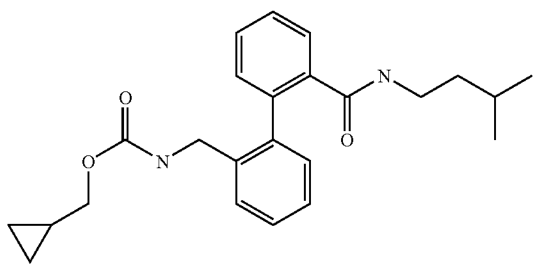 | 395 |
| 18 p | 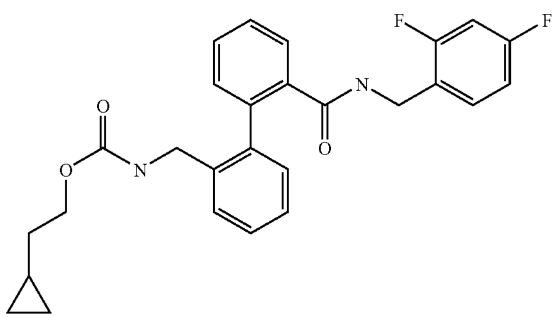 | 465 |
| 18 q | 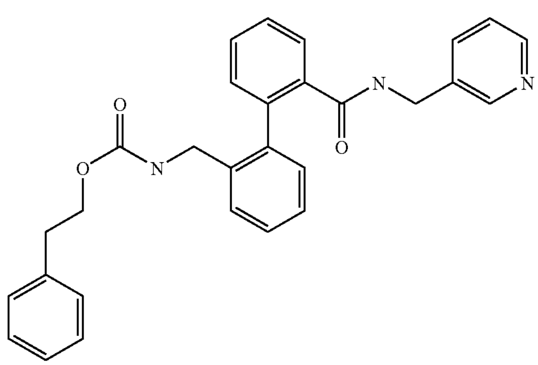 | 466 |

| example No. | structure | MS (ES+): m/z = |
|---|---|---|
| 18 r | 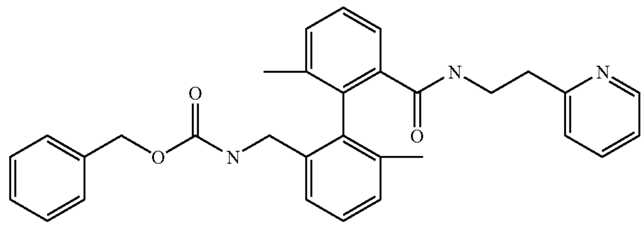 | 494 |
| 18 s | 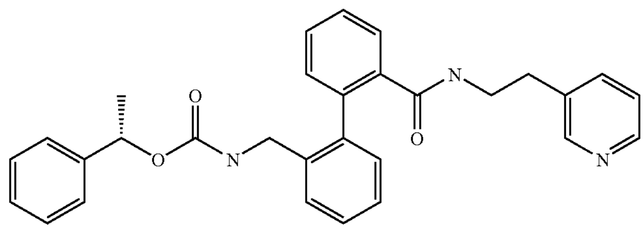 | 480 |
| 18 t | 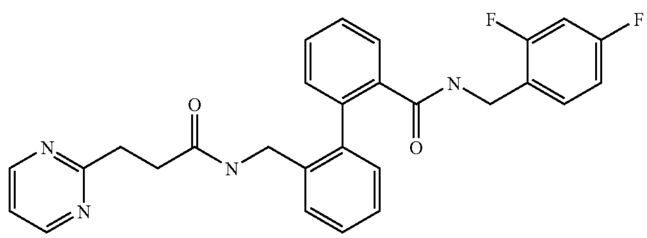 | 487 |
| 18 u | 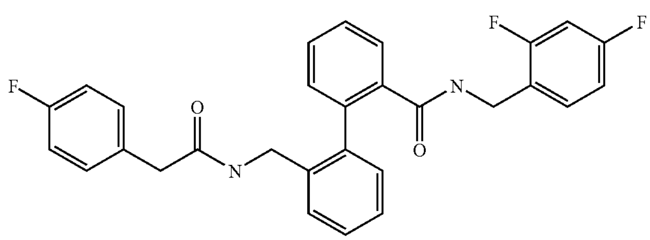 | 489 |
| 18 v | 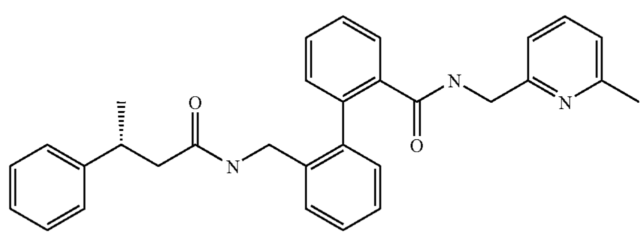 | 515 |
| 18 w | 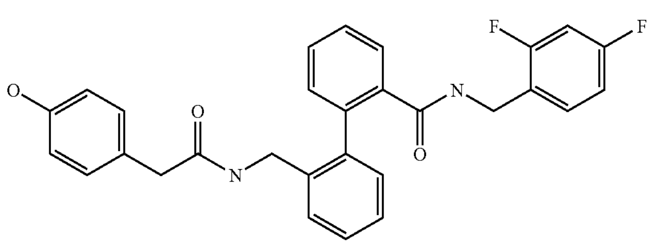 | 487 |

-continued

| example No. | structure | MS (ES+): m/z = |
|---|---|---|
| 18 x | 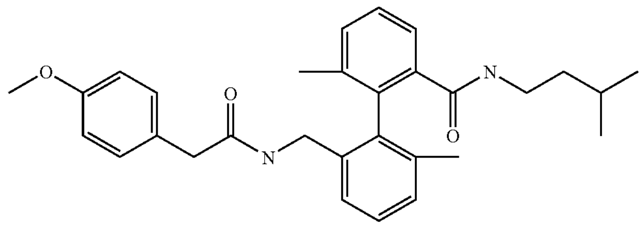 | 473 |
| 18 y | 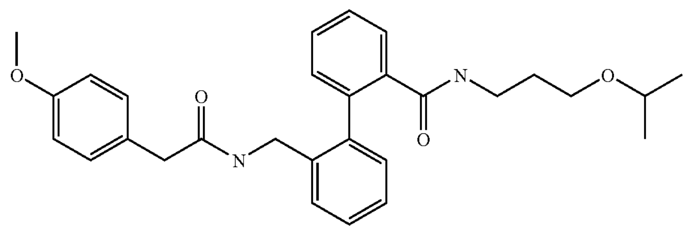 | 475 |
| 18 z | 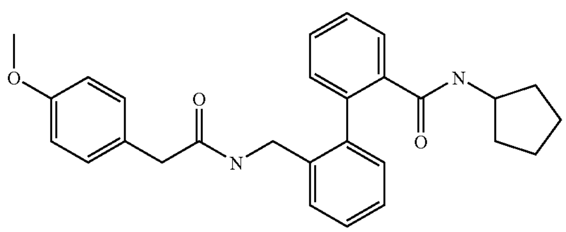 | 443 |
| 18 aa | 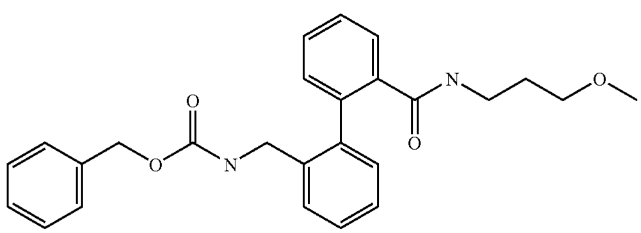 | 433 |
| 18 ab | 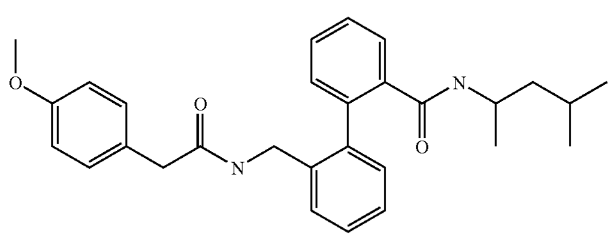 | 459 |
| 18 ac | 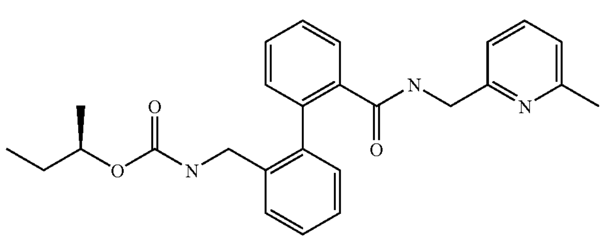 | 432 |

| example No. | structure | MS (ES+): m/z = |
|---|---|---|
| 18 ad | 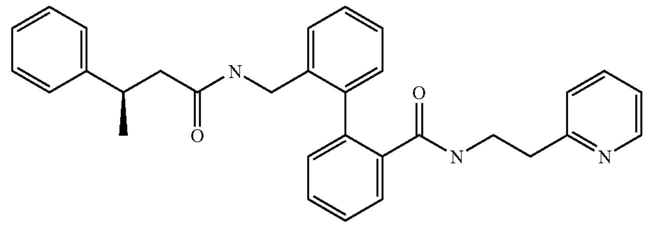 | 478 |
| 18 ae | 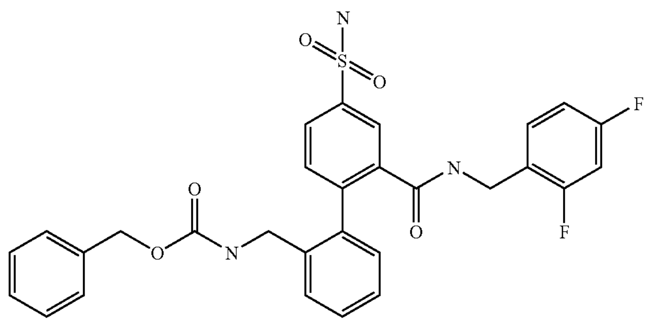 | 566 |
| 18 af | 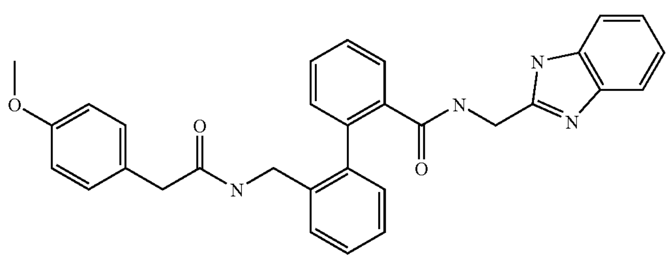 | 505 |
| 18 ag | 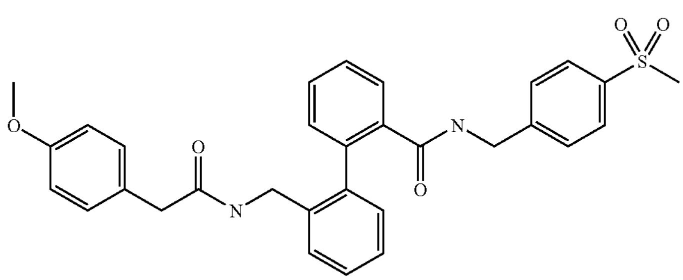 | 543 |
| 18 ah | 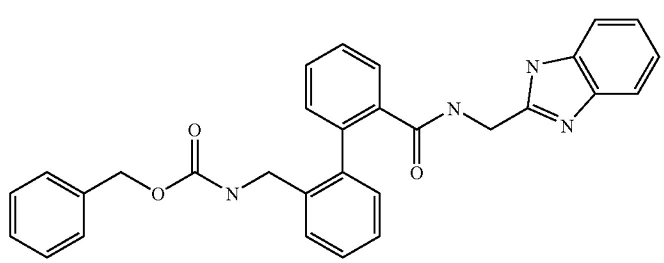 | 491 |

-continued

| example No. | structure | MS (ES+): m/z = |
|---|---|---|
| 18 ai | 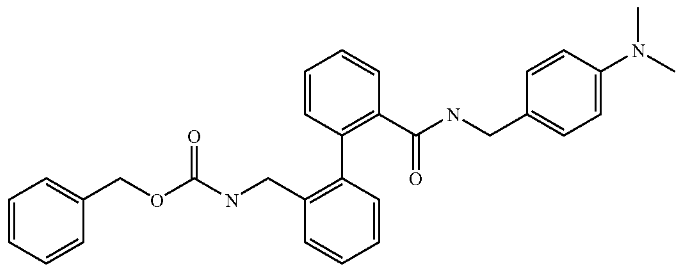 | 494 |

Pharmacological Investigations

Kv1.5 channels from humans were expressed in Xenopus oocytes. For this, oocytes from Xenopus laevis were first isolated and defolliculated. RNA encoding Kv1.5 synthesized in vitro was then injected into these oocytes. After Kv1.5 protein expression for 1-7 days, Kv1.5 currents were measured on the oocytes using the two-microelectrode voltage clamp technique. The Kv1.5 channels were in this case as a rule activated using voltage jumps to 0 mV and 40 mV lasting 500 ms. The bath was rinsed with a solution of the following composition: NaCl 96 mM, KCl 2 mM, $CaCl_2$ 1.8 mM, $MgCl_2$ 1 mM, HEPES 5 mM (titrated with NaOH to pH 7.4). These experiments were carried out at room temperature. The following were employed for data acquisition and analysis: Geneclamp amplifier (Axon Instruments, Foster City, USA) and MacLab D/A converter and software (AD Instruments, Castle Hill, Australia). The substances according to the invention were tested by adding them in different concentrations to the bath solution. The effects of the substances were calculated as the percentage inhibition of the Kv1.5 control current which was obtained when no substance was added to the solution. The data were then extrapolated using the Hill equation in order to determine the inhibitory concentration $IC_{50}$ for the respective substances.

The following $IC_{50}$ values were determined in this way for the compounds listed below:

| example No. | $IC_{50}$ [µM] | example No. | $IC_{50}$ [µM] | example No. | $IC_{50}$ [µM] | example No. | $IC_{50}$ [µM] |
|---|---|---|---|---|---|---|---|
| 1 a | 6.1 | 2 a | 2.6 | 4 a | 4.1 | 6 h | 3.0 |
| 1 b | 3.3 | 2 b | 0.8 | 4 c | 1.4 | 7 a | ~6.0 |
| 1 d | 1.0 | 2 c | 0.7 | 4 d | 1.8 | 8 a | 0.3 |
| 1 e | 0.5 | 2 d | 1.7 | 4 g | 3.4 | 8 b | 0.9 |
| 1 f | 0.4 | 2 e | 3.4 | 4 h | 1.8 | 8 d | 6.4 |
| 1 g | 0.4 | 2 f | 7.1 | 4 i | 4.7 | 8 j | 4.5 |
| 1 h | 4.3 | 2 g | 3.3 | 4 j | 7.1 | 8 k | 3.1 |
| 1 i | 1.7 | 2 h | 2.5 | 4 k | 2.2 | 8 l | 3.5 |
| 1 j | 0.2 | 2 i | 3.3 | 4 l | 0.8 | 8 m | 5.2 |
| 1 k | 2.4 | 2 j | 2.5 | 5 a | 4.5 | 8 n | 3.7 |
| 1 l | 1.4 | 2 k | 3.8 | 5 c | 7.8 | 8 o | 8.4 |
| 1 m | 0.7 | 2 m | 2.6 | 5 d | 1.9 | 8 p | 1.4 |
| 1 n | 1.4 | 3 d | 1.7 | 5 e | 7.2 | 8 q | 7.3 |
| 1 o | 4.4 | 3 k | 2.4 | 6 a | 4.4 | 8 r | 1.0 |
| 1 r | 0.8 | 3 l | 2.6 | 6 b | 1.8 | 8 s | 1.0 |
| 1 s | 1.7 | 3 p | 1.9 | 6 c | 2.5 | 8 x | 3.3 |
| 1 t | 1.3 | 3 r | 1.5 | 6 d | 3.1 | 8 y | 2.8 |
| 1 u | 0.8 | 3 | 3.0 | 6 e | 3.6 | 8 z | 1.6 |
| 8 aa | 0.8 | 8 ab | 1.2 | 8 ac | 1.1 | 9 b | 3.0 |
| 9 c | 2.0 | 9 f | 2.2 | 9 g | 2.2 | 11 a | 2.3 |
| 11 b | 7.3 | 11 d | 3.3 | 11 g | 7.8 | 11 h | 5.8 |
| 11 l | 2.7 | 11 m | 3.3 | 11 n | 5.9 | 11 o | 4.4 |
| 11 p | 7.3 | 12 c | 11.2 | 12 f | 11.3 | 12 g | 9.1 |
| 12 h | 4.8 | 12 l | 10.3 | 12 m | 7.7 | 13 b | ~3.0 |
| 13 c | 1.4 | 13 d | 0.5 | 13 e | 2.8 | 13 f | 3.4 |
| 13 g | 1.1 | 13 h | 1.4 | 13 i | 1.2 | 14 a | 3.6 |
| 14 b | 2.7 | 14 d | 2.0 | 14 e | 0.8 | 14 f | 2.5 |
| 15 b | 3.1 | 16 b | 5.2 | 18 a | 7.2 | 18 b | 0.4 |
| 18 c | 4.2 | 18 d | 0.4 | 18 e | 1.7 | 18 f | 1.3 |
| 18 g | 3.9 | 18 h | 0.8 | 18 i | 0.4 | 18 j | 0.7 |
| 18 k | 3.0 | 18 m | 2.1 | 18 n | 0.4 | 18 o | 3.6 |
| 18 p | 4.7 | 18 q | 3.2 | 18 r | 0.7 | 18 s | 0.9 |
| 18 u | 1.1 | 18 v | 0.4 | 18 w | 5.4 | 18 x | 4.6 |
| 17 d | 1.3 | 17 e | 1.8 | 17 c | 2.1 | 18 y | 1.9 |
| 18 z | 1.2 | 18 aa | 0.4 | 18 ab | 1.1 | 18 ac | 10 |
| 18 ad | 0.3 | 18 af | 5.8 | 18 ah | 2.1 | 18 ai | 6.6 |

We claim:

1. A compound represented by the chemical structure selected from the group consisting of:

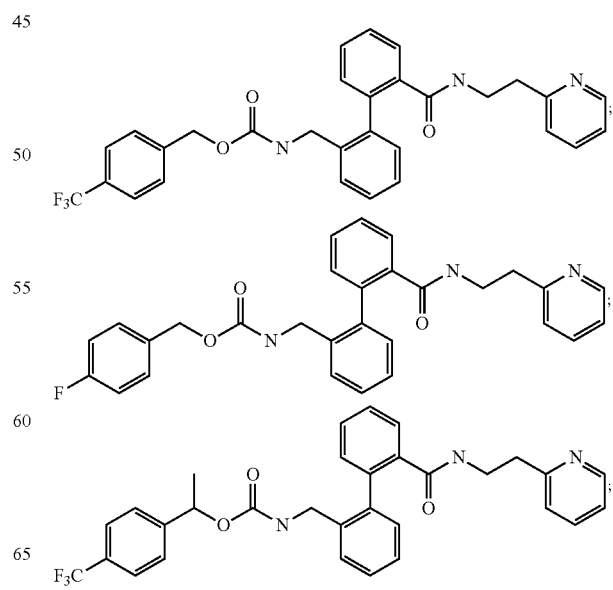

123
-continued
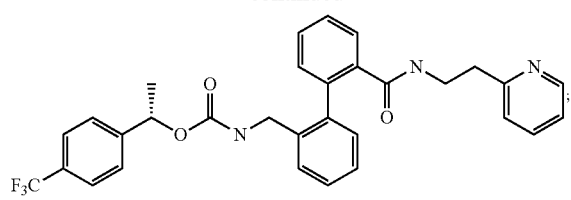
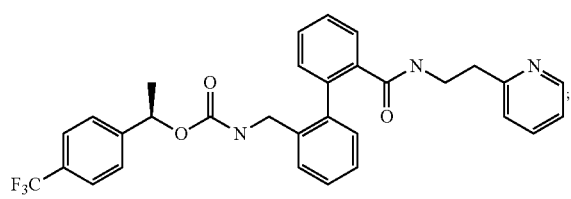
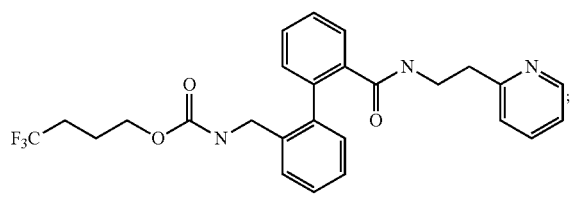
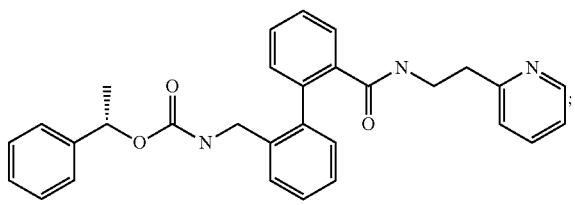
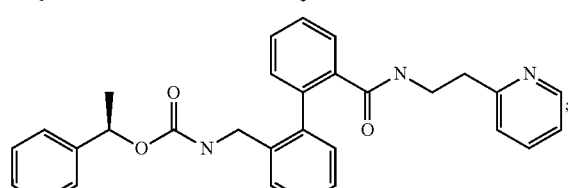
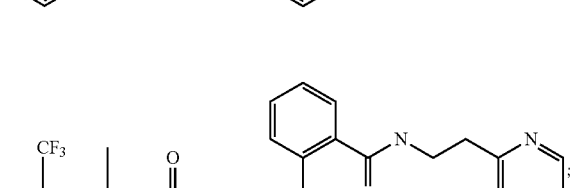
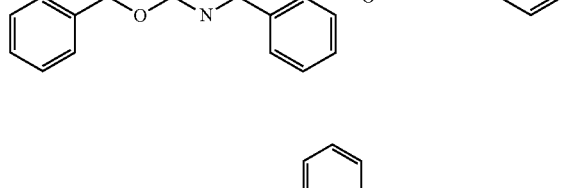
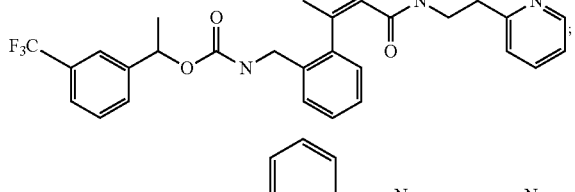
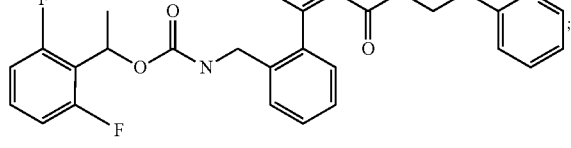
124
-continued
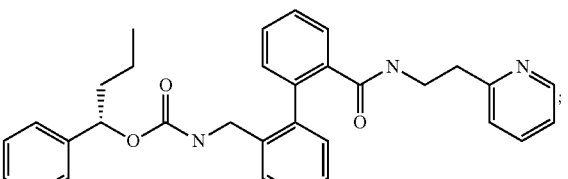
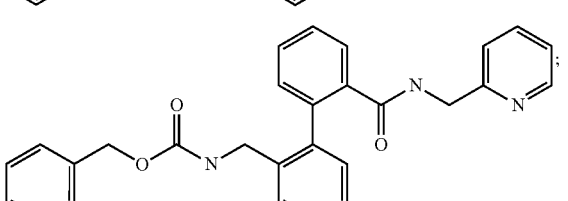
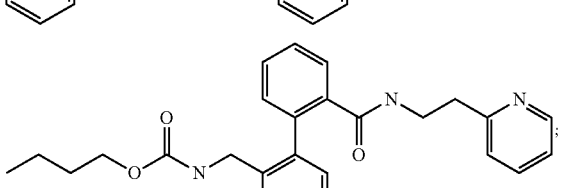
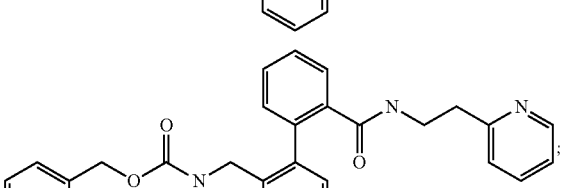
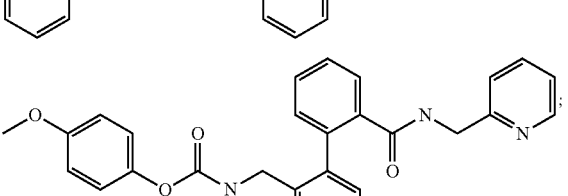
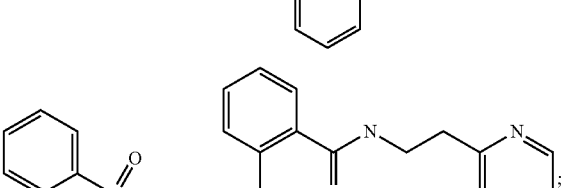
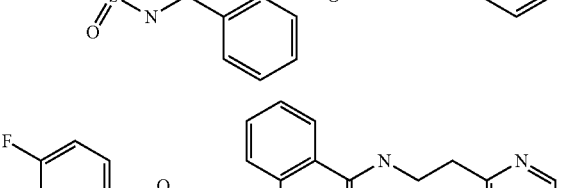
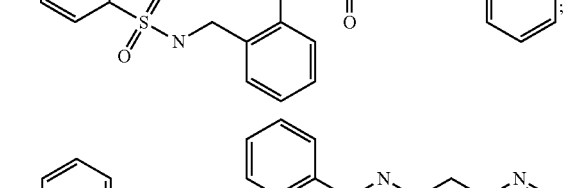
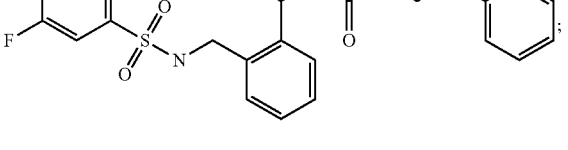

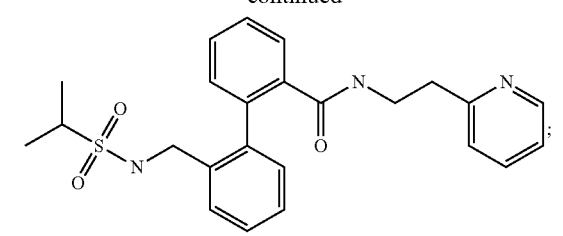
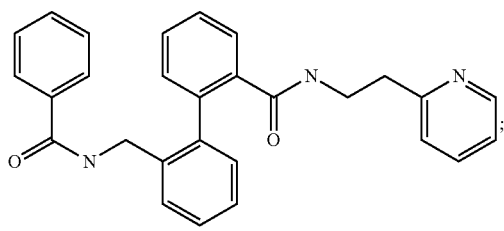
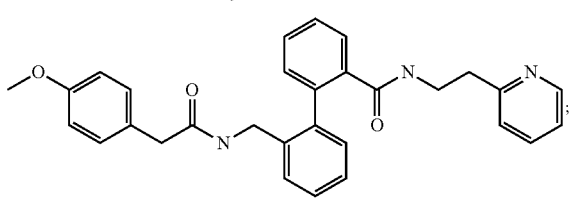
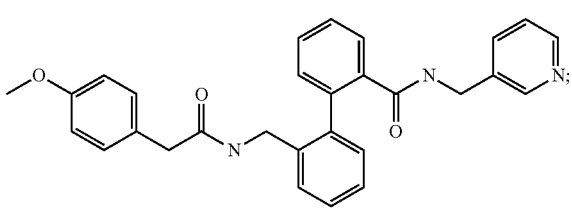
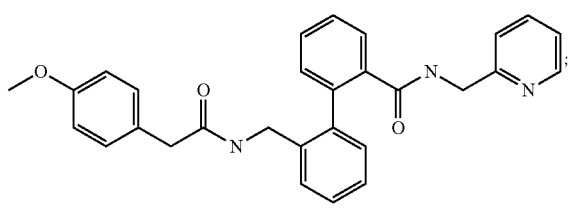
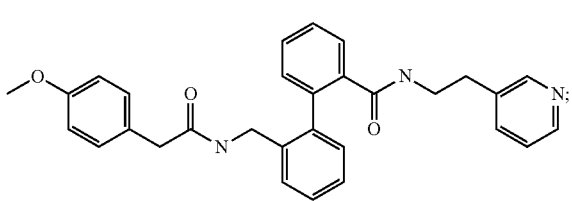
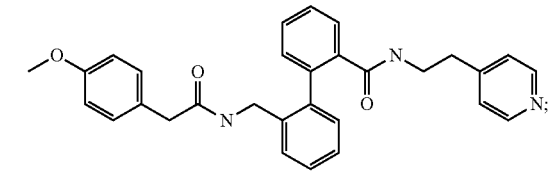
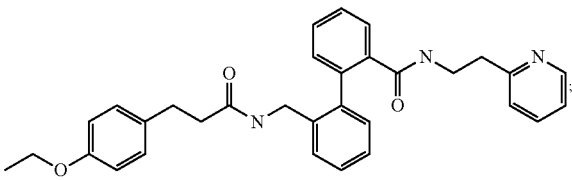
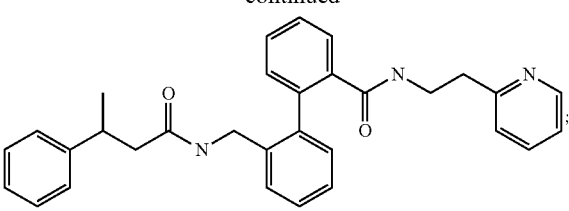
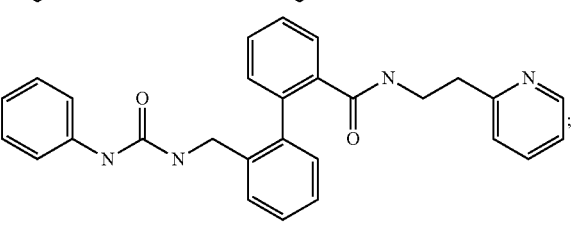
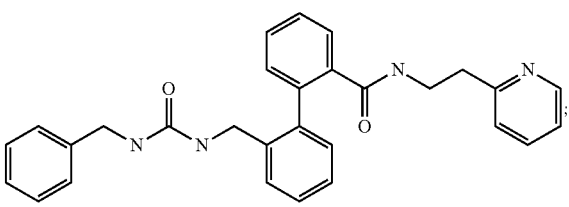
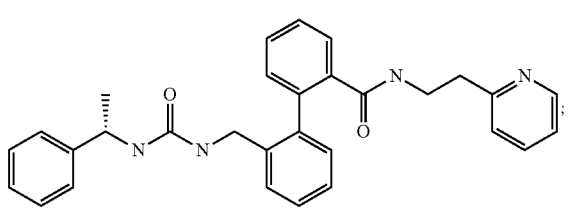
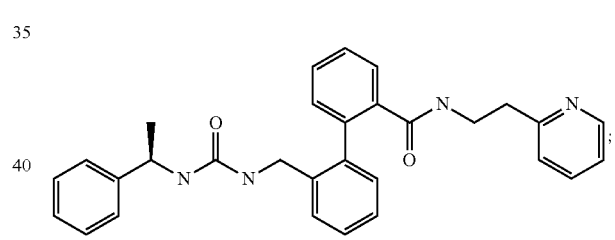
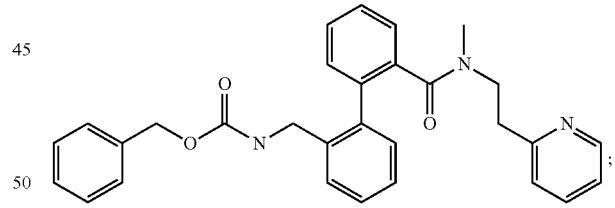
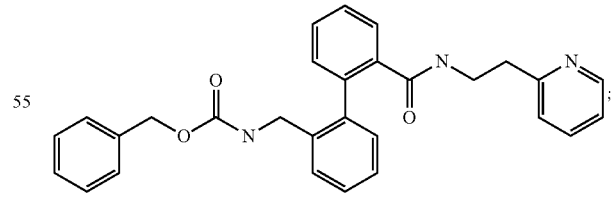
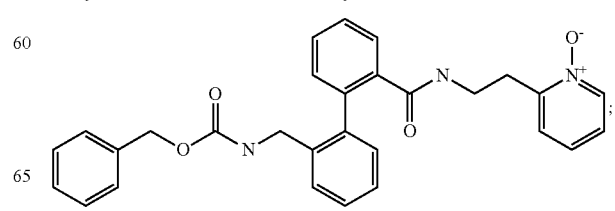

127
-continued
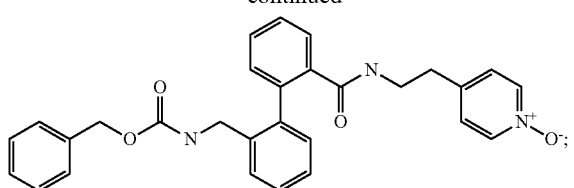
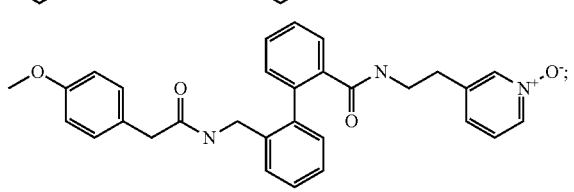
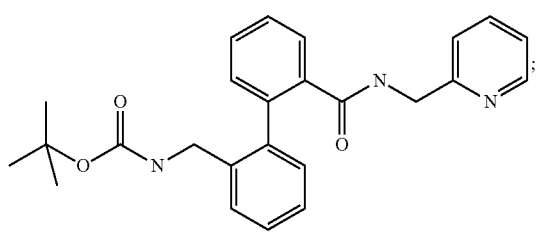
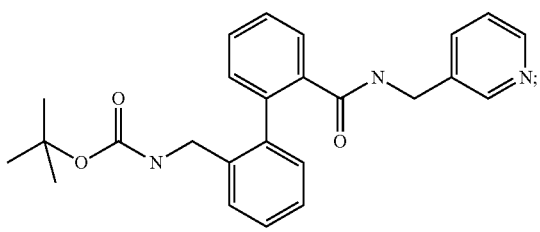
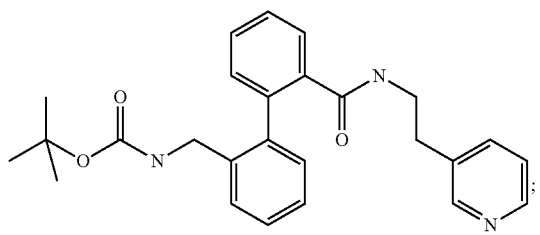
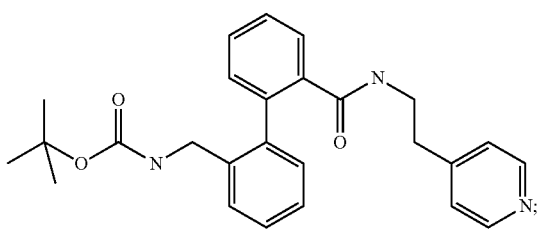
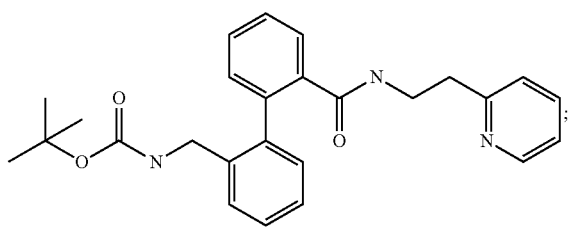
128
-continued
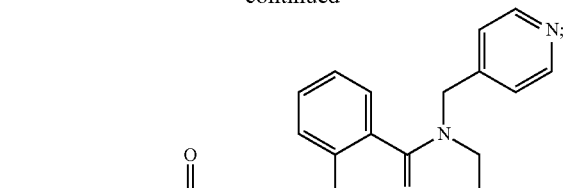
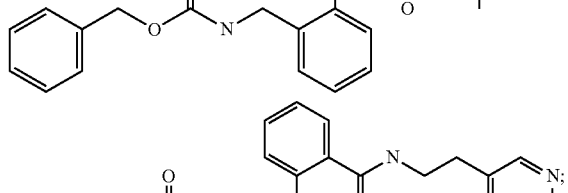
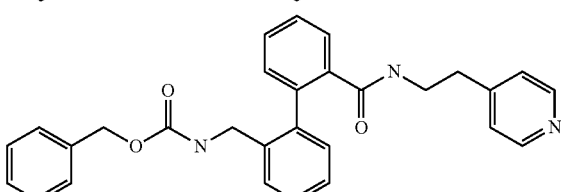
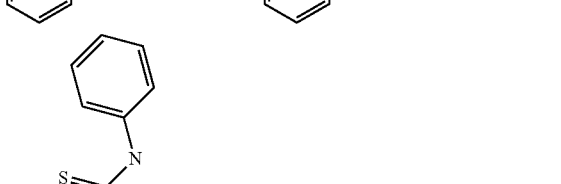
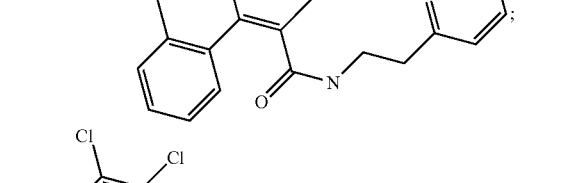
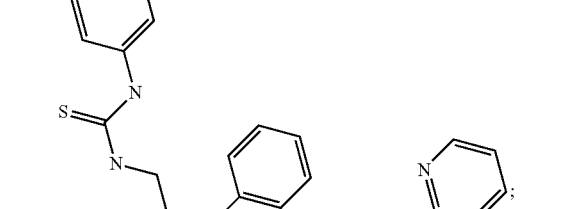
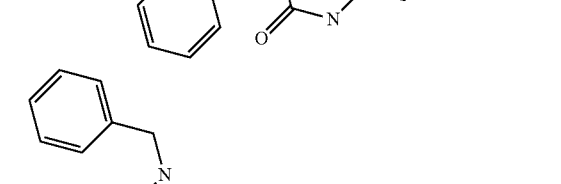
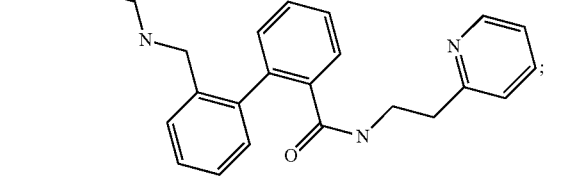

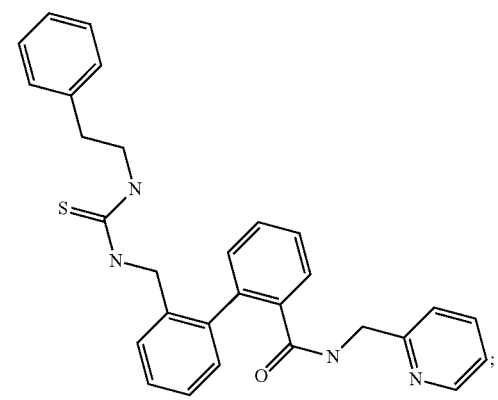
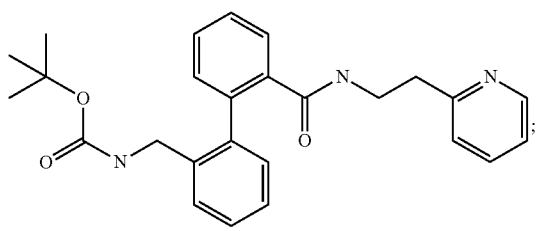
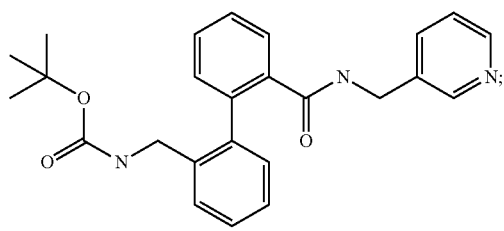
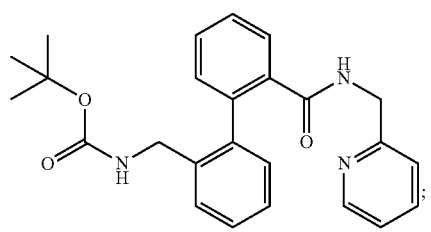
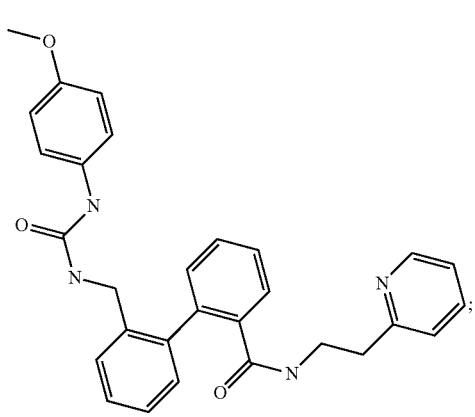
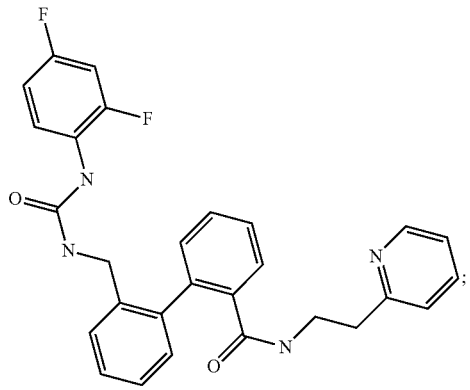
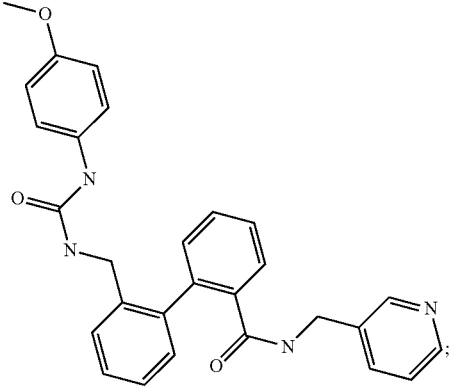
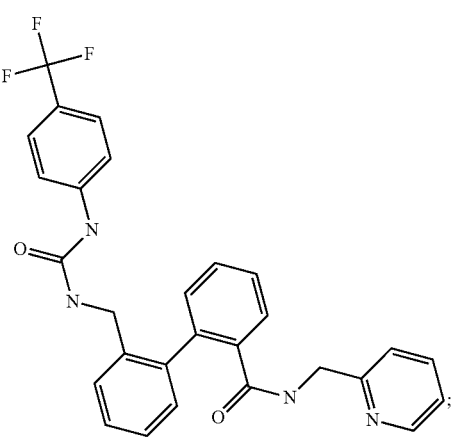
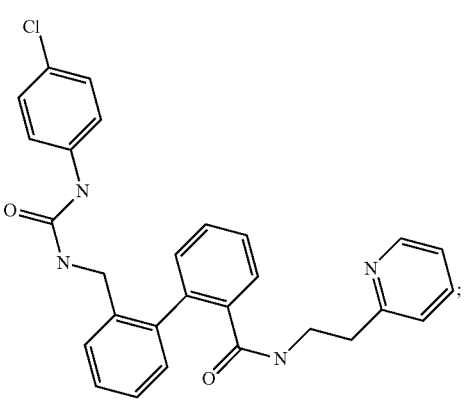

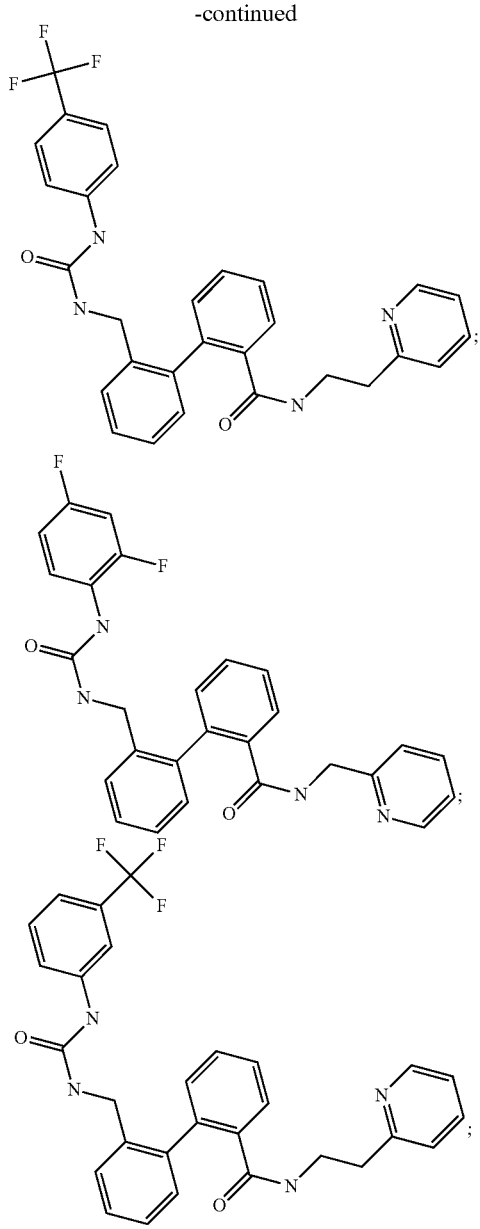

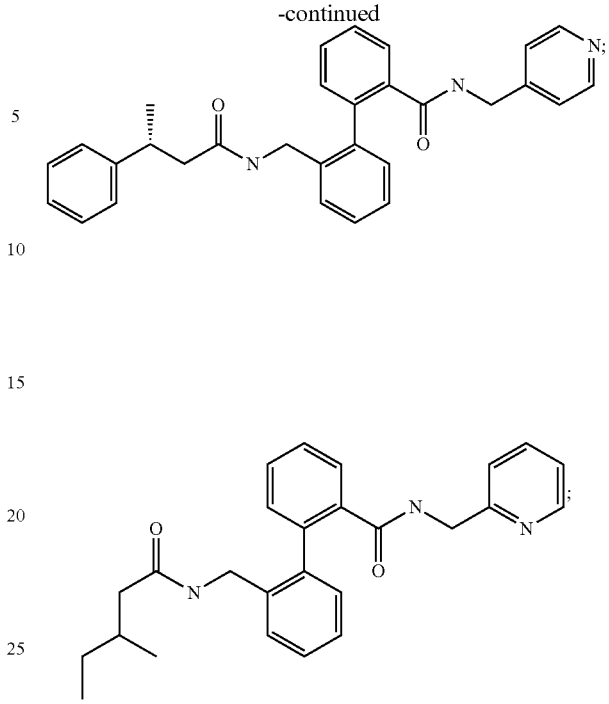

or a pharmaceutically acceptable salt thereof.

2. A pharmaceutical composition, comprising an effective amount of at least one compound as claimed in claim 1 together with a pharmaceutically acceptable vehicle or additive.

3. A pharmaceutical composition as claimed in claim 2, which further comprises one or more other pharmacologically active compounds.

4. A pharmaceutical composition as claimed in claim 3, comprising an effective amount of an IKr channel blocker.

5. A pharmaceutical composition as claimed in claim 3, comprising an effective amount of an IKs channel blocker.

6. A pharmaceutical composition as claimed in claim 3, comprising an effective amount of a beta-blocker.

* * * * *